(12) United States Patent
Black et al.

(10) Patent No.: US 7,122,187 B2
(45) Date of Patent: *Oct. 17, 2006

(54) TREATING AUTOIMMUNE DISEASES WITH HUMANIZED ANTI-CD40L ANTIBODY

(75) Inventors: Amelia Black, Los Gatos, CA (US); Nabil Hanna, Rancho Santa Fee, CA (US); Eduardo A. Padlan, Kensington, MD (US); Roland A. Newman, San Diego, CA (US)

(73) Assignee: Biogen IDEC Inc., Cambridge, MA (US)

( * ) Notice: Subject to any disclaimer, the term of this patent is extended or adjusted under 35 U.S.C. 154(b) by 610 days.

This patent is subject to a terminal disclaimer.

(21) Appl. No.: 10/171,681

(22) Filed: Jun. 17, 2002

(65) Prior Publication Data

US 2003/0170233 A1     Sep. 11, 2003

Related U.S. Application Data

(63) Continuation of application No. 08/925,339, filed on Sep. 8, 1997, now Pat. No. 6,440,418, which is a continuation-in-part of application No. 08/554,840, filed on Nov. 7, 1995, now Pat. No. 6,001,358.

(51) Int. Cl.
  *A61K 39/395* (2006.01)
  *C07K 16/28* (2006.01)

(52) U.S. Cl. ............... 424/154.1; 424/130.1; 424/133.1; 424/141.1; 424/143.1; 424/144.1; 424/153.1; 424/173.1; 530/387.1; 530/387.3; 530/388.1; 530/388.2; 530/388.22; 530/388.7; 530/388.73; 530/387.75

(58) Field of Classification Search ............. 424/130.1, 424/143.1, 154.1, 133.1, 144.1, 173.1, 141.1, 424/153.1; 530/387.1, 388.2, 388.73, 387.3, 530/388.22, 388.75, 388.1, 388.7
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |
| 4,975,369 A | 12/1990 | Beavers | |
| 4,978,745 A | 12/1990 | Schoemaker | |
| 5,474,771 A | 12/1995 | Lederman | |
| 5,683,693 A | 11/1997 | Noelle | |
| 5,747,037 A | 5/1998 | Noelle | |
| 5,833,987 A | 11/1998 | Noelle | |
| 5,876,718 A | 3/1999 | Noelle | |
| 5,902,585 A | 5/1999 | Noelle | |
| 6,001,358 A * | 12/1999 | Black et al. | 424/154.1 |
| 6,136,310 A * | 10/2000 | Hanna et al. | 424/154.1 |
| 6,440,418 B1 * | 8/2002 | Black et al. | 424/154.1 |
| 6,506,383 B1 * | 1/2003 | Black et al. | 424/154.1 |

FOREIGN PATENT DOCUMENTS

| | | |
|---|---|---|
| EP | 0 451 216 B1 | 10/1991 |
| EP | 0 519 596 A1 | 12/1992 |
| EP | 0 555 880 A2 | 8/1993 |
| EP | 0 555 880 A3 | 8/1993 |
| EP | 0 585 943 | 3/1994 |
| EP | 0 682 040 A1 | 11/1995 |
| WO | WO93/08207 | 4/1993 |
| WO | WO93/09812 | 5/1993 |
| WO | WO94/04570 | 3/1994 |
| WO | WO95/06480 | 3/1995 |
| WO | WO95/06666 | 3/1995 |
| WO | WO95/28957 | 11/1995 |
| WO | WO96/23071 | 8/1996 |
| WO | WO97/17446 | 5/1997 |
| WO | WO98/08541 | 3/1998 |
| WO | WO99/12566 | 3/1999 |

OTHER PUBLICATIONS

Duncan et al. Nature 332: 563-564, 1988.*
Alderson MR, et al., "CD40 expression by human monocytes: regulation by cytokines and activation of monocytes by the ligand for CD40," *J Exp Med,* 1993, 178: 669-74.
Alexander-Miller, et al., "Alloreactive cytotoxic T lymphocytes generated in the presence of viral-derived peptides show exquisite peptide and MHC specificity," J. Immunol., 1993, 151:1-10.
Allen RC, et al., "CD40 ligand gene defects responsible for X-linked hyper-IgM syndrome," *Science,* 1993, 259: 990-3.
Andersson J, et al., "T-cell-dependent B-cell stimulation is H-2 restricted and antigen dependent only at the resting B-cell level," *Proc Natl Acad Sci U S A,* 1980, 77: 1612-6.
Armitage RJ, et al., "Molecular and biological characterization of a murine ligand for CD40," *Nature,* 1992, 357: 80-2.
Aruffo A, et al., "The CD40 ligand, gp39, is defective in activated T cells from patients with X-linked hyper-IgM syndrome," *Cell,* 1993, 72: 291-300.
Bach JF, "Immunosuppressive therapy of autoimmune diseases," *Trends Pharmacol Sci.,* 1993, 14(5):213-6.
Bartlett WC, et al., "Cognate interactions between helpher T cells and B cells. II. Dissection of cognate help by using a class II-restricted, antigen-specific, IL-2-dependent helper T cell clone," *J Immunol,* 1989, 143:1745-54.

(Continued)

*Primary Examiner*—Phillip Gambel
(74) *Attorney, Agent, or Firm*—Pillsbury Winthrop Shaw Pittman LLP

(57) ABSTRACT

The present invention is directed to humanized antibodies which bind human gp39 and their use as therapeutic agents. These humanized antibodies are especially useful for treatment of autoimmune diseases; and an immunosuppressant during transplantation of heterologous cells, tissues or organs, cell therapy, and gene therapy.

8 Claims, 15 Drawing Sheets

OTHER PUBLICATIONS

Bartlett WC, et al., "Cognate interactions between helper T cells and B cells. IV. Requirements for the expression of effector phase activity by helper T cells," *J Immunol*, 1990, 145: 3956-62.

Bebbington CR, et al., "High-level expression of a recombinant antibody from myeloma cells using a glutamine synthetase gene as an amplifiable selectable marker," *Biol. Technology*, 1992, 10:169.

Benhar et al., "Rapid humanization of the Fv of monoclonal antibody B3 by using framework exchange of the recombinant immunotoxin B3(Fv)-PE38," *Proc. Natl. Acad. Sci. USA*, 1994, 91:12051-5.

Bhatia S., et al., "In vivo administration of anti-CD40 ligand (gp39) blocks the rejection of MHC class II disparate skin allografts," 9th Intl. Congress of Immunology, Jul. 23-29, 1995, San Francisco, CA, p. 311.

Biancone L. et al., "Inhibition of the CD40-CD40ligand pathway prevents murine membranous glomerulonephritis," *Kidney Int.*, 1995, 48(2):458-68.

Blair P. et al., "CD40 ligand (CD154) triggers a short-term CD4+ T cell activation response that results in secretion of immunomodulatory cytokines and apoptosis," *The Journal of Experimental Medicine*, 2000, 191(4):651-60.

Brennan FM, et al., "Enhanced expression of tumor necrosis factor receptor mRNA and protein in mononuclear isolated from rheumatoid arthritis synovial joints," *Eur J Immunol*, 1992, 22: 1907-12.

Brian AA, "Stimulation of B-cell proliferation by membrane-associated molecules from activated T cells," *Proc Natl Acad Sci U S A*, 1988, 85: 564-8.

Bulens et al., "Construction and characterization of a functional chimeric murine-human antibody directed against human fibrin fragment-D dimer," *Eur. J. Biochem.*, 1991, 195:235-42.

Burns C, et al., "Anti-CD40 Ligand antibody treatment of NZB/NZW murine lupus-like nephritis," Arthritis and Rheumatism, 1994, 37(Suppl):S390 (Poster 1371).

Carlsson et al., "Human peripheral blood lymphocytes transplanted into SCID mice constitute in vivo culture system exhibiting several parameters found in a normal humoral immune response and are a source of immunocytes for the production of human monoclonal antibodies," *J. Immunol.* 1992, 148:1065.

Caron et al., "Biological and immunological features of humanized M195 (Anti-CD33) monoclonal antibodies," *Cancer Res.*, 1992, 32:67671-7.

Carroll et al., "Hybridoma fusion cell lines contain an aberrant kappa transcript," *Mol. Immunol.*, 1988, 10:991.

Cathcart ES, et al., "Experimental arthritis in a nonhuman primate. I. Induction by bovine type II collagen," *Lab Invest*, 1986, 54: 26-31.

Chambers-Slater K, et al., "A humanized anti-human primate," *The FASEB Journal*, Mar. 15, 1999, 13(5):2, p. A988.

Chaudhary VK, et al., "A recombinant immunotoxin consisting of two antibody variable domains fused to *Pseudomonas exotoxin,*" *Nature*, 1989, 339:394-7.

Chu CQ, et al., "Localization of tumor necrosis factor alpha in synovial tissues and at the cartilage-pannus junction in patients with rheumatoid arthritis," *Arthritis Rheum*, 1991, 34: 1125-32.

Claman HN and Chaperon, "Immunologic complementation between thymus and marrow cells-a model for the two-cell theory of immunocompetence," *Transplant Rev*, 1969, 1: 92-113.

Clark EA, et al., "CD40: a cytokine receptor in search of a ligand," *Tissue Antigens*, 1990, 36: 33-6.

Clark EA et al., "How B and T cells talk to each other," *Nature*, 1994, 367(6462):425-8.

Clement LT, et al., "Small, resting B cells can be induced to proliferate by direct signals from activated helper T cells," *J Immunol*, 1984, 132: 740-4.

Cobbold SP, et al., Monoclonal antibodies to promote marrow engraftment and tissue graft tolerance, Nature, 1986, 323(6084):164-6.

Colcher et al., "Characterization and biodistribution of recombinant/chimeric constructs of monoclonal antibody B72.3," *Cancer Res.*, 1989, 49:1738-45.

Coloma, et al., "Novel vectors for the expressilon of antibody molecules using variable regiions generated by polymerase chain reaction," *J. Immunol. Meth.*, 1992, 152:89-104.

Courtenay et al., "Immunisation against heterologous type II collagen induces arthritis in mice," *Nature*, 1980, 283(5748):666-8.

Couto et al., "Humanization of KC4G3, an antihuman carcinoma antibody," *Hybridoma*, 1994, 13(3):215-9.

Cox et al., "A directory of human germ-line Vx segments reveals a strong bias in their usage," *Eur. J. Immunol.*, 1994, 24:827-36.

Crow et al., "Direct T Helper-B cell interactions Induce an early B cell activation antigen," *J Exp Med.*, 1986, 164:1760-72.

Crow et al., "Human peripheral blood T helper cell-induced B cell activation results in B cell surface expression of the CD23 (BLAST-2) antigen," *Cell Immunol.* 1989, 121(1):99-112.

De Waele et al., "Expression in non-lymphoid cells of mouse recombinant immunoglobulin directed against the tumour marker human placental alkaline phosphatase," *Eur. J. Biochem.*, 1988, 176:287-95.

DiGiovane et al., "tumour necrosis factor in synovial exudates," *Ann. Rheum. Dis.*, 1988, 47:68.

Dillman RO, "Monoclonal antibodies for treating cancer." Ann Intern Med. , 1989, 111(7):592-603.

DiSanto JP, et al., "CD40 ligand mutations in x-linked immunodeficiency with hyper-IgM," *Nature*, 1993, 361: 541-3.

Dorai et al., "The effect of dihydrofolate reductase-mediated gene amplification on the expression of transfected immunoglobulin genes," *J. Immunol.*, 1987, 139(12):4232-41.

Duchosal et al., "The hu-PBL-SCID mouse model. Long-term human serologic evolution associated with the xenogeneic transfer of human peripheral blood leukocytes into SCID mice," *Cell Immunol.*, 1992, 139:468.

Durie FH, et al., "Prevention of collagen-induced arthritis with an antibody to gp39, the ligand for CD40," *Science*, 1993, 261: 1328-30.

Durie FH, et al., "Antibody to the ligand of CD40, gp39, blocks the occurrence of the acute and chronic forms of graft-vs-host diseases," *J. Clin. Invest.*, 1994, 94:1333-8.

Durie, FH, et al., "Allogeneic Tolerance Induced by Treatment with an antibody to the ligand for DC40," 1994, FASEB Journal, Abstracts Part I, Ab. No. 2763, vol. 8, No. 4, p. a477.

Eynon EE, et al., Small B cells as antigen-presenting cells in the induction of tolerance to soluble protein antigens, *J Exp Med.* 1992, 175(1):131-8.

Fanslow WC et al., "Soluble forms of CD40 inhibit biologic responses of human B cells," *J Immunol.*, 1992 149(2):655-60.

Foy et al., "In vivo CD40-gp39 interactions are essential for thymus-dependent humoral immunity. II. Prolonged suppression of the humoral immune response by an antibody to the ligand for CD40, gp39," *J Exp Med.*, 1993, 178(5):1567-75.

Foy et al., "gp39-CD40 interactions are essential for germinal center formation and the development of B cell memory," *J Exp Med.*, 1994, 180(1):157-63.

French DL, et al., "The molecular and biochemical characterization of mutant monoclonal antibodies with increased antigen binding," *J Immunol*, 1991, 146: 2010-6.

Friedman SM, et al., "Human helper-T-cell function does not require T4 antigen expression," *Cell Immunol*, 1986, 103: 105-19.

Galy AH, et al., "CD40 is functionally expressed on human thymic epithelial cells," *J Immunol*, 1992, 149: 775-82.

Gordon J, et al., "Resting B lymphocytes can be triggered directly through the CDw40 (Bp50) antigen. A comparison with IL-4-mediated signaling," *J Immunol*, 1988, 140: 1425-30.

Gray D et al., "Memory B cell development but not germinal center formation is impaired by in vivo blockade of CD40-CD40 ligand interaction," *J Exp Med.*, 1994, 180(1):141-55.

Gruber MF, et al., "Anti-CD45 inhibition of human B cell proliferation depends on the nature of activation signals and the state of B cell activation. A study with anti-IgM and anti-CDw40 antibodies," *J Immunol*, 1989, 142: 4144-52.

Grusby MJ, et al., "Depletion of CD4+ T cells in major histocompatibility complex class II-deficient mice," *Science*, 1991, 253: 1417-20.

Harris, "Therapeutic antibodies- the coming of age," Tibtech, 1993, 11:42-44.

Hirohata S, et al., "T cell-dependent activation of B cell proliferation and differentiation by immobilized monoclonal antibodies to CD3," *J Immunol*, 1988, 140: 3736-44.

Hodgkin PD, et al., "Separation of events mediating B cell proliferation and Ig production by using T cell membranes and lymphokines," *J Immunol*, 1990, 145: 2025-34.

Hollenbaugh D, et al., "The human T cell antigen gp39, a member of the TNF gene family, is a ligand for the CD40 receptor: expression of a soluble form of gp39 with B cell co-stimulatory activity," *Embo J*, 1992, 11: 4313-21.

Hollenbaugh D, et al., "The role of CD40 and its ligand in the regulation of the immune response," *Immunol Rev*, 1994, 138: 23-37.

Janeway CA, Jr., et al., "CD4+ T cells: specificity and function," *Immunol. Rev.*, 1988, 101: 39-80.

Jones ST et al., "Rapid PCR-cloning of full-length mouse immunoglobulin variable regions," Biotechnology, Jun. 1991;9(6):579.

Jones B, et al., "Cooperative interaction of B lymphocytes with antigen-specific helper T lymphocytes is MHC restricted," *Nature*, 1981, 292: 547-9.

Jones PT, et al., "Replacing the complementarity-determining regions in a human antibody with those from a mouse,"*Nature*, 1986, 321: 522-5.

Jover JA, et al., "T helper cell-induced CD23 (BLAST-2) expression: an activation marker for the high density fraction of human B cells," *Clin Immunol Immunopathol*, 1989, 53: 99-112.

Julius et al., "T helper cell-dependent induction of resting B cell differentiation need not require cognate cell interactions," *Eur. J. Immunol.*, 1982, 18;375.

Katz DH, et al., "Cell interactions between histoincompatible T and B lymphocytes. The H-2 gene complex determines successful physiologic lymphocyte interactions," *Proc Natl Acad Sci U S A*, 1973, 70: 2624-8.

King et al., "Expression, purification and characterization of a mouse-human chimeric antibody and chimeric antibody and chimeric Fab' fragment," *Biochem. J.*, 1993, 290:723-9.

King et al., "Expression purification and characterization of B72.3 Fv fragments," *Biochem J*, 1993, 290:723-9.

Kirk A., et al., "Treatment with humanized monoclonal antibody against CD154 prevents acute renal allograft rejection in nonhuman primates," *Nature Medicine*, 1999, 5(6):686-92.

Korthauer U, et al., "Defective expression of T-cell CD40 ligand causes X-linked immunodeficiency with hyper-IgM," *Nature*, 1993, 361: 539-41.

Krusemeier M, et al., "Induction of lymphokine responsiveness of hapten-specific B lymphocytes promoted through an antigen-mediated T helper lymphocyte interaction," *J Immunol*, 1988, 140: 367-75.

Kubota E, et al., "Role of T cells in the B-cell response: glutaraldehyde-fixed T-helper hybridoma cells synergize with the lymphokine IL-4 to induce B-cell activation and proliferation," *Immunology*, 1991, 72: 40-7.

Kupfer A, et al., "The specific direct interaction of helper T cells and antigen-presenting B cells. II. Reorientation of the microtubule organizing center and reorganization of the membrane-associated cytoskeleton inside the bound helper T cells," *J Exp Med*, 1987, 165: 1565-80.

Kupfer A, et al., "Cell biology of cytotoxic and helper T cell functions: immunofluorescence microscopic studies of single cells and cell couples," *Annu. Rev. Immunol.*, 1987, 7;309.

Lane P, et al., "Activated human T cells express a ligand for the human B cell-associated antigen CD40 which participates in T cell-dependent activation of B lymphocytes," *Eur J Immunol*, 1992, 22: 2573-8.

Larsen CP, et al., "CD40-gp39 interactions play a critical role during allograft rejection. Suppression of allograft rejection by blockade of the CD40-gp39 pathway," *Transplantation*, 1996, 61(1):4-9.

Lederman S, et al., "Identification of a novel surface protein on activated CD4+ T cells that induces contact-dependent B cell differentiation (help)," *J Exp Med*, 1992, 175: 1091-101.

Lederman S, et al., "Molecular interactions mediating T-B lymphocyte collaboration in human lymphoid follicles. Roles of T cell-B-activating molecule (5c8 antigen) and CD40 in contact-dependent help," *J Immunol*, 1992, 149: 3817-26.

Lenschow DJ, et al., "Long-term survival of xenogeneic pancreatic islet grafts induced by CTLA4Ig," *Science*, 1992, 257(5071):789-92.

Lin H, et al., "Long-term acceptance of major histocompatibility complex mismatched cardiac allografts induced by CTLA4Ig plus donor-specific transfusion," *J Exp Med.*, 1993, 178(5):1801-6.

Linsley et al., "Immunosuppression in vivo by a soluble form of the CTLA-4 T cell activation molecule," *Science*, 1992, 257(5071):792-5.

Marshall et al., J. Clin. Immunology, 1993, 3(3):165-173.

Martinez et al., Nature, 290:60 (1981).

Martenson RE, "Myellin Basic Protein Speciation" in *Experimental Allergic Encephalomyelitis: A Useful Model for Multiple Sclerosis*, pp. 511-521 (Alan R. Liss, Inc., NY, 1984).

Mathison JC, et al., "In vivo interaction of bacterial lipopolysaccharide (LPS) with rabbit platelets: modulation by C3 and high density lipoproteins," J Immunol. 1981, 126(4):1575-80.

McCune et al., "The SCID-hu mouse: Murine model for the analysis fo human hematolymphoid differentiation and function," *Science*, 1988, 241:1632.

Mitchell GF, et al., "Cell to cell interaction in the immune response. II. The source of hemolysin-forming cells in irradiated mice given bone marrow and thymus or thoracic duct lymphocytes," *J Exp Med*, 1968, 128: 821-37.

Mitchison NA, "The carrier effect in the secondary response to hapten-protein conjugates. II. Cellular cooperation," *Eur J Immunol*, 1971, 1: 18-27.

Mitchison NA, "The carrier effect in the secondary response to hapten-protein conjugates. V. Use of antilymphocyte serum to deplete animals of helper cells," *Eur J Immunol*, 1971, 1: 68-75.

Mohan C, et al., "Long-term benefits of a brief anti-GP39 therapy in murine lupus," Arthritis and Rheumatism, 1994, 39(Suppl):S369 (#1248).

Monaco, Immunomethods, 1993, 2:159-170.

Morrison SL, et al., "Chimeric human antibody molecules: mouse antigen-binding domains with human constant region domains," *Proc Natl Acad Sci U S A*, 1984, 81:6851-5.

Morrison and Oi, "Genetically engineered antibody molegules," *Adv. Immunol.*, 1988, 44:65.

Nishimura Y, et al., "Recombinant human-mouse chimeric monoclonal antibody specific for common acute lymphocytic leukemia antigen," *Cancer Res*, 1987, 47: 999-1005.

Nishioka et al., "The role of CD40-CD40 ligand interaction interaction in human T cell-B cell collaboration," J. Immunol., 1994, 153:1027.

Noelle RJ, et al., "T helper cells," Curr Op. Immunol., 1992, 4:333-337.

Noelle RJ, et al., "Cognate interactions between helper T cells and B cells. III. Contact-dependent, lymphokine-independent induction of B cell cycle entry by activated helper T cells," *J Immunol*, 1989, 143: 1807-14.

Noelle RJ, et al., "Cognate interactions between helper T cells and B cells," *Immunol Today*, 1990, 11: 361-8.

Noelle RJ, et al., "T helper cell-dependent B cell activation," *Faseb J*, 1991, 5: 2770-6.

Noelle RJ, et al., "Cognate interactions between helper T cells and B cells. V. Reconstitution of T helper cell function using purified plasma membranes from activated Th1 and Th2 helper cells and lymphokines," *J Immunol*, 1991, 146: 1118-24.

Noelle RJ, et al., "A 39-kDa protein on activated helper T cells CD40 and transduces the signal for cognate activation of B cells," *Proc Natl Acad Sci U S A*, 1992, 89: 6550-4.

O'Brien RL, et al., "B cells expressing Ig transgenes respond to T-dependent antigen only in the presence of Ia-compatible T cells," *J Immunol*, 1988, 141: 3335-41.

Padlan EA, "A possible procedure for reducing the immunogenicity of antibody variable domains while preserving their ligand-binding properties," *Mol Immunol*, 1991, 28: 489-98.

Padlan EA, "Anatomy of the antibody molecule," *Mol Immunol*, 1994, 31: 169-217.

Page et al., "High level expression of the humanized monoclonal antibody campath-1H in Chinese hamster ovary cells," *Biol. Technology*, 1991, 9:64.

Berzofsky and Berkower, Immunogenicity and Antigen Structure, in *Fundamental Immunology*, 3rd ed., Raven Press, NY, 1993, p. 242 only.

Paulie et al., "The human B lymphocyte and carcinoma antigen, CDw40, is a phosphoprotein involved in growth signal transduction," J Immunol., 1989, 142(2):590-5.

Pollok KE, et al., "The development of competence in resting B cells. The induction of cyclic AMP and ornithine decarboxylase activity after direct contact between B and T helper cells," *J Immunol*, 1991, 146: 1633-41.

Poo WJ, et al., "Receptor-directed focusing of lymphokine release by helper T cells," *Nature*, 1988, 332: 378-80.

Press Release from Biogen, Inc., "Biogen says it has halted several trials of anti-CD40 ligand monoclonal antibody," PR Newswire, Oct. 21, 1999.

Press Release from Biogen, Inc., "Biogen says it has stopped ongoing trials of anti-CD40 ligand monoclonal antibody," PR Newswire, Nov. 2, 1999.

Press Release from IDEC Pharmaceuticals, Inc., Apr. 20, 2000.

Pulito VL, et al., "Humanization and molecular modeling of the anti-CD4 monoclonal antibody, OKT4A," *J Immunol.*, 1996, 156(8):2840-50. (2840 only).

Queen C, et al., "A humanized antibody that binds to the interleukin 2 receptor," *Proc Natl Acad Sci U S A*, 1989, 86: 10029-33.

Raff MC, "Role of thymus-derived lymphocytes in the secondary humoral immune response in mice," *Nature*, 1970, 226: 1257-8.

Rahemtulla A, et al., "Normal development and function of CD8+ cells but markedly decreased helper cell activity in mice lacking CD4," *Nature*, 1991, 353: 180-4.

Ranheim EA, et al., "Activated T cells induce expression of B7/BB1 on normal or leukemic B cells through a CD40-dependent signal," *J Exp Med.*, 1993, 177(4):925-35.

Reff, et al., "Depletion of B cells in vivo by a chimeric mouse human monoclonal antibody to CD20," *Blood*, 1994, 83:425.

Reinherz EL, et al., "Separation of functional subsets of human T cells by a monoclonal antibody," *Proc Natl Acad Sci U S A*, 1979, 76: 4061-5.

Resetkova E, et al., "Antibody to gp39, the ligand for CD40 significantly inhibits the humoral response from Graves' thyroid tissues xenografted into severe combined immunodeficient (SCID) mice," *Thyroid*, Aug. 1996;6(4):267-73.

Riechmann L, et al., "Reshaping human antibodies for therapy," *Nature*, 1988, 332: 323-7.

Rogozinski L, et al., "The T4 surface antigen is involved in the induction of helper function," *J Immunol*, 1984, 132: 735-9.

Rossini A A, et al., "Induction of immunological tolerance to islet allografts," *Cell Transplant.*, 1996, 5(1):49-52.

Roy M, et al., "The regulation of the expression of gp39, the CD40 ligand, on normal and cloned CD4+ T cells," *J Immunol*, 1993, 151: 2497-510.

Sanders VM, et al., "Characterization of the physical interaction between antigen-specific B and T cells," *J Immunol*, 1986, 137: 2395-404.

Saragovi et al., "Design and synthesis of a mimetic from an antibody complementarity-determining region," *Science*, 1991, 253:792-5.

Seachrist L., "Biogen halts trials of antova after reporting adverse events," *Bioworld Today*, Oct. 25, 1999, 10(204):1,3.

Sekita K, et al., "B cell-stimulating activity of lymphoid cell membrane fractions," *Eur J Immunol*, 1988, 18: 1405-10.

Sharabi Y, et al., Mixed chimerism and permanent specific transplantation tolerance induced by a nonlethal preparative regimen, *J Exp Med.*, 1989, 169(2):493-502.

Sharkey RM, et al., "Evaluation of a complementary-determining region-grafted (humanized) anti-carcinoembryonic antigen monoclonal antibody in preclinical and clinical studies," *Cancer Res.*, 1995, 55(23 Suppl):5935s-5945s.

Singer et al., "Optimal humanization of 1B4, an anti-CD18 murine monoclonal antibody, is achieved by correct choice of human V-region framework sequences," *J. Immunol.*, 1993, 150:2844-57.

Snow et al., "Activation of antigen-enriched B cells. II. Role of linked recognition in B cell proliferation to thymus-dependent antigens," *J. Immunol.*, 1983, 130:614.

Sprent J, "Restricted helper function of F1 hybrid T cells positively selected to heterologous erythrocytes in irradiated parental strain mice. II. Evidence for restrictions affecting helper cell induction and T-B collaboration, both mapping to the K-end of the H-2 complex," *J Exp Med*, 1978, 147: 1159-74.

Sprent J, "Role of H-2 gene products in the function of T helper cells from normal and chimeric mice in vivo," *Immunol Rev*, 1978, 42: 108-37.

Spriggs MK, et al., "Recombinant human CD40 ligand stimulates B cell proliferation and immunoglobulin E secretion," *J Exp Med*, 1992, 176: 1543-50.

Stamenkovic I, et al., "A B-lymphocyte activation molecule related to the nerve growth factor receptor and induced by cytokines in carcinomas," *Embo J*, 1989, 8: 1403-10.

Stuber E, et al., "Blocking the CD40L-CD40 interaction in vivo specifically prevents the priming of T helper 1 cells through the inhibition of interleukin 12 secretion," *J Exp Med.*, 1996, 183(2):693-8.

Tisch R, et al. "Antigen-specific immunotherapy: is it a real possibility to combat T-cell-mediated autoimmunity?" *Pro Natl Acad Sci U S A*, 1994, 91(2):437-8.

Thompson CB, et al., "T cell-derived B cell growth factor(s) can induce stimulation of both resting and activated B cells," *J. Immunol*, 1985, 134: 369-74.

Thorbecke GJ, et al., "Involvement of endogenous tumor necrosis factor alpha and transforming growth factor beta during induction of collagen type II arthritis in mice," *Proc Natl Acad Sci U S A*, 1992, 89: 7375-9.

Tohma S, et al., "Analysis of the mechanisms of T cell-dependent polyclonal activation of human B cells. Induction of human B cell responses by fixed activated T cells," *J Immunol*, 1991, 146: 2544-52.

Tohma S, et al., "The role of CD11a/CD18-CD54 interactions in human T cell-dependent B cell activation," *J Immunol.*, 1991, 146(2):492-9.

Trentham DE, et al., "Autoimmunity to type II collagen an experimental model of arthritis," *J Exp Med*, 1977, 146: 857-68.

Turka LA, et al., "T-cell activation by the CD28 ligand B7 is required for cardiac allograft rejection in vivo," *Proc Natl Acad Sci U S A*, 1992, 89(22):11102-5.

Valle A, et al., "Activation of human B lymphocytes through CD40 and interleukin 4," *Eur J Immunol*, 1989, 19: 1463-7.

Van der Eetwegh et al., "In vivo CD40-gp39 interactions are essential for thymus-dependent humoral Immunity. I. In vivo expression of CD40 ligand, cytokines, and antibody production delineates sites of cognate T-B cell interactions," *J. Exp. Med.*, 1993, 178:1555.

Verhoeyen et al., "Reshaping human antibodies: grafting an antilysozyme activity," *Science*, 1988, 239:1539.

Vitetta ES, et al., "Cellular interactions in the humoral immune response," *Adv Immunol*, 1989, 45: 1-105.

Waldmann H, "Manipulation of T-cell responses with monoclonal antibodies," *Annu. Rev. Immunol.*, 1989, 7:407-444.

Waldmann TA, Immune receptors: targets for therapy of leukemia/lymphoma, autoimmune diseases and for the prevention of allograft rejection, *Annu. Rev. Immuno.*, 1992, 10:675-704.

Waldmann TA, "Monoclonal antibodies in diagnosis and therapy," *Science*, 1991, 152:1657-1662.

Watson et al., "Recombinant DNA," 2nd Ed., Scientif. Ameri. Books, NY, NY (1992).

Wee S, et al., "Anti-CD4 mAb therapy significantly delays the alloantibody response in a cynomolgus renal transplant model," *Transplantation*, 1994, 58(2):261-4.

Whalen BJ, et al., "Characterization of the effector mechanism of help for antigen-presenting and bystander resting B cell growth mediated by Ia-restricted Th2 helper T cell lines," *J Immunol*, 1988, 141: 2230-9.

White et al., "T-lymphocyte heterogeneity in the rat: separation of functional subpopulations using a monoclonal antibody," *J Exp Med.,* 1978, 14:664.

Yellin MJ et al., "A human CD4- T cell leukemia subclone with contact-dependent helper function" J. Immunol., 1991, 147:3389-3395.

Zamvill SS, et al., "The T lymphocyte in experimental allergic encephalomyelitis," *Annu Rev Immunol.,* 1990, 8:579.

Zinkemagel RM, "T helpers may be sensitized by antigen-specifically altered structures, which are coded by the I region of the H-2 gene complex," *Adv. Exp Med Biol,* 1976, 66: 527-30.

* cited by examiner 24-31 Humanized V_L #1

```
     BglII        9             18            27            36            45            54
5'  AGA TCT  CTC ACC | ATG GGC  TTC AAG  ATG GAG  TCA CAG  TTT CTG  GCC TTT  GTA TTC
    --- ---  --- ---   --- ---  --- ---  --- ---  --- ---  --- ---  --- ---  --- ---
                       M   G    F   K    M   E    S   Q    F   L    A   F    V   F 63            72            81       FR1 90            99           108
    GCG TTT  CTC TGG  TTG TCT  GGT GTT  GAT GGA | GAC ATT  GTG ATG  ACC CAG  TCT CCA
    --- ---  --- ---  --- ---  --- ---  --- ---   --- ---  --- ---  --- ---  --- ---
    A   F    L   W    L   S    G   V    D   G     D   I    V   M    T   Q    S   P 117           126           135           144          153 CDR1      162
    TCT TTC  CTC TCC  GCC TCC  GTA GGA  GAC AGG  GTC ACC  ATC ACC  TGC | AAG GCC  AGT
    --- ---  --- ---  --- ---  --- ---  --- ---  --- ---  --- ---        --- ---  ---
    S   F    L   S    A   S    V   G    D   R    V   T    I   T    C     K   A    S 171           180          189 FR2     198           207           216
    CAG AAT  GTG ATT  ACT GCT  GTA GCC | TGG TAT  CAA CAG  AAA CCA  GGA AAG  TCT CCT
    --- ---  --- ---  --- ---  --- ---   --- ---  --- ---  --- ---  --- ---  --- ---
    Q   N    V   I    T   A    V   A     W   Y    Q   Q    K   P    G   K    S   P 225          234 CDR2     243           252 FR3     261           270
    AAA TTG  CTG ATT  TAC | TCG GCA  TCC AAT  CGG TAC  ACT | GGA GTC  CCT GAT  CGC TTC
    --- ---  --- ---  ---   --- ---  --- ---  --- ---  ---   --- ---  --- ---  --- ---
    K   L    L   I    Y     S   A    S   N    R   Y    T     G   V    P   D    R   F 279           288           297           306           315           324
    TCA GGC  AGT GGG  TCT GGG  ACA GAT  TTC ACT  CTC ACC  ATC AGC  TCT CTC  CAG CCA
    --- ---  --- ---  --- ---  --- ---  --- ---  --- ---  --- ---  --- ---  --- ---
    S   G    S   G    S   G    T   D    F   T    L   T    I   S    S   L    Q   P 333           342           351 CDR3    360           369          378
    GAA GAC  TTC GCA  GAT TAT  TTC TGC | CAG CAA  TAT AAC  AGC TAT  CCG TAC  ACG | TTC
    --- ---  --- ---  --- ---  --- ---   --- ---  --- ---  --- ---  --- ---  ---   ---
    E   D    F   A    D   Y    F   C     Q   Q    Y   N    S   Y    P   Y    T     F

FR4 387           396           405  BsiWI
    GGA GGG  GGG ACC  AAG CTG  GAA ATC  AAA  CGT ACG  3'
    --- ---  --- ---  --- ---  --- ---  ---  --- ---
    G   G    G   T    K   L    E   I    K    R   T
```

FIG. 4

24-31 Humanized $V_L$ #2

```
     BglII       9              18              27              36              45              54
5' AGA TCT CTC ACC ATG GGC TTC AAG ATG GAG TCA CAG TTT CTG GCC TTT GTA TTC
   --- --- --- --- --- --- --- --- --- --- --- --- --- --- --- --- --- ---
                   M   G   F   K   M   E   S   Q   F   L   A   F   V   F 63              72              81              90  FR1         99             108
   GCG TTT CTC TGG TTG TCT GGT GTT GAT GGA GAC ATT GTG ATG ACC CAG TCT CCA
   --- --- --- --- --- --- --- --- --- --- --- --- --- --- --- --- --- ---
    A   F   L   W   L   S   G   V   D   G   D   I   V   M   T   Q   S   P 117             126             135             144             153  CDR1        162
   GAT TCT CTC GCC GTG TCC CTC GGA GAG AGG GCC ACC ATC AAC TGC AAG GCC AGT
   --- --- --- --- --- --- --- --- --- --- --- --- --- --- --- --- --- ---
    D   S   L   A   V   S   L   G   E   R   A   T   I   N   C   K   A   S 171             180             189  FR2        198             207             216
   CAG AAT GTG ATT ACT GCT GTA GCC TGG TAT CAA CAG AAA CCA GGA CAA TCT CCT
   --- --- --- --- --- --- --- --- --- --- --- --- --- --- --- --- --- ---
    Q   N   V   I   T   A   V   A   W   Y   Q   Q   K   P   G   Q   S   P 225             234  CDR2       243             252  FR3        261             270
   AAA TTG CTG ATT TAC TCG GCA TCC AAT CGG TAC ACT GGA GTC CCT GAT CGC TTC
   --- --- --- --- --- --- --- --- --- --- --- --- --- --- --- --- --- ---
    K   L   L   I   Y   S   A   S   N   R   Y   T   G   V   P   D   R   F 279             288             297             306             315             324
   TCA GGC AGT GGG TCT GGG ACA GAT TTC ACT CTC ACC ATC AGC TCT CTC CAG GCC
   --- --- --- --- --- --- --- --- --- --- --- --- --- --- --- --- --- ---
    S   G   S   G   S   G   T   D   F   T   L   T   I   S   S   L   Q   A 333             342             351  CDR3       360             369             378
   GAA GAC GTG GCA GAT TAT TTC TGC CAG CAA TAT AAC AGC TAT CCG TAC ACG TTC
   --- --- --- --- --- --- --- --- --- --- --- --- --- --- --- --- --- ---
    E   D   V   A   D   Y   F   C   Q   Q   Y   N   S   Y   P   Y   T   F

FR4    387             396             405  BsiWI
   GGA GGG GGG ACC AAG CTG GAA ATC AAA CGT ACG 3'
   --- --- --- --- --- --- --- --- --- --- ---
    G   G   G   T   K   L   E   I   K   R   T
```

FIG. 5

24-31 Humanized V_H #1

```
     SalI     9              18              27              36              45              54
5' GTC GAC ATG ATG GTG TTA AGT CTT CTG TAC CTG TTG ACA GCC CTT CCG GGT TTC
           M   M   V   L   S   L   L   Y   L   L   T   A   L   P   G   F

63  FR1   72              81              90              99             108
   CTG TCA GAG GTG CAG CTT CAG GAG TCA GGA CCT GGC CTC GTG AAA CCT TCT GAG
    L   S   E   V   Q   L   Q   E   S   G   P   G   L   V   K   P   S   E 117             126             135             144             153 CDR1      162
   ACT CTG TCC CTC ACC TGT ACC GTC TCT GGC GAC TCC ATC ACT AAT GGT TTC TGG
    T   L   S   L   T   C   T   V   S   G   D   S   I   T   N   G   F   W

171 FR2     180             189             198             207 CDR2       216
   ATC TGG ATC CGG AAA CCA CCA GGG AAT AAA CTT GAG TAC ATG GGC TAC ATA AGT
    I   W   I   R   K   P   P   G   N   K   L   E   Y   M   G   Y   I   S 225             234             243             252             261 FR3       270
   TAC AGT GGT AGC ACT TAC TAC AAT CCA TCT CTC AAG AGT CGA ATC TCC ATC TCT
    Y   S   G   S   T   Y   Y   N   P   S   L   K   S   R   I   S   I   S 279             288             297             306             315             324
   CGC GAC ACA TCC AAG AAC CAG TTC TCT CTA AAG TTG TCT TCT GTG ACT GCC GCC
    R   D   T   S   K   N   Q   F   S   L   K   L   S   S   V   T   A   A 333             342             351 CDR3      360             369             378
   GAC ACA GGC GTG TAT TAC TGT GCC TGC CGC AGT TAC GGG AGG ACC CCG TAC TAC
    D   T   G   V   Y   Y   C   A   C   R   S   Y   G   R   T   P   Y   Y
                                                                   NheI
          387 FR4     396             405             414           423
   TTT GAC TTC TGG GGC CAA GGC ACC ACT CTC ACC GTC TCC TCA GCT AGC 3'
    F   D   F   W   G   Q   G   T   T   L   T   V   S   S   A   S
```

FIG. 6

Anti-gp39 24-31 V$_K$ Sequence

```
     Bgl II    9              18              27              36              45              54
5' AGA TCT CTC ACC ATG GGC TTC AAG ATG GAG TCA CAG TTT CTG GCC TTT GTA TTC
   --- --- --- --- --- --- --- --- --- --- --- --- --- --- --- --- --- ---
                    M   G   F   K   M   E   S   Q   F   L   A   F   V   F 63              72              81    +1  90  FRI   99             108
   GCG TTT CTC TGG TTG TCT GGT GTT GAT GGA GAC ATT GTG ATG ACC CAG TCT CAA
   --- --- --- --- --- --- --- --- --- --- --- --- --- --- --- --- --- ---
    A   F   L   W   L   S   G   V   D   G   D   I   V   M   T   Q   S   Q 117             126             135             144            153  CDR1 162
   AAA TTC ATG TCC ACA TCC GTA GGA GAC AGG GTC AGC ATC ACC TGC AAG GCC AGT
   --- --- --- --- --- --- --- --- --- --- --- --- --- --- --- --- --- ---
    K   F   M   S   T   S   V   G   D   R   V   S   I   T   C   K   A   S 171             180            189  FR2  198             207             216
   CAG AAT GTG ATT ACT GCT GTA GCC TGG TAT CAA CAG AAA CCA GGA CAA TCT CCT
   --- --- --- --- --- --- --- --- --- --- --- --- --- --- --- --- --- ---
    Q   N   V   I   T   A   V   A   W   Y   Q   Q   K   P   G   Q   S   P 225            234  CDR2  243             252  FR3  261             270
   AAA TTG CTG ATT TAC TCG GCA TCC AAT CGG TAC ACT GGA GTC CCT GAT CGC TTC
   --- --- --- --- --- --- --- --- --- --- --- --- --- --- --- --- --- ---
    K   L   L   I   Y   S   A   S   N   R   Y   T   G   V   P   D   R   F 279             288             297             306             315             324
   TCA GGC AGT GGG TCT GGG ACA GAT TTC ACT CTC ACC ATC AGC AAT ATG CAG TCT
   --- --- --- --- --- --- --- --- --- --- --- --- --- --- --- --- --- ---
    S   G   S   G   S   G   T   D   F   T   L   T   I   S   N   M   Q   S 333             342            351  CDR3  360             369             378
   GAA GAC CTG GCA GAT TAT TTC TGC CAG CAA TAT AAC AGC TAT CCG TAC ACG TTC
   --- --- --- --- --- --- --- --- --- --- --- --- --- --- --- --- --- ---
    E   D   L   A   D   Y   F   C   Q   Q   Y   N   S   Y   P   Y   T   F

FR4  387             396             405  Bsi WI
   GGA GGG GGG ACC AAG CTG GAA ATC AAA CGT ACG 3'
   --- --- --- --- --- --- --- --- --- --- ---
    G   G   G   T   K   L   E   I   K   R   T
```

FIG. 7

Anti-gp39 24-31 V$_H$ Sequence

```
      SalI          9              18              27              36              45              54
5' GTC GAC ATG ATG GTG TTA AGT CTT CTG TAC CTG TTG ACA GCC CTT CCG GGT TTC
   --- --- --- --- --- --- --- --- --- --- --- --- --- --- --- --- --- ---
            M   M   V   L   S   L   L   Y   L   L   T   A   L   P   G   F
               +1
               63      FRI 72              81              90              99             108
CTG TCA GAG GTG CAG CTT CAG GAG TCA GGA CCT AGC CTC GTG AAA CCT TCT CAG
--- --- --- --- --- --- --- --- --- --- --- --- --- --- --- --- --- ---
 L   S   E   V   Q   L   Q   E   S   G   P   S   L   V   K   P   S   Q 117             126             135             144             153 CDR1       162
ACT CTG TCC CTC ACC TGT TCT GTC ACT GGC GAC TCC ATC ACT AAT GGT TTC TGG
--- --- --- --- --- --- --- --- --- --- --- --- --- --- --- --- --- ---
 T   L   S   L   T   C   S   V   T   G   D   S   I   T   N   G   F   W

171 FR2         180             189             198             207  CDR2  216
ATC TGG ATC CGG AAA TTC CCA GGG AAT AAA CTT GAG TAC ATG GGC TAC ATA AGT
--- --- --- --- --- --- --- --- --- --- --- --- --- --- --- --- --- ---
 I   W   I   R   K   F   P   G   N   K   L   E   Y   M   G   Y   I   S
                                                                        FR3
           225             234             243             252             261        270
TAC AGT GGT AGC ACT TAC TAC AAT CCA TCT CTC AAG AGT CGA ATC TCC ATC ACT
--- --- --- --- --- --- --- --- --- --- --- --- --- --- --- --- --- ---
 Y   S   G   S   T   Y   Y   N   P   S   L   K   S   R   I   S   I   T 279             288             297             306             315             324
CGC GAC ACA TCC CAG AAC CAG TTC TAC CTA CAA TTG AAT TCT GTG ACT ACT GAG
--- --- --- --- --- --- --- --- --- --- --- --- --- --- --- --- --- ---
 R   D   T   S   Q   N   Q   F   Y   L   Q   L   N   S   V   T   T   E 333             342             351 CDR3       360             369             378
GAC ACA GGC ACA TAT TAC TGT GCC TGC CGC AGT TAC GGG AGG ACC CCG TAC TAC
--- --- --- --- --- --- --- --- --- --- --- --- --- --- --- --- --- ---
 D   T   G   T   Y   Y   C   A   C   R   S   Y   G   R   T   P   Y   Y

387  FR4        396             405             414           423 NheI
TTT GAC TTC TGG GGC CAA GGC ACC ACT CTC ACC GTC TCC TCA GCT AGC 3'
--- --- --- --- --- --- --- --- --- --- --- --- --- --- --- --- ---
 F   D   F   W   G   Q   G   T   T   L   T   V   S   S   A   S
```

FIG. 8

TREATING AUTOIMMUNE DISEASES WITH HUMANIZED ANTI-CD40L ANTIBODY

CROSS-REFERENCE TO RELATED APPLICATION

This is a continuation of U.S. patent application Ser. No. 08/925,339 filed Sep. 8, 1997, which issued as U.S. Pat. No. 6,440,418 on Aug. 27, 2003, and which is a continuation-in-part of U.S. patent application Ser. No. 08/554,840, filed Nov. 7, 1995, which issued as U.S. Pat. No. 6,001,358 on Dec. 14, 1999.

FIELD OF THE INVENTION

The present invention is directed to humanized antibodies specific for human gp39, DNA encoding such antibodies, methods for their production, pharmaceutical compositions containing, and the use of such humanized antibodies as therapeutic agents. These antibodies have particular application in the treatment of autoimmune diseases including, e.g., rheumatoid arthritis, multiple sclerosis, diabetes, and systemic lupus erythematosus as well as non-autoimmune diseases including, e.g., graft-versus-host disease and for preventing graft rejection.

BACKGROUND OF THE INVENTION

The immune system is capable of producing two types of antigen-specific responses to foreign antigens. Cell-mediated immunity is the term used to refer to effector functions of the immune system mediated by T lymphocytes. Humoral immunity is the term used to refer to production of antigen-specific antibodies by B lymphocytes. It has long been appreciated that the development of humoral immunity against most antigens requires not only antibody-producing B lymphocytes but also the involvement of helper T (hereinafter Th) lymphocytes. (Mitchison, *Eur. J. Immunol.*, 1:18–25 (1971); Claman and Chaperon, *Transplant Rev.*, 1:92–119 (1969); Katz et al, *Proc. Natl. Acad. Sci. USA*, 70:2624–2629 (1973); Reff et al, *Nature*, 226:1257–1260 (1970)). Certain signals, or "help", are provided by Th cells in response to stimulation by Thymus-dependent (hereinafter TD) antigens. While some B lymphocyte help is mediated by soluble molecules released by Th cells (for instance lymphokines such as IL-4 and IL-5), activation of B cells also requires a contact-dependent interaction between B cells and Th cells. (Hirohata et al, *J. Immunol.*, 140:3736–3744 (1988); Bartlett et al, *J. Immunol.*, 143: 1745–1765 (1989)). This indicates that B cell activation involves an obligatory interaction between cell surface molecules on B cells and Th cells. Such an interaction is further supported by the observation that isolated plasma membranes of activated T cells can provide helper functions necessary for B cell activation. (Brian, *Proc. Natl. Acad. Sci. USA*, 85:564–568 (1988); Hodgkin et al, *J. Immunol.*, 145: 2025–2034 (1990); Noelle et al, *J. Immunol.*, 20 146: 1118–1124 (1991)).

It is further known that in a contact-dependent process termed "T cell helper function", $CD4^+$ T lymphocytes direct the activation and differentiation of B lymphocytes and thereby regulate the humoral immune response by modulating the specificity, secretion and isotype-encoded functions of antibody molecules (Mitchell et al, *J. Exp. Med.*, 128:821 (1968); Mitchison, *Eur. J. Immunol.*, 1:68 (1971); White et al, *J. Exp. Med.*, 14:664 (1978); Reinherz et al, *Proc. Natl. Acad. Sci. USA*, 74:4061 (1979); Janeway et al, *Immunol. Rev.*, 101:39 (1988); O'Brien et al, *J. Immunol.*, 141:3335 (1988); Rahemtulla et al, *Nature*, 353:180 (1991); and Grusby et al, *Science*, 253:1417 (1991)).

The process by which T cells help B cells to differentiate has been divided into two distinct phases; the inductive and effector phases (Vitetta et al, *Adv. Immunol.*, 45:1 (1989); Noelle et al, *Immunol. Today*, 11:361 (1990)). In the inductive phase, resting T cells contact antigen-primed B cells and this association allows clonotypic T cell receptor (TCR)-CD4 complexes to interact with Ia/Ag complexes on B cells (Janeway et al, *Immunol. Rev.*, 101:39 (1988); Katz et al, *Proc. Natl. Acad. Sci.*, 70:2624 (1973); Zinkernagel, *Adv. Exp. Med.*, 66:527 (1976); Sprent, *J. Exp. Med.*, 147:1159 (1978); Sprent, *Immunol. Rev.*, 42:158 (1978); Jones et al, *Nature*, 292:547 (1981); Julius et al, *Eur. J. Immunol.*, 18:375 (1982); Chestnut et al, *J. Immunol.*, 126:1575 (1981); and Rogozinski et al, *J. Immunol.*, 126:735 (1984)). TCR/CD4 recognition of Ia/Ag results in the formation of stable T-B cognate pairs and bi-directional T and B cell activation (Sanders et al, *J. Immunol.*, 137:2395 (1986); Snow et al, *J. Immunol.*, 130:614 (1983); Krusemeier et al, *J. Immunol.*, 140:367 (1988); Noelle et al, *J. Immunol.*, 143:1807 (1989); Bartlett et al, *J. Immunol.*, 143:1745 (1989); and Kupfer et al, *Annu. Rev. Immunol.*, 7:309 (1987)). In the effector phase, activated T cells drive B cell differentiation by secreting lymphokines (Thompson et al, *J. Immunol.*, 134:369 (1985)) and by contact-dependent stimuli (Noelle et al, *J. Immunol.*, 143:1807 (1989); Clement et al, *J. Immunol.*, 140:3736 (1984); Crow et al, *J. Exp. Med.*, 164:1760 (1986); Brian, *Proc. Natl. Acad. Sci., USA*, 85:564 (1988); Hirohata et al, *J. Immunol.* 140:3736 (1988); Jover et al, *Clin. Immunol. Immun.*, 53:90 (1989); Whalen et al, *J. Immunol.*, 141:2230 (1988); Pollok et al, *J. Immunol.*, 146:1633 (1991); and Bartlett et al, *J. Immunol.*, 143:1745 (1990)), both of which are required for T cells to drive small resting B cells to terminally differentiate into Ig secreting cells (Clement et al, *J. Immunol.*, 132:740 (1984); Martinez et al, *Nature*, 290:60 (1981); and Andersson et al, *Proc. Natl. Acad. Sci., USA*, 77:1612 (1980)).

Although the inductive phase of T cell help is Ag-dependent and MHC-restricted (Janeway et al, *Immun. Rev.*, 101:34 (1988); Katz et al, *Proc. Natl. Acad. Sci., USA*, 10:2624 (1973); Zinkernagle, *Adv. Exp. Med. Biol.*, 66:527 (1976)); the effector phase of T cell helper function can be Ag-independent and MHC-nonrestricted (Clement et al, *J. Immunol.*, 132:740 (1984); Hirohata et al, *J. Immunol.*, 140:3736 (1988); Whalen et al, *J. Immunol.*, 143:1715 (1988)). An additional contrasting feature is that the inductive phase of T cell help often requires CD4 molecules and is inhibited by anti-CD4 mAb (Rogozinski et al, *J. Immunol.*, 126:735 (1984)), whereas helper effector function does not require CD4 molecules (Friedman et al, *Cell Immunol.*, 103:105 (1986)) and is not inhibited by anti-CD4 mAbs (Brian, *Proc. Natl. Acad. Sci., USA*, 85:564 (1988); Hirohata et al, *J. Immunol.*, 140:3736 (1988); Whalen et al, *J. Immunol.*, 143:1745 (1988); and Tohma et al, *J. Immunol.*, 146:2547 (1991)). The non-specific helper effector function is believed to be focused on specific B cell targets by the localized nature of the T-B cell interactions with antigen specific, cognate pairs (Bartlett et al, *J. Immunol.*, 143:1745 (1989); Kupfer et al, *J. Exp. Med.*, 165:1565 (1987) and Poo et al, *Nature*, 332:378 (1988)).

Although terminal B cell differentiation requires both contact- and lymphokine-mediated stimuli from T cells, intermediate stages of B cell differentiation can be induced by activated T cell surfaces in the absence of secreted factors (Crow et al, *J. Exp. Med.*, 164:1760 (1986); Brian, *Proc.*

Natl. Acad. Sci., USA, 85:564 (1988); Sekita et al, *Eur. J. Immunol.*, 18:1405 (1988); Hodgkin et al, *J. Immunol.*, 145:2025 (1990); Noelle et al, *FASEB J*, 5:2770 (1991)). These intermediate effects on B cells include induction of surface CD23 expression (Crow et al, *Cell Immunol.*, 121:94 (1989)), enzymes associated with cell cycle progression (Pollok et al, *J. Immunol.*, 146:1633 (1991)) and responsiveness to lymphokines (Noelle et al, *FASEB J*, 5:2770 (1989); Pollok et al, *J. Immunol.*, 146:1633 (1991)). Recently some of the activation-induced T cell surface molecules that direct B cell activation have been identified. Additionally, functional studies have characterized some features of activation-induced T cell surface molecules that direct B cell activation. First, T cells acquire the ability to stimulate B cells 4–8 h following activation (Bartlett et al, *J. Immunol.*, 145:3956 (1990) and Tohma et al, *J. Immunol.*, 146:2544 (1991)). Second, the B cell stimulatory activity associated with the surfaces of activated T cells is preserved on paraformaldehyde fixed cells (Noelle et al, *J. Immunol.*, 143:1807 (1989); Cros et al, *J. Exp. Med.*, 164:1760 (1986); Pollok et al, *J. Immunol.*, 146:1633 (1991); Tohma et al, *J. Immunol.*, 146:2544 (1991); and Kubota et al, *Immunol.*, 72:40 (1991)) and on purified membrane fragments (Hodgkin et al, *J. Immunol.*, 145:2025 (1990) and Martinez et al, *Nature*, 290:60 (1981)). Third, the B cell stimulatory activity is sensitive to protease treatment (Noelle et al, *J. Immunol.*, 143:1807 (1989); Sekita et al, *Eur. J. Immunol.*, 18:1405 (1988); and Hodgkin et al, *J. Immunol.*, 145:2025 (1990). Fourth, the process of acquiring these surface active structures following T cell activation is inhibited by cycloheximide (Tohma et al, *J. Immunol.*, 196:2349 (1991) and Hodgkin et al, *J. Immunol.*, 195:2025 (1990)).

A cell surface molecule, CD40, has been identified on immature and mature B lymphocytes which, when crosslinked by antibodies, induces B cell proliferation. Valle et al, *Eur. J. Immunol.*, 19:1463–1467 (1989); Gordon et al, *J. Immunol.*, 140:1425–1430 (1988); Gruder et al, *J. Immunol.*, 142:4144–4152 (1989).

CD40 has been molecularly cloned and characterized (Stamenkovic et al, *EMBO J.*, 8:1403–1410 (1989)).

CD40 is expressed on B cells, interdigitating dendritic cells, macrophages, follicular dendritic cells, and thymic epithelium (Clark, *Tissue Antigens* 36:33 (1990); Alderson et al, *J. Exp. Med.*, 178:669 (1993); Galy et al, *J. Immunol.* 142:772 (1992)). Human CD40 is a type I membrane protein of 50 kDa and belongs to the nerve growth factor receptor family (Hollenbaugh et al, *Immunol. Rev.*, 138:23 (1994)). Signaling through CD40 in the presence of IL-10 induces IgA, IgM and IgG production, indicating that isotype switching is regulated through these interactions. The interaction between CD40 and its ligand results in a primed state of the B cell, rendering it receptive to subsequent signals.

Also, a ligand for CD40, gp39 (also called CD40 ligand or CD40L) has recently been molecularly cloned and characterized (Armitage et al, *Nature*, 357:80–82 (1992); Lederman et al, *J. Exp. Med.*, 175:1091–1101 (1992); Hollenbaugh et al, *EMBO J.*, 11:4313–4319 (1992)). The gp39 protein is expressed on activated, but not resting, CD4$^+$ Th cells. Spriggs et al, *J. Exp. Med.*, 176:1543–1550 (1992); Lane et al, *Eur. J. Immunol.*, 22:2573–2578 (1992); and Roy et al, *J. Immunol.*, 151:1–14 (1993). Cells transfected with gp39 gene and expressing the gp39 protein on their surface can trigger B cell proliferation and, together with other stimulatory signals, can induce antibody production. Armitage et al, *Nature*, 357:80–82 (1992); and Hollenbaugh et al, *EMBO J.*, 11:4313–4319 (1992). In particular, the ligand for CD40, gp39, has been identified for the mouse (Noelle et al, *Proc. Natl. Acad. Sci. USA*, 89:6550 (1992); Armitage et al, *Nature*, 357:80 (1992)) and for humans (Hollenbaugh et al, *Embo. J.* 11:4313 (1992); Spriggs et al, *J. Exp. Met.*, 176:1543 (1992)). gp39 is a type II membrane protein and is part of a new gene super family which includes TNF-α, TNF-β and the ligands for FAS, CD27, CD30 and 4-1BB.

Expression of gp39 can be readily induced in vitro on CD4$^+$ T cells using either anti-CD3 antibody or phorbol myristate acetate (PMA) plus ionomycin. Expression is rapid and transient, peaking at 6–8 hours and returning to near resting levels between 24 and 48 hours (Roy et al, *J. Immunol.*, 151:2497 (1993)). In vivo, gp39 has been reported in humans to be present on CD4$^+$ T cells in the mantle and centrocytic zones of lymphoid follicles and the periarteriolar lymphocyte sheath of the spleen, in association with CD40$^+$ B cells (Lederman et al, *J. Immunol.*, 149:3807 (1992)). gp39$^+$ T cells produce IL-2, IL-4 and IFN-γ (Van der Eetwegh et al, *J. Exp. Med.*, 178:1555 (1993)).

Unique insights into the novel role of gp39 in the regulation of humoral immunity have been provided by studies of a human disease, X-linked hyper-IgM syndrome (HIM). HIM is a profound, X-linked immunodeficiency typified by a loss in thymus dependent humoral immunity, the inability to produce IgG, IgA and IgE. Mutations in the gp39 gene were responsible for the expression of a non-functional gp39 protein and the inability of the helper T cells from HIM patients to activate B cells (Allen et al, *Science*, 259:990 (1993); Aruffo et al, *Cell*, 72:291 (1993); DiSanto et al, *Nature*, 361:541 (1993); Korthauer et al, *Nature*, 361:539 (1993)). These studies support the conclusion that early after T cell receptor engagement of the peptide/MHC class II complex, gp39 is induced on the cognate helper T cell, and the binding of gp39 to CD40 on the B cell induces the B cell to move into the cell cycle and differentiate to immunoglobulin (Ig) secretion and isotype switching.

Functional studies have shown that treatment of mice with anti-gp39 completely abolished the antibody response against thymus dependent antigens (SRBC and TNP-KLH), but not thymus independent antigens (TNP-Ficoll) (Foy et al, *J. Exp. Med.*, 178:1567 (1993)). In addition, treatment with anti-gp39 prevented the development of collagen-induced arthritis (CIA) in mice injected with collagen (Durie et al, *Science*, 261:1328 (1993)). Finally, anti-gp39 prevented formation of memory B cells and germinal centers in mouse spleen (Foy et al, *J. Exp. Med.*, 180:157 (1994)). Collectively, these data provide extensive evidence that the interaction between gp39 on T cells and CD40 on B cells is essential for antibody responses against thymus dependent antigens.

Recently, a number of murine models of autoimmune disease have been exploited to evaluate the potential therapeutic value of anti-gp39 administration on the development of disease. A brief discussion of the results of studies in these models are provided below:

Collagen-Induced Arthritis:

CIA is an animal model for the human autoimmune disease rheumatoid arthritis (RA) (Trenthorn et al, *J. Exp. Med.*, 146:857 (1977)). This disease can be induced in many species by the administration of heterologous type II collagen (Courtenay et al, *Nature*, 283:665 (1980); Cathcart et al, *Lab. Invest.*, 54:26 (1986)).

To study the effect anti-gp39 on the induction of CIA (Durie et al, *Science*, 261:1328 (1993)) male DBA1/J mice were injected intradermally with chick type II collagen emulsified in complete Freund's adjuvant at the base of the tail. A subsequent challenge was carried out 21 days later.

Mice were then treated with the relevant control antibody or anti-gp39. Groups of mice treated with anti-gp39 showed no titers of anti-collagen antibodies compared to immunized, untreated control mice. Histological analysis indicated that mice treated with anti-gp39 antibody showed no signs of inflammation or any of the typical pathohistological manifestations of the disease observed in immunized animals. These results indicated that gp39-CD40 interactions are absolutely essential in the induction of CIA. If the initial cognate interaction between the T cell and B cell is not obtained, then the downstream processes, such as autoantibody formation and the resulting inflammatory responses, do not occur.

Recently it has been shown that gp39 is important in activating monocytes to produce TNF-$\alpha$ and IL-6 in the absence of GM-CSF, IL-3 and IFN-$\gamma$ (Alderson et al, *J. Exp. Med.*, 178:669 (1993)). TNF-$\alpha$ has been implicated in the CIA disease process (Thorbecke et al, *Eur. J. Immunol.*, 89:7375 (1992) and in RA (DiGiovane et al, *Ann. Rheum. Dis.*, 47:68 (1988); Chu et al, *Arthrit. Rheum.*, 39:1125 (1991); Brennan et al, *Eur. J. Immunol.*, 22:1907 (1992). Thus, inhibition of TNF-$\alpha$ by anti-gp39 may have profound anti-inflammatory effects in the joints of arthritic mice. Both inhibition of TNF-$\alpha$ and of T cell-B cell interactions by anti-gp39 may be contributory to manifestations of CIA.

Experimental Allergic Encephalomyelitis (EAE):

EAE is an experimental autoimmune disease of the central nervous system (CNS) (Zamvil et al, *Ann. Rev. Immunol.*, 8:579 (1990) and is a disease model for the human autoimmune condition, multiple sclerosis (MS) (Alvord et al, "Experimental Allergic Model for Multiple Sclerosis," NY 511 (1984)). It is readily induced in mammalian species by immunizations of myelin basic protein purified from the CNS or an encephalitogenic proteolipid (PLP). SJL/J mice are a susceptible strain of mice (H-$2^s$) and, upon induction of EAE, these mice develop an acute paralytic disease and an acute cellular infiltrate is identifiable within the CNS.

Classen and co-workers (unpublished data) have studied the effects of anti-gp39 on the induction of EAE in SJL/J mice. They found that EAE development was completely suppressed in the anti-gp39 treated animals. In addition, anti-PLP antibody responses were delayed and reduced compared to those obtained for control animals.

EAE is an example of a cell-mediated autoimmune disease mediated via T cells, with no direct evidence for the requirement for autoantibodies in disease progression. Interference with the interaction between gp39 and CD40 prevents disease induction and the adoptive transfer of disease. Chronic (c) and acute (a) graft-versus-host-disease (GVHD):

Chronic and acute GVHD result from donor cells responding to host disparate MHC alleles. In cGVHD (H-$2^d$→H-$2^{bd}$), heightened polyclonal immunoglobulin production is due to the interaction of allospecific helper T cells and the host B cells. In vivo administration of anti-gp39 antibody blocked cGVHD-induced serum anti-DNA autoantibodies, IgE production, spontaneous immunoglobulin production in vitro, associated splenomegaly and the ability to transfer disease Durie F. H. et al, *J. Clin. Invest.*, 94:133 (1994). Antibody production remained inhibited for extended periods of time after termination of anti-gp39 administration. Anti-allogeneic cytotoxic T lymphocyte (CTL) responses induced in GVHD were also prevented by the in vivo administration of anti-gp39. These data suggest that CD40-gp39 interactions are critical in the generation of both forms of GVHD. The fact that CTL responses were inhibited and a brief treatment with anti-gp39 resulted in long-term prevention of disease suggest permanent alterations in the T cell compartment by the co-administration of allogeneic cells and anti-gp39 antibody.

Various research groups have reported the production of murine antibodies specific to gp39, which are disclosed to possess therapeutic utility as immunosuppressants. For example, WO 93/09812, published May 27, 1993, and assigned to Columbia University; EP 0,555,880, published Aug. 18, 1993, and PCT US/94/09872, filed Sep. 2, 1994 by Noelle et al and assigned to Dartmouth College, describe murine antibodies specific to gp39 and their use as therapeutics and immunosuppressants.

Also, Scaria et al, *Gene Therapy*, 4:611–617 (1997) report the use of an antibody to gp39 to inhibit humoral and cellular immune responses to a DNA (adenoviral/vector).

However, while murine antibodies have applicability as therapeutic agents in humans, they are disadvantageous in some respects. Specifically, murine antibodies, because of the fact that they are of foreign species origin, may be immunogenic in humans. This often results in a neutralizing antibody response, which is particularly problematic if the antibodies are desired to be administered repeatedly, e.g., in treatment of a chronic or recurrent disease condition. Also, because they contain murine constant domains they may not exhibit human effector functions.

In an effort to eliminate or reduce such problems, chimeric antibodies have been disclosed. Chimeric antibodies contain portions of two different antibodies, typically of two different species. Generally, such antibodies contain human constant and another species, typically murine variable regions. For example, some mouse/human chimeric antibodies have been reported which exhibit binding characteristics of the parental mouse antibody, and effector functions associated with the human constant region. See, e.g., Cabilly et al, U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397, all of which are incorporated by reference herein. Generally, these chimeric antibodies are constructed by preparing a genomic gene library from DNA extracted from pre-existing murine hybridomas (Nishimura et al, *Cancer Research*, 47:999 (1987)). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes are then expressed in a cell line of choice, usually a murine myeloma line. Such chimeric antibodies have been used in human therapy.

In a commonly assigned application, Ser. No. 07/912,292, "Primatized"™ antibodies are disclosed which contain human constant and Old World monkey variable regions. These Primatized™ antibodies are well tolerated in humans given their low or weak immunogenicity.

Also, humanized antibodies are known in the art. Ideally, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (Morrison et al, *Proc. Natl. Acad. Sci., USA,* 81:6801 (1984); Morrison and Oi, *Adv. Immunol.,* 44:65 (1988) (which preserves the ligand-binding properties, but which also retains the immunogenicity of the nonhuman variable domains); (b) by grafting only the nonhuman CDRs onto human framework and constant regions with or without retention of critical framework residues (Jones et al, *Nature,* 321:522 (1986); Verhoeyen et al, *Science,* 239:1539 (1988)); or (c) by transplanting the entire nonhuman variable domains (to preserve ligand-binding properties) but also "cloaking" them with a human-like surface through judicious replacement of exposed residues (to reduce antigenicity) (Padlan, *Molec. Immunol.,* 28:489 (1991)).

Essentially, humanization by CDR grafting involves transplanting only the CDRs onto human fragment onto human framework and constant regions. Theoretically, this should substantially eliminate immunogenicity (except if allotypic or idiotypic differences exist). However, it has been reported that some framework residues of the original antibody also need to be preserved (Riechmann et al, *Nature,* 332:323 (1988); Queen et al, *Proc. Natl. Acad. Sci. USA,* 86:10,029 (1989)).

The framework residues which need to be preserved can be identified by computer modeling. Alternatively, critical framework residues may potentially be identified by comparing known antibody combining site structures (Padlan, *Molec. Immun.,* 31(3):169–217 (1994)).

The residues which potentially affect antigen binding fall into several groups. The first group comprises residues that are contiguous with the combining site surface which could therefore make direct contact with antigens. They include the amino-terminal residues and those adjacent to the CDRs. The second group includes residues that could alter the structure or relative alignment of the CDRs either by contacting the CDRs or the opposite chains. The third group comprises amino acids with buried side chains that could influence the structural integrity of the variable domains. The residues in these groups are usually found in the same positions (Padlan, 1994 (Id.) according to the adopted numbering system (see Kabat et al, "Sequences of proteins of immunological interest, 5th ed., Pub. No. 91-3242, U.S. Dept. Health & Human Services, NIH, Bethesda, Md., 1991).

However, while humanized antibodies are desirable because of their potential low immunogenicity in humans, their production is unpredictable. For example, sequence modification of antibodies may result in substantial or even total loss of antigen binding function, or loss of binding specificity. Alternatively, "humanized antibodies" may still exhibit immunogenicity in humans, irrespective of sequence modification.

Thus, there still exists a significant need in the art for novel humanized antibodies to desired antigens. More specifically, there exists a need in the art for humanized antibodies specific to gp39, because of their potential as immunotherapeutic agents.

OBJECTS OF THE INVENTION

Toward this end, it is an object of the invention to provide humanized antibodies which are specific to human gp39.

More specifically, it is an object of the invention to provide humanized antibodies derived from murine antibodies to gp39 and in particular 24-31, a specific murine antibody which binds to human gp39.

It is also an object of the invention to provide pharmaceutical compositions containing humanized antibodies which are specific to human gp39.

It is a more specific object of the invention to provide pharmaceutical compositions containing humanized antibodies derived from 24-31, a murine antibody which specifically binds to human gp39.

It is another specific object of the invention to provide methods of using humanized antibodies to human gp39 for treatment of human disease conditions, which are treatable by modulation of gp39 expression and/or inhibition of the gp39/CD40 binding interaction including, e.g., autoimmune diseases such as systemic lupus erythematosus, rheumatoid arthritis, multiple sclerosis, idiopathic thrombocytopenic purpura (ITP), diabetes and non-autoimmune conditions such as graft-versus-host disease and transplantation.

It is still another object of the invention to provide nucleic acid sequences which encode for humanized antibodies to human gp39.

It is a more specific object of the invention to provide nucleic acid sequences which encode humanized antibodies derived from 24-31, a murine antibody which specifically binds to human gp39 antigen.

It is another object of the invention to provide vectors which provide for the expression of humanized antibodies to human gp39, in particular humanized antibodies derived from 24-31, a murine antibody which specifically binds to human gp39 antigen.

SUMMARY OF THE INVENTION

In its broadest embodiment, the present invention is directed to humanized antibodies which retain not less than about one-tenth and more preferably not lower than one-third the gp39 antigen binding affinity of the murine 24-31 antibody and/or which retain not less than about one-tenth and more preferably not less than about one-third the in vitro functional activity of the murine antibody 24-31, e.g., in B-cell assays which measure T-cell dependent antibody production. More particularly, the present humanized antibodies retain at least one-tenth and more preferably at least about one-third the half-maximal potency in in vitro functional activity in a B cell assay at a concentration of not more than three times the concentration of the 24-31 antibody.

The present invention is further directed to humanized antibodies which bind to the same epitope as the murine 24-31 antibody and/or which are capable of competing with the murine 24-31 antibody for inhibiting the binding of CD40 to gp39 and/or which contain the CDR's of the 24-31 antibody.

The present invention is more preferably directed to humanized antibodies derived from murine 24-31 which possess the humanized variable light sequences and/or humanized variable heavy sequences set forth below:

(1) DIVMTQSPSFLSASVGDRVTITC KASQNVITAVA WYQQKPGKSPKLLIY SASNRYT [SEQ ID NO:1]
    GVPDRFSGSGSGTDFTLTISSLQPEDFADYFC QQYNSYPYT FGGGTKLEIK;

(2) DIVMTQSPDSLAVSLGERATINC KASQNVITAVA WYQQKPGQSPKLLIY SASNRYT [SEQ ID NO:2]
    GVPDRFSGSGSGTDFTLTISSLQAEDVADYFC QQYNSYPYT FGGGTKLEIK;

(3) DIVMTQSPSFMSTSVGDRVTITC KASQNVITAVA WYQQKPGKSPKLLIY SASNRYT [SEQ ID NO:3]
    GVPDRFSGSGSGTDFTLTISSMQPEDFADYFC QQYNSYPYT FGGGTKLEIK;

(4) DIVMTQSPDSMATSLGERVTINC KASQNVITAVA WYQQKPGQSPKLLIY SASNRYT [SEQ ID NO:4]
    GVPDRFSGSGSGTDFTLTISSMQAEDVADYFC QQYNSYPYT FGGGTKLEIK and a humanized variable heavy sequence selected from the following group:

(1) EVQLQESGPGLVKPSETLSLTCTVSGDSIT NGFWI WIRKPPGNKLEYMG YISYSGSTYYNPSLKS [SEQ ID NO:5]
    RISISRDTSKNQFSLKLSSVTAADTGVYYCAC RSYGRTPYYFDF WGQGTTLTVSS;

(2) EVQLQESGPGLVKPSQTLSLTCTVSGDSIT NGFWI WIRKHPGNKLEYMG YISYSGSTYYNPSLKS [SEQ ID NO:6]
    RISISRDTSKNQFSLKLSSVTAADTGVYYCAC RSYGRTPYYFDF WGQGTTLTVSS;

(3) EVQLQESGPGLVKPSQTLSLTCAVSGDSIT NGFWI WIRKHPGNKLEYMG YISYSGSTYYNPSLKS [SEQ ID NO:7]
    RISISRDTSKNQFSLKLSSVTAADTGVYYCAC RSYGRTPYYFDF WGQGTTLTVSS;

(4) EVQLQESGPGLVKPSETLSLTCAVYGDSIT NGFWI WIRKPPGNKLEYMG YISYSGSTYYNPSLKS [SEQ ID NO:8]
    RISISRDTSKNQFYLKLSSVTAADTGVYYCAC RSYGRTPYYFDF WGQGTTLTVSS as well as variants and equivalents thereof. Variants and equivalents thereof in the present invention are intended to embrace humanized immunoglobulin sequences wherein one or several of the amino acid residues in the above identified humanized variable heavy and/or variable light sequences are modified by substitution, addition and/or deletion in such manner that does not substantially effect gp39 antigen binding affinity. In particular, the present invention embraces variants and equivalents which contain conservative substitution mutations, i.e., the substitution of one or more amino acids by similar amino acids. For example, conservative substitution refers to the substitution of an amino acid within the same general class, e.g., an acidic amino acid, or a basic amino acid, a neutral amino acid by another amino acid within the same class. What is intended by a conservative amino acid substitution is well known in the art. Preferably, such variants and equivalents will retain not less than about one-tenth and more preferably not less than about one-third the gp39 antigen binding affinity as the parent murine 24-31 antibody and more preferably not less than about one-third the gp39 antigen binding affinity as the murine 24-31 antibody. Additionally, such variants and equivalents will preferably retain not lower than one-tenth and more preferably retain at least about one-third the in vitro functional activity of murine antibody 24-31, e.g., in B-cell assays which measure T-cell dependent antibody production. More preferably, these variants and equivalents will retain at least about one-third the in vitro functional activity of murine antibody 24-31, for example, in B-cell assays which measure T-cell dependent antibody production. More specifically, these antibodies will retain the half-maximal potency in in vitro functional activity in a B cell assay at a concentration of not more than about three times the concentration of the parent 24-31 antibody.

The present invention is further directed to nucleic acid sequences which encode for the expression of such humanized antibodies, as well as expression vectors which provide for the production of humanized antibodies in recombinant host cells. In the most preferred embodiments these DNA sequences will encode for the humanized variable heavy and/or humanized variable light sequences set forth below:

(1) DIVMTQSPSFLSASVGDRVTITC KASQNVITAVA WYQQKPGKSPKLLIY SASNRYT [SEQ ID NO:1]
    GVPDRFSGSGSGTDFTLTISSLQPEDFADYFC QQYNSYPYT FGGGTKLEIK;

(2) DIVMTQSPDSLAVSLGERATINC KASQNVITAVA WYQQKPGQSPKLLIY SASNRYT [SEQ ID NO:2]
    GVPDRFSGSGSGTDFTLTISSLQAEDVADYFC QQYNSYPYT FGGGTKLEIK;

(3) DIVMTQSPSFMSTSVGDRVTITC KASQNVITAVA WYQQKPGKSPKLLIY SASNRYT [SEQ ID NO:3]
    GVPDRFSGSGSGTDFTLTISSMQPEDFADYFC QQYNSYPYT FGGGTKLEIK;

(4) DIVMTQSPDSMATSLGERVTINC KASQNVITAVA WYQQKPGQSPKLLIY SASNRYT [SEQ ID NO:4]
    GVPDRFSGSGSGTDFTLTISSMQAEDVADYFC QQYNSYPYT FGGGTKLEIK and a humanized variable heavy sequence selected from the following group:

(1) EVQLQESGPGLVKPSETLSLTCTVSGDSIT NGFWI WIRKPPGNKLEYMG YISYSGSTYYNPSLKS [SEQ ID NO:5]
    RISISRDTSKNQFSLKLSSVTAADTGVYYCAC RSYGRTPYYFDF WGQGTTLTVSS;

-continued (2) EVQLQESGPGLVKPSQTLSLTCTVSGDSIT NGFWI WIRKHPGNKLEYMG YISYSGSTYYNPSLKS    [SEQ ID NO:6]
    RISISRDTSKNQFSLKLSSVTAADTGVYYCAC RSYGRTPYYFDF WGQGTTLTVSS;

(3) EVQLQESGPGLVKPSQTLSLTCAVSGDSIT NGFWI WIRKEPGNKLEYMG YISYSGSTYYNPSLKS    [SEQ ID NO:7]
    RISISRDTSNNQFSLNLNSVTRADTGVYYCAC RSYGRTPYYFDF WGQGTTLTVSS;

(4) EVQLQESGPGLVKPSETLSLTCAVYGDSIT NGFWI WIRKPPGNKLEYMG YISYSGSTYYNPSLKS    [SEQ ID NO:8]
    RISISRDTSKNQFYLKLSSVTAADTGVYYCAC RSYGRTPYYFDF WGQGTTLTVSS.

Moreover, the present invention also embraces equivalent and variants thereof as defined supra.

The present invention is further directed to the use of the above-identified humanized antibodies specific to gp39 as pharmaceuticals. The present invention is also directed to the use of the subject humanized anti-gp39 antibodies for treating diseases treatable by modulation of gp39 expression or by inhibition of the gp39/CD40 interaction. The present invention is more particularly directed to the use of humanized antibodies of the above-identified humanized antibodies specific to gp39 for the treatment of autoimmune disorders, for example, rheumatoid arthritis, multiple sclerosis, diabetes, systemic lupus erythematosus and ITP. The present invention is further directed to the use of the subject humanized antibodies to gp39 for the treatment of non-autoimmune disorders including graft-versus-host disease and for inhibiting graft rejection.

Also, the subject invention is further directed to usage of the subject humanized antibodies as immunosuppressants, in particular during gene or cellular therapy. The subject humanized antibodies should enhance the efficacy of gene therapy or cellular therapy by inhibiting adverse immunogenic reaction to vectors and cells used therein. For example, they may be used to inhibit humoral and cellular immune responses against viral vectors, e.g., retroviral vectors, adenoviral vectors. Also, the use of such antibodies should enable such cells or vectors to be administered repeatedly, which will facilitate treatment of chronic diseases such as cancers and autoimmune diseases.

BRIEF DESCRIPTION OF THE FIGURES

FIG. 1 depicts the IDEC expression vector N5KG1 used to express humanized and chimeric antibodies derived from 24-31. The legend is as follows:
C=Cytomegalovirus promoter/enhancer
BT=Mouse Beta globin major promoter
B=Bovine growth hormone polyadenylation
N1=Neomycin phosphotransferase exon 1
N2=Neomycin phosphotransferase exon 2
K=Human immunonoglobulin kappa constant region
G1=Human immunonoglobulin gamma 1 constant region
VL=Anti-GP39 variable light region (version #1)
VH=Anti-GP39 variable heavy region (version #1)
L=Leader
SVO=SV40origin
SV=SV40 polyadenylation
D=Dihydrofolate Reductase
BLAC=Betalactamase gene
NONCUTTERS=AvrII, Bst1107I, DraIII, FseI, HindIII, I-PpoI, I-SceI, KpnI, MluI,
MunI, PmeI, PmlI, SgrAI, SrfI, Swa I, XbaI, XcmI N5KG1 cut BglII=BsiWI and VL dropped in & cut SalI=NheI and VH dropped in.

FIG. 4 contains the amino acid sequence and DNA sequence corresponding to a preferred humanized variable light sequence (including the complementarity determining regions) referred to as VL#1 or preferred humanized variable light sequence (1).

FIG. 5 contains the amino acid and DNA sequence corresponding to a preferred humanized variable ligand sequence (including the complementarity determining regions) referred to as VL#2 or preferred humanized variable light sequence (2).

FIG. 6 contains the amino acid and DNA sequence corresponding to a preferred humanized variable heavy sequence (including the complementarity determining regions) referred to as VH#1 of preferred humanized variable heavy sequence (1).

FIG. 7 contains the amino acid and DNA sequence of the variable light sequence of 24-31 (non-humanized).

FIG. 8 contains the amino acid and DNA sequence of the variable heavy sequence of 24-31 (non-humanized).

DETAILED DESCRIPTION OF THE INVENTION

Figure 1:
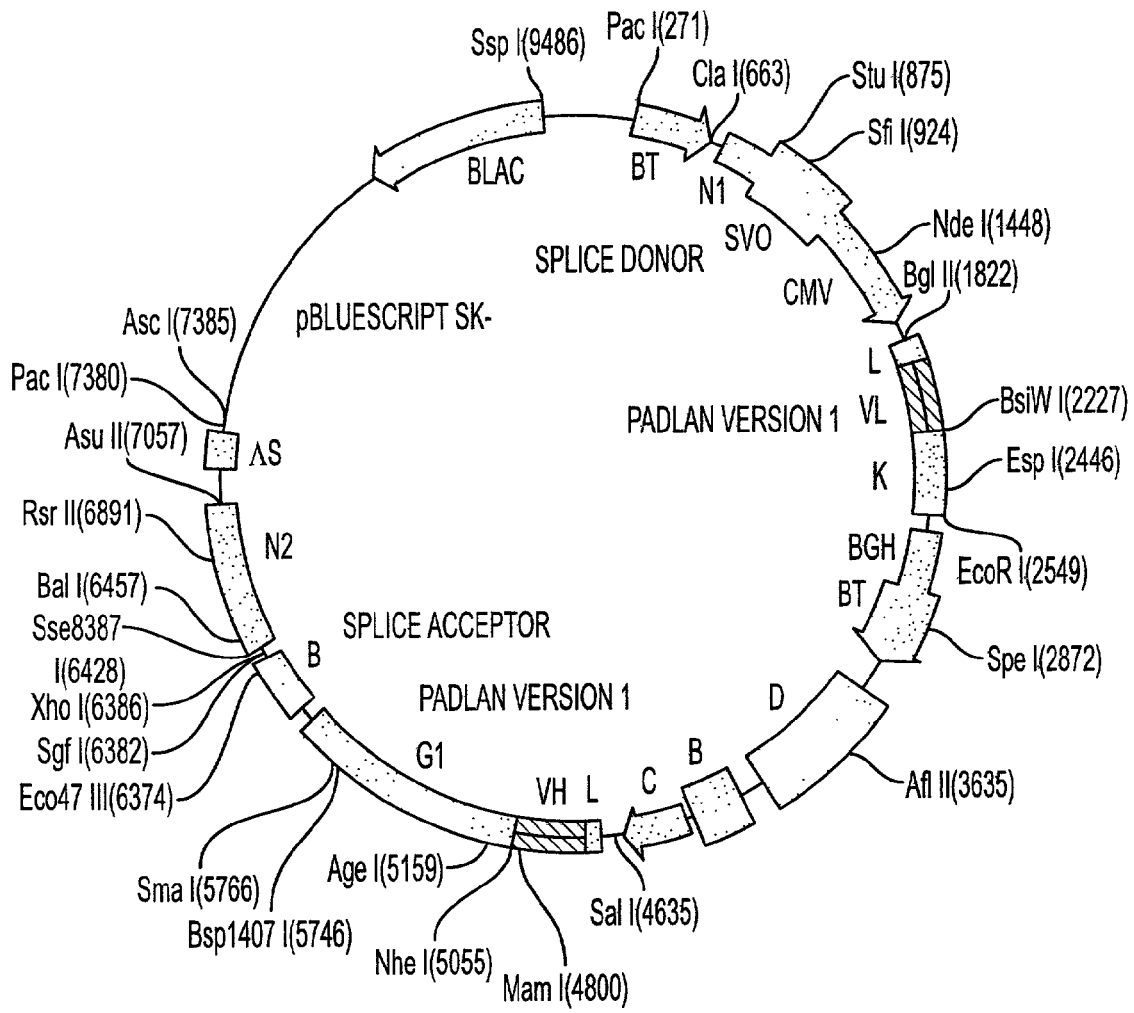

Prior to setting forth the invention, definitions of certain terms which are used in this disclosure are set forth below:

Humanized antibody—This will refer to an antibody derived from a non-human antibody, typically murine, that retains or substantially retains the antigen-binding properties of the parent antibody but which is less immunogenic in humans. This may be achieved by various methods including (a) grafting the entire non-human variable domains onto human constant regions to generate chimeric antibodies, (b) grafting only the non-human CDRs onto human framework and constant regions with or without retention of critical framework residues, or (c) transplanting the entire non-human variable domains, but "cloaking" them with a human-like section by replacement of surface residues. Such methods are disclosed in Jones et al, Morrison et al, *Proc. Natl. Acad. Sci.*, 81:6851–6855 (1984); Morrison and Oi, *Adv. Immunol.*, 44:65–92 (1988); Verhoeyen et al, *Science*, 239:1534–1536 (1988); Padlan, *Molec. Immun.*, 28:489–498 (1991); Padlan, *Molec. Immun.*, 31(3):169–217 (1994), all of which are incorporated by reference.

Complementarity Determining Region, or CDR—The term CDR, as used herein, refers to amino acid sequences which together define the binding affinity and specificity of the natural Fv region of a native immunoglobulin binding site as delineated by Kabat et al (1991).

Framework Region—The term FR, as used herein, refers to amino acid sequences interposed between CDRs. These portions of the antibody serve to hold the CDRs in appropriate orientation (allows for CDRs to bind antigen).

Constant Region—The portion of the antibody molecule which confers effector functions. In the present invention, murine constant regions are substituted by human constant regions. The constant regions of the subject chimeric or humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, chimeric antibodies with desired effector function can be produced. Preferred constant regions are gamma 1 (IgG1), gamma 3 (IgG3) and gamma 4 (IgG4). More preferred is an Fc region of the gamma 1 (IgG1) isotype. The light chain constant region can be of the kappa or lambda type, preferably of the kappa type.

Chimeric antibody—This is an antibody containing sequences derived from two different antibodies, which typically are of different species. Most typically chimeric antibodies comprise human and murine antibody fragments, generally human constant and murine variable regions.

Immunogenicity—A measure of the ability of a targeting protein or therapeutic moiety to elicit an immune response (humoral or cellular) when administered to a recipient. The present invention is concerned with the immunogenicity of the subject humanized antibodies or fragments thereof.

Humanized or chimeric antibody of reduced immunogenicity—This refers to an antibody or humanized antibody exhibiting reduced immunogenicity relative to the parent antibody, e.g., the 24-31 antibody.

Humanized antibody substantially retaining the binding properties of the parent antibody—This refers to a humanized or chimeric antibody which retains the ability to specifically bind the antigen recognized by the parent antibody used to produce such humanized or chimeric antibody. Humanized or chimeric antibodies which substantially retain the binding properties of 24-31 will bind to human gp39. Preferably the humanized or chimeric antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis. Suitable antigen binding assays are described in this application.

The present invention is directed to novel humanized monoclonal antibodies which bind human gp39 and their use as therapeutic agents. The present invention is further directed toward nucleic acid sequences which encode said humanized antibodies, and their expression in recombinant host cells.

More specifically, the present invention is directed toward humanized antibodies derived from murine antibody 24-31 which specifically binds to human gp39.

Murine antibody 24-31 is a murine antibody raised against human gp39 which functionally inactivates gp39 both in vitro and in vivo. Therefore, it possesses properties which render it potentially useful for treatment of diseases wherein gp39 inactivation and/or modulation or inhibition of the gp39/CD40 interaction is desirable. In particular, such diseases include autoimmune diseases such as, e.g., rheumatoid arthritis, multiple sclerosis, ITP, diabetes, and systemic lupus erythematosus as well as non-auto-immune diseases such as graft-versus-host disease and graft rejection.

However, while murine antibody 24-31 possesses functional properties which render it potentially suitable as a therapeutic agent, it possesses several potential disadvantages. Namely, because it is of murine origin it potentially will be immunogenic in humans. Also, because it contains murine constant sequences, it will likely not exhibit the full range of human effector functions and will probably be more rapidly cleared if administered to humans. While such disadvantages should not be problematic in the treatment of some disease conditions or persons, they pose substantial concern if the disease treated is of a chronic or recurrent nature. Examples of recurrent or chronic diseases include, e.g., autoimmune diseases, wherein the host continually or chronically exhibits an autoimmune reaction against self-antigens.

Therefore, in order to alleviate the disadvantages associated with murine antibody 24-31, namely potential immunogenicity in humans and decrease of human effector functions, the present inventors desired to produce improved, humanized derivatives of the murine 24-31 antibody. While this was the goal of the present invention, the desired result was not of a routine or predictable nature. Humanization of antibodies requires the careful selection of amino acid residues which are to be modified, and the judicious selection of residues which are to be substituted therefor. This is because modification of antibody variable regions, even those involving a few amino acid residues, may cause substantial deleterious effects on antigen binding. For example, humanized antibodies may exhibit substantially reduced antigen affinity and/or antigen-specificity in relation to the parent antibody.

As noted supra, different methods of humanization of antibodies, including murine antibodies have been reported in the literature. See, e.g., Padlan, *Molec. Immunol.,* 31(3): 169–217 (1994); Padlan, *Molec. Immunol.,* 28:484–498 (1991); Morrison and Oi, *Adv. Immunol.,* 44:65–92 (1988), all of which references are incorporated by reference in their entirety herein. These methods include in particular humanization by CDR grafting (Jones et al, *Nature,* 321:522–525 (1986); Verhoeyen et al, *Science,* 239:1534–1539 (1988); and the more tailored approach of Padlan, *Molec. Immunol.,* 28:489 (1991) and Padlan, *Molec. Immunol.,* 31:169 (1994) which involves the selection of non-essential framework amino acid residues and their modification by appropriate substitution mutation. These references are incorporated by reference in their entirety herein.

As noted, CDR grafting techniques, while successful in some instances, may substantially adversely affect the affinity of the resultant humanized antibodies. This is believed to occur because some framework residues affect or are essential for and at least affect antigen binding. Our technique; Padlan (1994) (Id.)) is more refined because we retain only those murine framework residues which we deem critical to the preservation of the antibody combining site while keeping the surface properties of the molecule as human as possible. Accordingly, this technique has the potential of producing humanized antibodies which retain the antigen-binding characteristics of the parent antibody. Because of this, this technique was selected by the present inventors as the means by which humanized antibodies derived from murine antibody 24-31 specific to human gp39 would potentially be obtained.

The cloning of the variable regions of 24-31 (described in detail in the examples infra) resulted in the identification of the $V_L$ and $V_H$ and sequences utilized by the 24-31 antibody respectively shown in FIG. 7 and FIG. 8. After sequencing, the variable regions were then humanized. As noted, this was effected substantially according to the method of Padlan (1994) (Id.), incorporated by reference supra.

This method generally comprises replacement of the non-human framework by human framework residues, while retaining only those framework residues that we deem critical to the preservation of antigen binding properties. Ideally, this methodology will confer a human-like character on the surface of the xenogeneic antibody thus rendering it less immunogenic while retaining the interior and contacting residues which affect its antigen-binding properties.

More specifically, the 24-31 $V_K$ and $V_H$ sequences set forth in FIG. 7 and FIG. 8 were humanized by comparison to human antibodies of reported sequence, which are referred to as "templares."

Specifically, the 24-31 $V_K$ was humanized using as templates:

(a) For VL#1, the human V-Kappa subgroup I sequences, e.g., DEN and the like, as well as the germline 012 (see Cox et al, *Eur. J. Immunol.* 24:827–836 (1994)), and for VL#2, the human V-Kappa subgroup IV sequences, e.g., LEN. Such template sequences are known and are reported in Kabat et al (1991) (Id.) or GenBank.

The 24-31 $V_H$#1 was humanized using as templates
(a) the human $V_H$ subgroup IV sequence, 58p2 and
(b) (GenBank Accession No.) Z18320 and the germline 3d75d (S. van der Maarel et al, *J. Immunol.,* 150:2858–2868 (1993).

Such template variable heavy antibody sequences are also known and are reported in Kabat et al, "Sequences of Proteins of Immunological Interest," 5th Ed., NIH (1991) and in GenBank.

The template human variable heavy and light sequences were selected based on a number of different criteria, including, in particular, high degree of sequence similarity with 24-31 overall, as well as similarity in the "important" residues, i.e., those which are believed to be comprised in the $V_L:V_H$ interface; those which are in contact with the complementarity determining regions, or which are inwardly pointing. Also, the templates were selected so as to potentially preserve the electrostatic charge of the 24-31 $F_v$ as much as possible, and also so as to preserve glycines, prolines and other specific amino acid residues which are believed to affect antigen binding.

This methodology resulted in the following preferred humanized $V_L$ and $V_H$ heavy sequences derived from the 24-31 antibody which are set forth below in Table 1 and Table 2. As discussed above, the invention further embraces equivalents and variants of these preferred humanized sequences, e.g., those containing one or more conservative amino acid substitutions which do not substantially affect gp39 binding. The compleinentaiity determining regions are identified in FIG. 7 and FIG. 8 which contain the entire variable heavy and light chain CDR sequences of the parent (non-humanized) 24-31 antibody.

TABLE 1

HUMANIZED 24–31 VL SEQUENCES

```
                10          20                    40                            60          70          80
24-31   DIVMTQSQKFMSTSVGDRVSITC KASQNVITAVA WYQQKPGQSPKLLIY SASNRYT GVPDRFSGSGSGTDFTLTISNMQSEDLADYFC
                        100
        QQYNSYPYT FGGGTKLEIK (1)    DIVMTQSPSFLSASVGDRVTITC KASQNVITAVA WYQQKPGKSPKLLIY SASNRYT GVPDRFSGSGSGTDFTLTISSLQPEDFADYFC
        QQYNSYPYT FGGGTKLEIK (2)    DIVMTQSPDSLAVSLGERATINC KASQNVITAVA WYQQKPGQSPKLLIY SASNRYT GVPDRFSGSGSGTDFTLTISSLQAEDVADYFC
        QQYNSYPYT FGGGTKLEIK (3)    DIVMTQSPSFMSTSVGDRVTITC KASQNVITAVA WYQQKPGKSPKLLIY SASNRT  GVPDRFSGSGSGTDFTLTISSMQPEDFADYFC
        QQYNSYPYT FGGGTKLEIK (4)    DIVMTQSPDSMATSLGERVTINC KASQNVITAVA WYQQKPGQSPKLLIY SASNRYT GVPDRFSGSGSGTDFTLTISSMQAEDVADYFC
        QQYNSYPYT FGGGTKLEIK
```

TABLE 2

HUMANIZED 24-31 VH SEQUENCES

```
              10        20        30          40
24-31  EVQLQESGPSLVKPSQTLSLTCSVTGDSIT NGFWI WIRKFPGNKLEYMG YISYSGSTYYNPSLKS
           70        82abc     90                      110
       RISITRDTSQNQFYLQLNSVTTEDTGTYYCAC RSYGRTPYYFDF WGQGTTLTVSS (1)    EVQLQESGPGLVKPSETLSLTCTVSGDSIT NGFWI WIRKPPGNKLEYMG YISYSGSTYYNPSLKS
       RISISRDTSKNQFSLKLSSVTAADTGVYYCAC RSYGRTPYYFDF WGQGTTLTVSS (2)    EVQLQESGPGLVKPSQTLSLTCTVSGDSIT NGFWI WIRKHPGNKLEYMG YISYSGSTYYNPSLKS
       RISISRDTSKNQFSLKLSSVTAADTGVYYCAC RSYGRTPYYFDF WGQGTTLTVSS (3)    EVQLQESGPGLVKPSQTLSLTCAVSGDSIT NGFWI WIRKHPGNKLEYMG YISYSGSTYYNPSLKS
       RISISRDTSNNQFSLNLNSVTRADTGVYYCAC RSYGRTPYYFDF WGQGTTLTVSS (4)    EVQLQESGPGLVKPSETLSLTCAVSGDSIT NGFWI WIRKPPGNKLEYMG YISYSGSTYYNPSLKS
       RISISRDTSKNQFYLKLSSVTAADTGVYYCAC RSYGRTPYYFDF WGQGTTLTVSS
```

As can be seen therefrom, four preferred humanized framework sequences were designed for both the $V_H$ and $V_L$ chains. Therefore, there are 16 different possible humanized 24-31 antibodies which may be synthesized using the above-identified humanized $V_H$ and $V_L$ 24-31 sequences, excluding variants and equivalents containing conservative modifications.

Humanized 24-31 antibodies containing these humanized variable heavy and light sequences may be obtained by recombinant methods. It is expected that humanized sequences which contain any combination of the above preferred humanized variable sequences will result in humanized antibodies which bind human gp39. Moreover, based on these sequences, the order of preference using the numbering set forth in Table 1 and Table 2 is expected to be as follows:

(1) #1 $V_L$ with #1 $V_H$ (Version 1)
(2) #2 $V_L$ with #1 $V_H$ (Version 2)
(3) #1 $V_L$ with #2 $V_H$ (Version 3)
(4) #2 $V_L$ with #2 $V_H$ (Version 4)

The above-identified humanized $V_H$ and $V_L$ sequences may be further modified, e.g., by the introduction of one or more additional substitution modifications and also by the addition of other amino acids. Additional modifications will be selected which do not adversely affect antigen (gp39) binding. For example, the inventors contemplate further modification of the $V_H$ chain by substitution of one or more of residues 34, 43, 44 and 68 (according to Kabat numbering scheme) Kabat et al (1991) (Id.). Also, the inventors contemplate modification of residue 85 of the $V_L$ chain. Based on the structural features of the antibody combining site, it is believed that modification of such residues should also not adversely impact antigen binding. Moreover, it is expected that the introduction of one or more conservative amino acid substitutions should not adversely affect gp39 binding.

So as to better describe the subject humanized 24-31, $V_H$ and $V_L$ sequences, the preferred humanized framework sequences are also set fort in Table 3 below, which compares these sequences to the template human variable heavy and light framework sequences, i.e., human DEN VK1, Human o12/V36 germilne, human LEN VKIV, human 58p2, human Z18320, and human 3d75d as well as to the unhumanized niurine 24-31 $V_H$ and $V_L$ framework sequences.

TABLE 3

VK Framework Region Comparisons—Humanized Anti-gp39

```
                       FR1                              FR2

Human 012 V3b germline DIQMTQSPSFLSASVGDRVTITC          WYQQKPGKAPKLLIY
Human DEN VKI          -----------T-----------          -------E---V---
Murine 24-31           --V----QK-M-T------S---          -------QS------
Padlan VL#1 humanized  --V--------------------          --------S------

FR3                              FR4

Human 012 V3b          GVPSRFSGSGSGTDFTLTISSLQPEDFATYYC
Human DEN VK1          --------------E---------SD-------  FGQGTKLEIK
Murine 24-31           ---D----------------NM-SE-L-D-F-  --G-------
Padlan VL#1            ---D------------------------D-F-  --G-------

FR1                              FR2

Human LEN VKIV         DIVMTQSPDSLAVSLGERATINC          WYQQKPGQPPKLLIY
Murine 24-31           -------QKFMST-V-D-VS-T-          --------S------
Padlan VL#2 humanized  -----------------------          --------S------

FR3                              FR4

Human LEN VKIV         GVPDRFSGSGSGTDFTLTISSLQAEDVAVYYC FGQGTKLEIK
Murine 24-31           --------------------NM-S--L-D-F- --G-------
Padlan VL#2            ----------------------------D-F- --G-------
```

TABLE 3-continued

VK Framework Region Comparisons—Humanized Anti-gp39

```
                      FR1
Human 58p2            QVQLQESGPGLVKPSETLSLTCTVSGGSIS
Murine 24-31          E---------S----Q------S-T-D--T
Padlan VH#1 humanized E-------------------------D--T Human Z18320 GenBank  ----------------Q--------------

Human 3d75d germline  ----------------Q--------------
Padlan VH#2 humanized E---------------Q---------D--T FR2                 FR3
Human 58p2            WIRQPPGKGLEWIG      RVTISVDTSKNQFSLKLSSVTAADTAVYYCAR
Murine 24-31          ---KF--NK--YM-      -IS-TR---Q---Y-Q-N---TE--GT----C
Padlan VH#1           ---K---NK--YM-      -IS--R------------------G-----C Human Z18320          ------A--------     --------------------------------
Human 3d75d           ----H----------     --------------------------------
Padlan VH#2           ---KH--NK--YM-      -IS--R------------------G-----C Human 58p2            WGQGTMVTVSS
Murine 24-31          -----TL----
Padlan VH#1           -----TL----

Human Z18320          -----------
Padlan VH#2           -----TL----
```

In order to produce humanized antibodies, DNA sequences are synthesized which encode for the afore-identified humanized $V_L$ and $V_H$ sequences. As noted, taking into account these four humanized $V_L$ sequences, and four humanized $V_H$ sequences, there are 16 potential humanized antigen combining sites which may be synthesized. Also, there are even more potential humanized antigen combining sites taking into account the potential substitution of residues 34, 43, 44 and 68 of the humanized $V_H$ and residue 85 of the humanized $V_L$ by other amino acid residues and/or the potential incorporation of conservative substitution mutations. Two of the preferred humanized variable light sequences (1) and (2) and a preferred humanized variable heavy sequence (1) including the complemenranty determining regions and corresponding DNA sequences are set forth in FIGS. 4, 5, and 6, respectively.

Methods for synthesizing DNA encoding for a protein of known sequence are well known in the art. Using such methods, DNA sequences which encode the subject humanized $V_L$ and $V_H$ sequences are synthesized, and then expressed in vector systems suitable for expression of recombinant antibodies. This may be effected in any vector system which provides for the subject humanized $V_L$ and $V_H$ sequences to be expressed as a fusion protein with human constant domain sequences and associate to produce functional (antigen binding) antibodies.

Expression vectors and host cells suitable for expression of recombinant antibodies and humanized antibodies in particular, are well known in the art.

The following references are representative of methods and vectors suitable for expression of recombinant immunoglobulins which are incorporated by reference herein: Weidle et al, Gene, 51:21–29 (1987); Dorai et al, J. Immunol., 13(12):4232–4241 (1987); De Waele et al, Eur. J. Biochem., 176:287–295 (1988); Colcher et al, Cancer Res., 49:1738–1745 (1989); Wood et al, J. Immunol., 145(a): 3011–3016 (1990); Bulens et al, Eur. J. Biochem., 195: 235–242 (1991); Beggington et al, Biol. Technology, 10:169 (1992); King et al, Biochem. J., 281:317–323 (1992); Page et al, Biol. Technology, 9:64 (1991); King et al, Biochem. J., 290:723–729 (1993); Chaudary et al, Nature, 339:394–397 (1989); Jones et al, Nature, 321:522–525 (1986); Morrison and Oi, Adv. Immunol., 44:65–92 (1988); Benhar et al, Proc. Natl. Acad. Sci. USA, 91:12051–12055 (1994); Singer et al, J. Immunol., 150:2844–2857 (1993); Cooto et al, Hybridoma, 13(3):215–219 (1994); Queen et al, Proc. Natl. Acad. Sci. USA, 86:10029–10033 (1989); Caron et al, Cancer Res., 32:6761–6767 (1992); Cotoma et al, J. Immunol. Meth., 152:89–109 (1992). Moreover, vectors suitable for expression of recombinant antibodies are commercially available.

Host cells known to be capable of expressing functional immunoglobulins include by way of example mammalian cells such as Chinese Hamster Ovary (CHO) cells, COS cells, myeloma cells, bacteria such as Escherichia coli, yeast cells such as Saccharomyces cerevisiae, among other host cells. Of these, CHO cells are used by many researchers given their ability to effectively express and secrete immunoglobulins.

Essentially, recombinant expression of humanized antibodies are effected by one of two general methods. In the first method, the host cells are transfected with a single vector which provides for the expression of both heavy and light variable sequences fused to selected constant regions. In the second method, host cells are transfected with two vectors, which respectively provide for expression of either the variable heavy or light sequence fused to selected constant regions.

Human constant domain sequences are well known in the art, and have been reported in the literature. Preferred human $V_L$ sequences includes the Kappa and lambda constant light sequences. Preferred human heavy constant sequences include human gamma 1, human gamma 2, human gamma 3, human gamma 4 and mutated versions thereof which provide for altered effect or function, e.g. enhanced in vivo half-life and reduced Fc receptor binding.

Preferred modifications of the human gamma 4 constant domain include E and/or P modifications, which respectively refer to the change of a leucine to a glutamic acid at position 236 and/or, the change of a serine to a proline at position 229 such as described in commonly assigned U.S. patent application Ser. No. 08/523,894, filed on Sep. 6, 1995, which issued as U.S. Pat. No. 6,136,310 on Oct. 24, 2000, and incorporated by reference in its entirety herein.

A particularly preferred vector system comprises the expression vectors described in commonly assigned U.S. Ser. No. 08/476,237 filed Jun. 7, 1995, Ser. No. 08/397,072, filed Jan. 25, 1995 and 07/912,122 filed Jul. 10, 1992, 07/886,281 filed Mar. 23, 1992, and 07/735,064 filed Jul. 25, 1991, all incorporated by reference in their entirety.

In particular, these applications describe vector systems for the production of recombinant antibodies, referred to as TCAE 5.2 and TCAE 6 which comprise the following:

1) Four transcriptional cassettes in tandem order:
   (a) a human immunoglobulin light chain constant region. In TCAE 5.2 this is the human immunoglobulin Kappa light chain constant region (Kabat numbering amino acids 108–214, allotype Km 3) and in TCAE 6 the human immunoglobulin light chain lambda constant region (Kabat numbering amino acids 108–215, genotype Oz minus, Mcg minus, Ke minus allotype).
   (b) a human immunoglobulin heavy chain constant region; in both constructs the human immunoglobulin heavy chain is a gamma/constant region (Kabat numbering amino acids 114–478 allotype Gm1a, Gm12).
   (c) DHFR; containing its own eukaryotic promoter and polyadenylation region; and
   (d) NEO; also containing its own eukaryotic promoter and polyadenylation region.

2) The human immunoglobulin light and heavy chain cassettes contain synthetic signal sequences for secretion of the immunoglobulin chains; and 3) The human immunoglobulin light and heavy chain cassettes contain specific DNA links which allow for the insertion of light and heavy immunoglobulin variable regions which maintain the translational reading frame and do not alter the amino acids normally found in immunoglobulin chains.

These vectors are preferably utilized in CHO cells. The subject antibodies are preferably expressed in the above-described vector systems.

However, the subject humanized antibody sequences derived from the number 24-31 antibody may be expressed in any vector system which provides for the expression of functional antibodies, i.e., those which bind gp39 antigen.

In particular, the inventors elected to express the subject humanized $V_L$ and $V_H$ sequences, as well as the native (unmodified) $V_L$ and $V_H$ sequences derived from 24-31 in CHO cells using the N5KG1 expression vector which contains human Kappa and human gamma 1 constant regions. The N5KG1 expression vector is depicted schematically in FIG. 1. As hoped, the chimeric antibody derived from 24-31, when expressed in CHO cells binds gp39 (by demonstrated binding to CHO-gp39 transfectant). Also, several humanized antibodies of the invention derived from 24-31 when expressed using this vector system resulted in functional (gp39 binding) antibodies.

The present invention is further described through presentation of the following examples. These examples are offered by way of illustration and not by way of limitation.

EXAMPLE 1

Selection of 24-31 Antibody for Humanization.

Accumulating evidence in animal models indicates that anti-gp39 administration prevents a variety of autoimmune processes and interferes with allograft rejection. These results provide compelling evidence that antibodies to human gp39 may have significant therapeutic value in the management of autoimmune disease and the transplantation of allogeneic tissue and organs in humans. A monoclonal antibody (mAb) specific for human gp39 has been reported (Lederman et al, *J. Immunol.*, 199:3817 (1992)), and its functional activity in blocking gp39-CD40 interactions in vitro has been evaluated. To gain greater insights into the functional impact of anti-gp39 antibodies on the human immune system, a panel of anti-human gp39 mAbs was generated. From this panel, one mAb appeared superior and was extensively tested for functional inactivation of gp39 in vitro and in vivo.

More specifically, a panel of 6 murine (all IgG1) anti-gp39 antibodies was generated by immunization with a soluble fusion protein of human gp39 (gp39-CD8), followed by challenge with activated human peripheral blood T cells. Flow cytometric analysis of human peripheral blood T cells demonstrated that the mAbs recognized a cell surface molecule expressed on activated (PMA/ionomycin), but not resting, CD3$^+$ T cells, and that the pattern of reactivity was similar to that seen with a recombinant CD40 fusion protein (CD40-Ig) (data not shown). Immunoprecipitation of [$^{35}$S] metabolically labeled activated human peripheral blood T cells revealed that each of the 6 mAbs precipitated a molecule of similar size (33 kDa) to that precipitated by CD40-Ig. Finally, binding of CD40-Ig to gp39 was blocked in the presence of the antibodies indicating recognition of the same molecule, further confirming their specificity. Although all 6 mAbs were capable of blocking gp39 function, one mAb, 24-31, was selected for extensive analysis.

EXAMPLE 2

T Cell-dependent B Cell Proliferation and Differentiation (Ig Production) is Blocked by Anti-gp39.

Figure 2A:
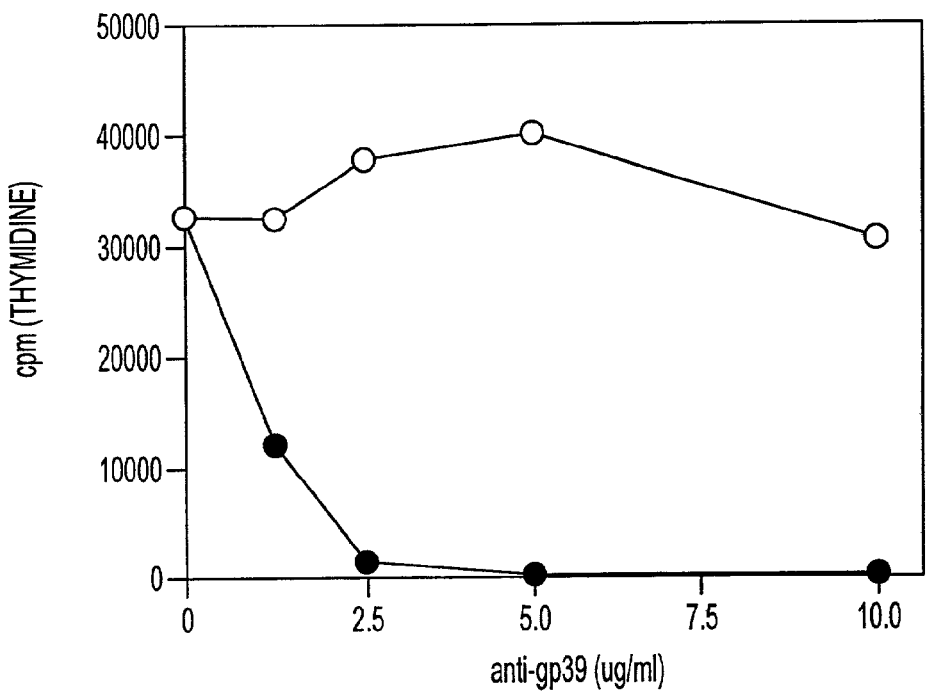
FIG. 2a contains results of a B cell proliferation assay which contacts human PBLs with soluble gp39-CD8, recombinant human IL4 and the murine 24-31 antibody or control murine IgG1 monoclonal antibody which demonstrate that 24-31 antibody inhibits B cell proliferation inducted by gp39. Human PBL were cultured in 96 well plates ($0.1 \times 10^6$/well) in the presence or absence of the 20% (v/v) soluble gp39-CD8 (sgp39-CD8) fusion protein and 5 ug/ml rhuIL-4 for 3 d. Anti-gp39 mAb, 24-31 (●), or a control murine IgG1 mAb (○), were added at a range of concentrations (1.25–10 ug/ml). Cultures were pulsed with 1 uCi3H-thymidine during the final 6 hr of a 72 hr culture period.
Figure 2B:
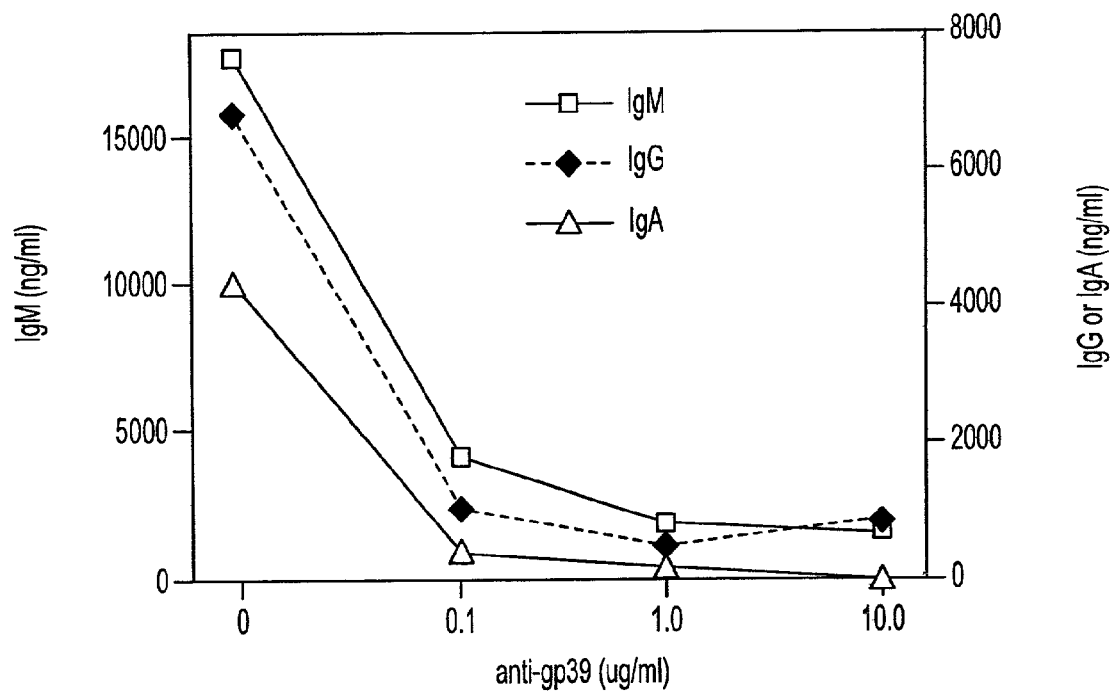
FIG. 2b contains results of B cell differentiation assay using mitomycin treated T cells activated with immobilized anti-CD3 cultured in the present of $IGD^+$ B cells and different concentrations of the 24-31 antibody which demonstrate that 24-31 antibody inhibits T-cell dependent polyclonal antibody production by human B cells. Mitomycin treated T cells ($5 \times 10^4$/well) activated with immobilized anti-CD3 (64.1) were cultured with $2.5'10^4$/well $lgD^{30}$ B cells in 96-well microtiter plates for 12d in the presence or absence of various concentrations (0.1–10.0 ug/ml) of anti-gp39 mAb, 24-31. Culture supernatants were subsequently assayed for lgM (□), lgG (♦), and lgA (Δ) by isotype specific ELISA.

A number of studies have provided evidence that signals delivered through CD40 by its ligand, gp39, induce B cell activation, proliferation, differentiation, and isotype switching. To determine if the anti-gp39 24-31 mAb blocked gp39 function, B cells were cultured with a soluble fusion protein of gp39 (gp39-CD8) in the presence or absence of 24-31, and the B cell proliferative response was assessed by $^3$H-thymidine incorporation. The results, shown in FIG. 2A, demonstrate that gp39-CD8 induced vigorous proliferation of B cells. The presence of anti-gp39 24-31 mAb completely ablated B cell proliferation induced by gp39-CD8 at con centrations as low as 2.5 µg/ml. To determine whether 24-31 interfered with T cell-induced B cell differentiation, B cells were co-cultured with anti-CD3 activated T cells in the presence or absence of 24-31. Polyclonal IgM, IgG, and IgA production was assessed after 12 days. As shown in FIG. 2B, the addition of 24-31 inhibited polyclonal IgM, IgG, and IgA antibody production (90–99%). These results confirm previous reports establishing the requirement for gp39-CD40 interactions in T cell-dependent B cell differentiation (Nishioka et al, *J. Immunol.*, 153:1027 (1994), and further demonstrate the use of newly characterized anti-human gp39 24-31 mAb in blocking gp39 function.

EXAMPLE 3

Anti-gp39 Blocks in Vivo Tetanus Toxoid Specific Antibody Production in SCID Mice Reconstituted with Human PBL.

Numerous studies have established that the human immune system can be studied in vivo under experimental conditions through the use of severe combined immunodeficiency (scid) mice engrafted with human peripheral blood lymphocytes (hu-PBL-scid mice) (Mosler et al, *Nature*, 335:256 (1988); McCune et al, *Science*, 241:1632 (1988). Long-term chimerism is achieved in scid mice by injection with human PBL, and antigen-specific secondary antibody responses are detected in hu-PBL-scid mice challenged in vivo with antigen (Carlsson et al, *J. Immunol.*, 148:1065 (1992); Duchosal et al, *Cell Immunol.*, 139:468 (1992)). This system was exploited to evaluate the immunosuppressive effects of in vivo anti-gp39 administration on the immune responses elicited by human T and B cells.

Experiments, the results of which are contained in FIG. 2B, demonstrated that blockade of gp39 function by 24-31 inhibited T cell-dependent polyclonal Ig production by human B cells in vitro. To determine whether 24-31 could also inhibit antigen specific B cell antibody production in vivo, C.B-17 scid/scid mice injected i.p. with human PBL (hu-PBL-scid) and immunized with tetanus toxoid (TT) were treated with 24-31 or PBS, and the secondary (IgG) anti-TT antibody response was assessed. Immunization of hu-PBL-scid with TT resulted in detectable levels of IgG anti-TT antibody within 14 days post immunization in most animals (Table 4). However, treatment with anti-gp39 (24-31; 250 µg/day, twice weekly) completely ablated the secondary anti-TT antibody response in 9/10 mice examined, demonstrating that in vivo blockade of gp39 function also resulted in inhibition of antigen specific humoral responses.

TABLE 4

Ablation of the secondary anti-tetanus antibody response following engraftment of human PBL in C.B-17 scid/scid mice immunized with tetanus toxoid.*

| Recipient Strain* | Treatment¶ | Anti-Tetanus Antibody (O.D. ± SE)§ (Frequency of Mice Containing Anti-Tetanus Antibody) days post immunization | | | |
|---|---|---|---|---|---|
| | | 7 d | 14 d | 21 d | 28 d |
| C.B-17 scid/scid | PBS | <0.02 (0/10) | 2.30 ± .042 (7/10)* | .224 ± .040 (8/10)** | .137 + .007 (4/10) |
| | anti-gp39 | .162 (1/10) | <0.02 (0/10) | <0.02 (0/10) | <0.02 (0/10) |

Four–six week old C.B-17-scid/scid mice were injected i.p. with 20 × $10^6$ human PBL and 0.25 ml tetanus toxoid.
¶Anti-gp39 24–31 or PBS (250 µg/injection) was administered i.p. twice weekly throughout the entire experiment.
§The level of human anti-tetanus toxoid antibody in the serum was determined weekly by ELISA. All mice with serum levels of human anti-tetanus toxoid antibody >0.100 O.D. at a 1:10 dilution were considered positive. Only positive mice were used in the calculation of the mean ± SE values included in the table. The level of human anti-tetanus toxoid in sera from pre-immune mice not immunized with tetanus toxoid was <0.02 O.D. Data are presented as mean ± SE.
*Significantly different (p = 0.222) than the anti-gp39 treated group.
**Significantly different (p < 0.001) than the anti-gp39 treated group.

EXAMPLE 4

Anti-gp39 Treatment does not Inhibit the Antigen-specific T Cell Proliferative Response of Hu-PBL-scid Spleen Cells.

To determine whether treatment of hu-PBL-scid mice with anti-gp39 altered the responsiveness of antigen-specific T cells in vivo, the proliferative response of spleen cells from hu-PBL-scid mice immunized with TT and treated with 24-31 was assessed in vitro. Spleen cells from control or anti-gp39 treated hu-PBL-scid mice were cultured with TT or medium alone, and the proliferative response was assessed by $^3$H-thymidine incorporation after 6 days. Table summarizes the results of one such experiment. Hu-PBL-scid mice treated with anti-gp39 responded similarly to in vitro stimulation with TT as did hu-PBL-scid mice which were untreated (5/10 vs. 3/10 responding mice). Experiments using NOD/LtSz-scid/scid mice as recipients yielded similar results, although anti-TT antibodies were undetectable in these mice (data not shown). These data demonstrate that treatment with anti-gp39 does not result in deletion or functional inactivation of antigen-specific T cells in hu-PBL-scid mice and support the contention that inhibition of TT specific antibody responses by anti-gp39 is due to blockade of gp39-CD40 interactions and subsequent B cell responses rather than T cell inactivation.

TABLE 5

Anti-gp39 treatment does not alter the anti-tetanus T cell proliferative response following engraftment of human PBL in C.B-17-scid/scid or NOD/LtSz-scid/scid mice immunized with tetanus toxoid.

| Recipient Strain* | Treatment¶ | Frequency of Responding Mice§ |
|---|---|---|
| C.B-17 scid/scid | PBS | 3/10 |
| | anti-gp39 | 5/10 |
| NOD/LtSz-scid/scid | PBS | 5/10 |
| | anti-gp39 | 6/10 |

*Four–six week old C.B-17-scid/scid or NOD/LtSz-scid/scid mice were injected i.p. with $20 \times 10^6$ human PBL and 0.25 ml tetanus toxoid.
¶Anti-gp39 24–31 or PBS (250 μg/injection) was administered i.p. twice weekly throughout the entire experiment.
§Spleen cells from mice injected with human PBL and immunized with tetanus toxoid were cultured at a concentration of $1 \times 10^5$ cells/ml in the presence of media alone or tetanus toxoid (2.5 or 5.0 μg/ml). Proliferation was assessed by $^3$H-thymidine incorporation after 6 d. Stimulation indices were calculated by the following formula" S.I. = cpm tetanus – cpm medium/cpm medium. S.I. of > than 2.0 was considered positive.

¶Anti-gp39 24–31 or PBS (250 μg/injection) was administered i.p. twice weekly throughout the entire experiment. § Spleen cells from mice injected with human PBL and immunized with tetanus toxoid were cultured at a concentration of $1 \times 10^5$ cells/ml in the presence of media alone or tetanus toxoid (2.5 or 5.0 μg/ml). Proliferation was assessed by $^3$H-thymidine incorporation after 6d. Stimulation indices were calculated by the following formula" S.I.=cpm tetanus–cpm medium/cpm medium. S.I. of >than 2.0 was considered positive.

EXAMPLE 5

Generation of a gp39 CHO Transfectant Cell Line.

Figure 3:
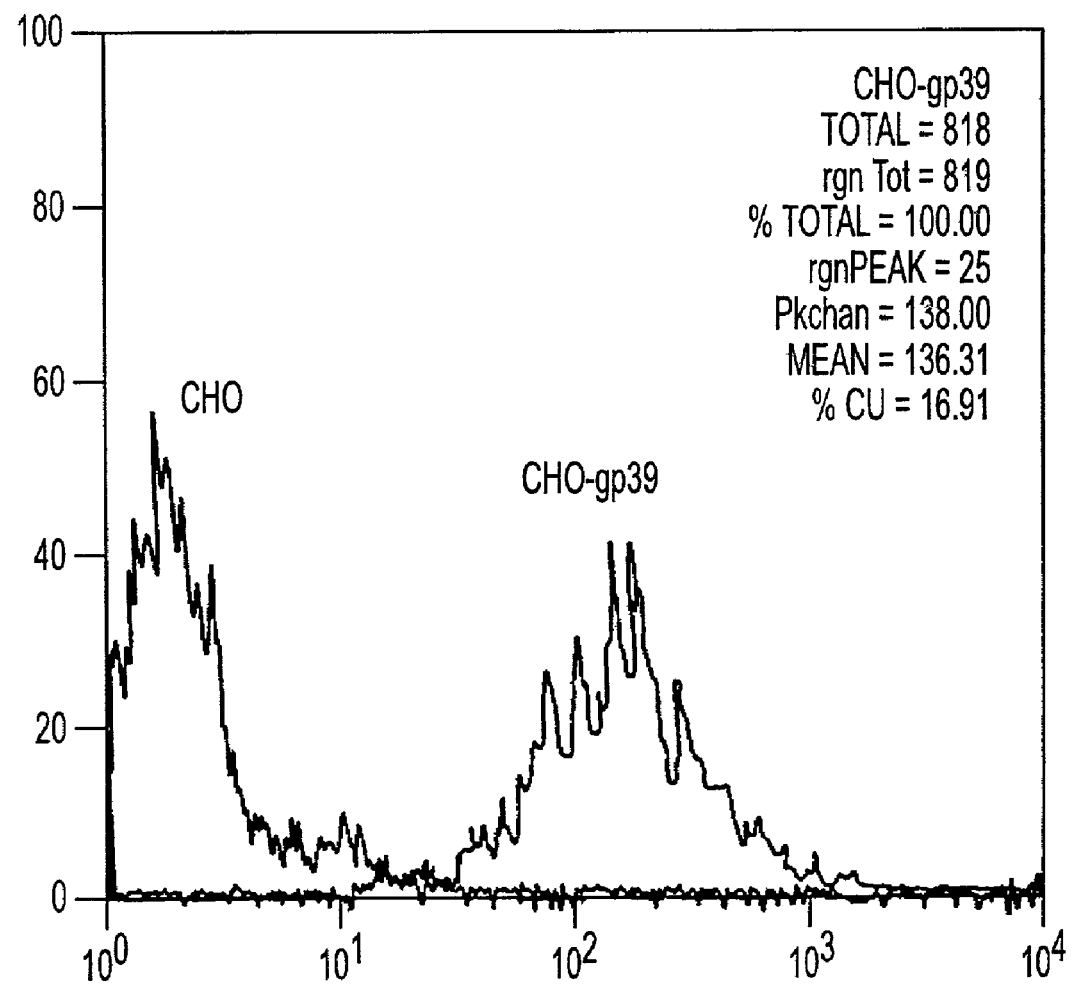
FIG. 3 contains FACS of non-transfected CHO cells and a gp39 transfectant.—FACS analysis of non-transfected CHO cells and a gp39 transfectant. $1 \times 10^6$ cells were treated with the mouse anti-gp39 antibody 24-31 and then with a goat-anti-mouse lgG-FITC conjugate (Southern Biotechnology Associates). The samples were analyzed on FACScan (Becton Dickenson).

Recently, a CHO transfectant that constitutively expresses cell-surface gp39 was generated to use as a reagent for the humanized anti-gp39 24-31 binding studies proposed in this application. The full-length gp39 gene (Hollenbaugh et al, *Immunol. Rev.*, 138:23 (1994)) was amplified by polymerase chain reaction (PCR) of phytohemag-glutinin-activated human PBL and cloned into IDEC's INPEP4 vector under the transcriptional control of the cytomegalo-virus (CMV) promoter and enhancer elements. A CHO transfectant was established and amplified in 50 nM methotrexate. The transfectant, 50D4, was shown to express cell-surface gp39 by ELISA (data not shown) and FACS analysis (FIG. 3).

EXAMPLE 6

High-level Expression of Antibodies using a CHO Expression System.

IDEC's proprietary N5KG1 expression vector is used in CHO cells for expression of the humanized anti-gp39 24-31 antibody. This vector is depicted schematically in FIG. 1. High-level expression of recombinant antibodies is consistently obtained in CHO cells using this vector and similar vectors. Using these vectors, a high percentage of G418 resistant clones, 5–10%, are found to express significant amounts of recombinant proteins (1–10 mg/l of antibody). These are usually single plasmid copy integrants, and can easily be amplified using methotrexate to obtain 30–100 pg/cell/day of secreted immunoglobulin. Table 6 lists the antibody levels obtained before and after gene amplification of 3 antibodies expressed in CHO cells utilizing this system.

TABLE 6

Antibody production levels using IDEC's CHO expression technology.

| Antibody | before amplification mg/l | after amplification in spinner flask mg/l | after amplification in fermentor mg/l |
|---|---|---|---|
| Anti-CD4 γ1 | 1–2 | 100–110 | 950 |
| Anti-CD4 γ4 | 3–4 | 125–150 | N.D. |
| Anti-CD20 | 5–10 | 200–300 | 650 |

EXAMPLE 7

Cloning of 24-31 $V_k$ and $V_H$ DNA Sequences

The anti-gp39 24-31 $V_k$ and $V_H$ gene segments were cloned and sequenced. Following analyses of their sequences, humanized versions of the V region gene segments were designed. The corresponding DNA sequences were synthesized and cloned into a high-level expression vector containing human constant region genes. A CHO transfectant producing the humanized 24-31 antibody is then established. To confirm that the humanized version of the anti-gp39 antibody retains its gp39 binding affinity, the relative affinities of the murine and humanized antibodies were compared in direct binding and competition assays. In addition, the ability of the humanized 24-31 to block CD40 binding to gp39 and to inhibit T cell-dependent antibody production is evaluated.

1. Cloning of the 24-31 $V_k$ and $V_H$ Gene Segments
   a. Preparation of cDNA. PolyA$^+$ mRNA was prepared from $2 \times 10^6$ cells each of the 24-31 hybridoma and the NS1 cell line, (Carroll et al, *Mol. Immunol.*, 10:991 (1988)), the fusion partner used in the generation of the 24-31 hybridoma, utilizing an Invitrogen Corporation Micro-Fast Track™ mRNA isolation kit, according to the manufacturer's protocol. First strand cDNA was synthesized utilizing 50 pmoles oligo-dT and 5 units M-MLV reverse transcriptase (Promega) (Sambrook et al, *Molecular Cloning: A Laboratory Manual*, 2nd Ed., Cold Spring Harbor Laboratory Press (1989)) followed by Sephadex G-25 chromatography.
   b. PCR amplification of $V_k$ and $V_H$ cDNA 24-31 and NS1 cDNA were amplified by PCR using a panel of 5' pnrners specific for $V_k$ or $V_H$ leader sequences in combination with 3' constant region primers. The pane) of 5' $V_H$ primers are identical to those described by Jones and Bendig (*Bio/Technol.*, 9:88 (1991); Errata, *Bio/Technol.*, 9:579 (1991)). The panel of 5' $V_k$ primers (Jones et al., (Id.)) were modified to convert the Sal I cloning site recognition sequences (GTCGAC) into Bgl II recognition sequences (AGATCT) to facilitate the cloning of the amplified gene segments into IDEC's N5KG1 expression vector (See FIG. 1). The 3' $V_k$ and $V_H$ primers contain a Bsi WI cloning site sequence at amino acid positions 108–109 (numbering according to Kabat et al., "Sequences of Proteins of Immunological Interest," 5th Ed., NIH (1991)) and a Nhe I cloning site sequence at positions 114–115, respectively, and have the following sequences:
   TGCAGCATCCGTACGTTGATTCCAGCTT ($C_k$) and GGGGGGTGCGTGCTAGCTG (A/C) (G/A) GAGAC (G/A) GTGA ($C_{65}$ 1). This primer panel has been previously used by the Assignee to amplify and clone the C2B8 anti-CD20 antibody (Nishioka et al., *J. Immunol.*, 153:1027(1994)) and numerous other mouse $V_k$ and $V_H$ gene segments (data not shown).

In order to determine the correct primer pair for the amplification of the 24-31 $V_k$ and $V_H$ gene segments, the 24-31 cDNA were amplified in 23 individual reactions containing one of the 11 5'$V_k$ primers in combination with the $C_K$ primer or one of the 12 5'$V_H$ primers in combination with the Cγ1 primer. For comparison, NS1 cDNA was amplified using the same panel of primers. 1 μl cDNA (1/50 of the cDNA sample) was amplified in a 100 μl final volume containing 5 units Taq DNA polymerase (Perkin Elmer), 10 mM Tris-HCl, pH 8.3, 50 mM KCl, 1.5 mM $MgCl_2$, 0.25 mM each of dCTP, dGTP, dATP, and TTP, 50 pmoles 3' constant region primer, and 50 pmoles 5' primer. The amplification cycle consisted of denaturation for 1 minute at 95° C., annealing for 2 minutes at 50° C., and extension for 2 minutes at 72° C., repeated 34 times. The amplified products were analyzed by agarose gel electrophoresis. The 24-31 PCR reactions yielding a unique amplified product for $V_k$ and for $V_H$ were repeated and the products from duplicate PCR reactions cloned. PCR amplified products are agarose gel-purified (Sambrook et al, *Molecular Cloning: A Laboratory Manual*, 2nd Ed. (1989)) and digested with Bgl II and Bsi WI (for $V_k$) or Sal I and Nhe I (for $V_H$). The products are ligated (Ausabel et al, Current Protocols in *Molecular Biology*, Vol. 2, Greene Publ. Assoc. (1992)) sequentially into IDEC's vector, N5KG1.

Following transformation of *E. coli* XL1-blue cells (Stratagene), plasmid DNA was prepared, and the $V_k$ and $V_H$ sequences obtained from the duplicate constructs (sequencing performed by Scripps Research Institute Core Facility, La Jolla, Calif.). The sequences of the endogenous light and heavy chains of the NS1 fusion partner are known (Carroll et al, *Mol. Immunol.*, 10:991 (1988); Kabat et al, (1991) (Id.)) and were used to distinguish PCR products resulting from the amplification of the 24-31 versus the NS1 fusion partner V regions.

EXAMPLE 8

Synthesis of Gene Segments Encoding Humanized 24-31 V Regions.

Humanized versions containing the most preferred humanized 24-31 $V_k$ and $V_H$ sequences identified in Tables 1 and 2 as humanized $V_L$ and $V_H$ (1) were synthesized. Specifically, four pairs of overlapping, complementary olionucleotides (oligos) encoding the above-identified humanized $V_k$ or $V_H$ regions were synthesized (Midland Chemicals) and purified by denaturing polyacrylamide gel electrophoresis (Ausubel et al, *Current Protocols in Molecular Biology*, Vol. 2, Greene Publ. Assoc. (1992)). Each oligo is approximately 100 bases in length and overlap by 20 bases the adjacent complementary oligonucleotide. The $V_k$ and $V_H$ 5' oligos contain Bgl II and Sal I cloning sites and the 3' oligos possess Bsi WI and Nhe I cloning sites, respectively. Each variable region gene segment was assembled from the synthetic oligos, diagrammed below, using the following procedure (summarized in Watson et al, *Recombinant DNA*, 2nd Ed., Scientif. Amer. Books, NY, N.Y. (1992)). Complementary oligo pairs (A+E, B+F, C+G, D+F) were kinased using 300 pmoles of each primer and T4 polynucleotide kinase (Promega) according to the manufacturer's protocol. The oligos were annealed by heating to 95° C. and slow cooling to room temperature. The annealed oligo pairs were ligated (A/E with B/F and C/G with D/H) utilizing 6 units T4 DNA ligase (New England Biolabs). After digestion with the appropriate 5' or 3' cloning site restriction endonuclease, the approximately 200 base pair DNA fragments were purified by electroelution following polyacrylamide gel electrophoresis (Sambrook et al, (Id.)). The synthetic gene fragments were then inserted into IDEC's proprietary high-level expression vector, N5KG1, under the transcriptional control of the CMV promoter and enhancer elements. The ligation reaction contains the 2 gel-purified fragments (A/E/B/F and C/G/D/H) and N5KG1 at a molar ratio of 100:100:1, respectively. After transformation of XL1-blue cells, plasmid DNA was prepared and the sequences of the synthetic gene segments confirmed. The resulting construct, h24-31, encodes the humanized 24-31 V region segments and human kappa and gamma 1 constant regions. As indicated, this antibody contains the humanized variable heavy and humanized variable light sequences identified in Table 1 and Table 2 as the "(1)" sequences, which are predicted to provide for humanized antibody having optimal gp39 properties. In addition, a construct was generated which contains $V_L$#2 in combination with $V_H$ #1 (version 2 of humanized 24-31). Similar constructs utilizing IDEC's proprietary vectors have been used for high-level expression of IDEC's anti-CD20 (Reff et al, *Blood*, 83:425 (1994)) and anti-CD4 (Newman et al, *Biol. Technology*, 10:1455 (1992)) antibodies.

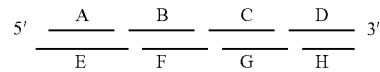

EXAMPLE 9

2. Production and Characterization of Humanized 24-31 a. Generation of CHO transfectants producing humanized 24-31 (version 1 and version 2).

CHO transfectants expressing humanized 24-31 (version 1 or version 2) were generated by electroporation of $4\times10^6$ CHO cells with linearized h24-31 DNA (version 1 or version 2) followed by selection in G418. The cell culture supernatants from G418 resistant clones were assayed for immunoglobulin production by sandwich ELISA employing a goat anti-human kappa to capture the immunoglobulin. Immunoglobulin binding was measured by incubating with a horse radish peroxidase (HRP)-conjugated goat antibody specific for human IgG, followed by HRP substrate, 0.4 mg/ml O-Phenylene-diamine (OPD) in a citrate buffer (9–34 g/l $C_6H_8O_7$ and 14.2 g/l $Na_2HPO_4$), pH 5.0, including 0.0175% $H_2O_2$. The plate was read in a Molecular DeviCes "Vmax, kinetic microplate reader" spectrophotometer at 490 nm.

EXAMPLE 10 b. Characterization of Humanized 24-31 (Version 1).

The humanized anti-gp39 24-31 antibody is evaluated initially for direct binding to cell surface gp39 expressed on 50D4, the gp39 CHO transfectant described in Example 5. Supernatants from the G418-resistant h24-31 CHO transfectants that produce immunoglobulin are tested for binding to 50D4 cells and, as negative control, to CHO cells. In this assay 50D4, $1\times10^5$/well, are bound to the bottom of 96 well, poly-L-lysine coated polystyrene plates. The cells are fixed in 0.5% glutaraldehyde in phosphate buffered saline (PBS) for 15 minutes. Plates coated with CHO cells are generated similarly. The cell culture supernatants are added and antibody binding measured using a HRP-conjugated goat anti-human IgG, as described above.

Two assays are used to determine if the humanized 24-31 antibody retains its affinity to gp39 relative to the original murine 24-31 antibody, (i) half-maximal binding concentration and (ii) a competition assay using 50D4 cells. For this purpose the antibodies will be purified on protein A and the concentration of each antibody determined by ELISA by a comparison to isotype matched controls. Half-maximal binding (i) are determined by incubating humanized 24-31 with 50D4 cells at various concentrations from 2 µg/ml to 0.1 ng/ml. The concentration resulting in a half-maximal OD 490 reading, as described above, is compared with the half-maximal binding of murine 24-31. In the competition assay (ii) the humanized 24-31 antibody and the murine 24-31 antibody are mixed in various molar ratios ranging from 100:1 to 1:100, and their ability to compete for binding to 50D4 cells measured. Two sets are run, one where the binding of the humanized antibody will be measured using goat-anti-human IgG (anti-mouse IgG depleted)-HRP and one where the binding of murine antibody is measured using goat-anti-mouse IgG (anti-human IgG depleted)-HRP. Binding curves, one for the murine and one for the humanized antibody, based on molar ratios, are generated and their relative affinities calculated. These assays will confirm the anti-gp39 binding properties of the subject humanized antibodies derived from 24-31.

EXAMPLE 11

Blocking of CD40-Ig Binding to gp39 by Humanized 24-31.

After establishing that humanized anti-gp39 binds to gp39, an assay is effected to confirm that the humanized anti-gp39 retains its ability to block the binding of the ligand to its receptor. For this purpose, activated human peripheral blood T cells, or the gp39-transfected CHO cells, 50D4, are pretreated with graded concentrations of murine 24-31 or with humanized 24-31 for 15 minutes at 4° C. Following this preincubation, CD40-Ig-biotin is added and the binding determined by flow cytometry using PE-avidin. Concentrations of mAbs to achieve a 50% reduction in CD40-Ig binding are determined.

EXAMPLE 12

Blocking of B Cell Proliferation and Differentiation by Humanized 24-31.

To confirm that humanized 24-31 blocks gp39 function, B cells are cultured with a soluble fusion protein of gp39 (gp39-CD8) in the presence or absence of a range of doses of murine 24-31 or humanized 24-31. B cell proliferative response is assessed by $^3$H-thymidine incorporation as shown in FIG. 2A.

T cell dependent B cell differentiation (Ig production) is blocked by mAbs to gp39. To confirm that the subject humanized 24-31 antibodies are effective in blocking the function of native gp39 expressed on the surface of activated human T cells, the ability of the subject humanized 24-31 antibodies inhibit T cell-induced B cell differentiation is assessed. B cells are co-cultured with anti-CD3 activated T cells in the presence or absence of humanized 24-31 and murine 24-31. Polyclonal IgM, IgG, and IgA production is assessed after 12 days (see FIG. 2B). These results will confirm that humanized anti-gp39 can block CD40 binding and interfere with T-cell-dependent B cell activation via CD40.

EXAMPLE 13

Binding Capacity

This experiment was effected to determine the reactivity of the murine, chimeric, and humanized (version 1) 24-31 antibodies to the gp39 antigen relative to the concentration of antibody.

Protocol:

Plate Preparation

1. Add 50 of poly-l-lysine to each well on the 96 well plate. Incubate for 30 minutes at room temperature. Flick plates to remove poly-l-lysine.
2. Wash mgp39-CHO cells (Chinese hamster ovary cells expressing cell surface, membrane gp39) 3 times with HBSS by centrifuging at 1500 rpm for 5 minutes. Resuspend cells in HBSS to $2 \times 10^6$ cells ml.
3. Add 50 µl of cell suspension to each well and centrifuge plates at 2000 rpm for 5 minutes.
4. Add 50 µl/well of ice cold 0.5% glutaraldehyde and incubate for 15 minutes at room temperature.
5. Flick plate and blot to remove excess glutaraldehyde. Add 150 µl/well of 100 mM glycine with 0.1% BSA and incubate for 30 minutes at room temperature. Plates can be used immediately or frozen at −20° C. for future use.

Binding Assay

1. Thaw plate and remove glycine buffer.
2. Serially dilute, 1:2, the test antibodies in dilution buffer starting at 1 µg/ml. Transfer 50 µg/well of each dilution in duplicate. Incubate 2 hours at room temperature.
3. Wash plate 10 times in flowing tap water.
4. Add 50 µl/well of 1:2000 dilution of goat anti-human IgG HRP or goat anti-mouse IgG HRP. Incubate 1 hour at room temperature.
5. Wash plate 10 times in flowing tap water.
6. Add 50 µl/well of ABTS substrate and develop plate for 20–30 minutes. Read the plate at wavelength 405 mn with a background wavelength of 490 run.
7. Plot graph of absorbance vs antibody concentration.

Figure 9:
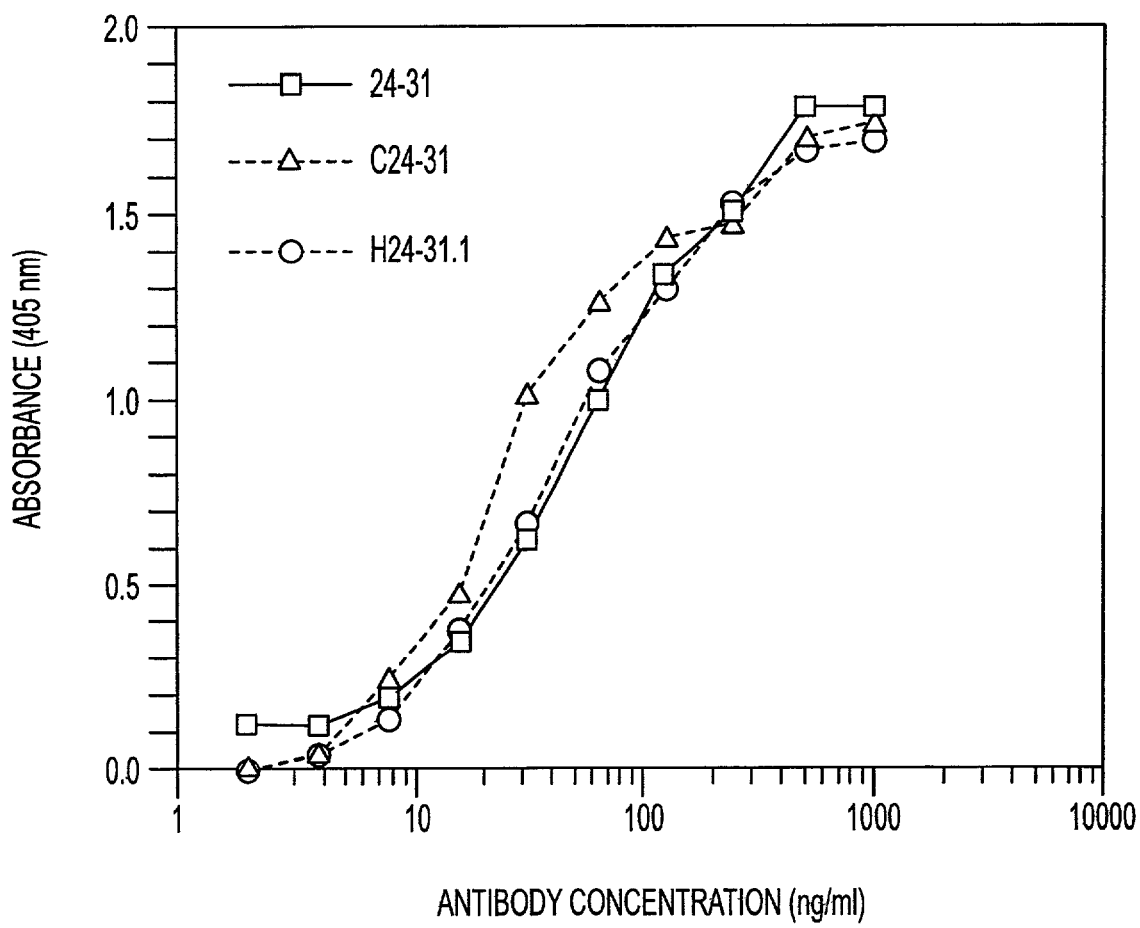
FIG. 9 compares binding of murine 24-31, chimeric 24-31 and a humanized 24-31 antibody to gp39 expressing CHO cells.

Results and Conclusions:

The binding capacities for the three anti-gp39 antibodies (murine, chimeric and humanized version 1 of 24-31) relative to the concentration of the antibodies, were essentially superimposable (see FIG. 9). This is a good indication that these antibodies have similar binding capacities for human gp39, indicating that the humanized antibody has retained the gp39 binding affinity of murine 24-31.

EXAMPLE 14

Competition Between Biotin Labeled Murine 24-31 and Chimeric and Humanized Version 1 24-31

The ability of the chimeric and humanized (version 1) 24-31 antibodies to compete with the murine 24-31 for binding to mgp39-CHO cells basis was evaluated. The ability of the humanized 24-31 to compete with the murine 24-31 for binding to mgp39-CHO was used to evaluate whether in the humanized antibody the exchanges of the murine framework residues with their human counterparts resulted in a significant loss ($\geq 3 \times$ decrease) of affinity.

Protocol:

Plate Preparation
1. Add 50 of poly-1-lysine to each well on the 96 well plate. Incubate for 30 minutes at room temperature. Flick plates to remove poly-l-lysine.
2. Wash mgp39-CHO cells 3 times with HBSS by centrifuging at 1500 rpm for 5 minutes. Resuspend cells in HBSS to $2 \times 10^6$ cells/ml.
3. Add 50 µl of cell suspension to each well and centrifuge plates at 2000 rpm for 5 minutes.
4. Add 50 µl/well of ice cold 0.5% glutaraldehyde and incubate for 15 minutes at room temperature.
5. Flick plate and blot to remove excess glutaraldehyde. Add 150 µl/well of 100 mM glycine with 0.1% BSA and incubate for 30 minutes at room temperature. Plates can be used immediately or frozen at −20° C. for future use.

Competition Assay
1. Thaw plate and remove glycine buffer.
2. Dilute mouse anti-gp39 biotin to 200 ng/ml in PBS with 1% BSA.
3. Serially dilute test antibodies (mouse, chimeric, and humanized 24-31) 1:2 starting at 10 µg/ml in dilution buffer.
4. Transfer 50 µl of diluted test antibodies and mouse anti-gp39 biotin into each well in duplicate. Several wells should contain 50 µl dilution buffer with the mouse anti-gp39 biotin as a maximal control group. Incubate 2 hours at room temperature.
5. Wash plates 10 times in flowing tap water.
6. Add 50 µl/well of 1:2000 dilution of streptavidin HRP and incubate 1 hour at room temperature.
7. Wash plates 10 times in flowing tap water.
8. Add 50 µl/well of ABTS substrate and develop plate for 20–30 minutes. Read the plate at wavelength 405 nm with a background wavelength of 490 nm.
9. Percent inhibition is calculated using the average of the control wells.

Figure 10:
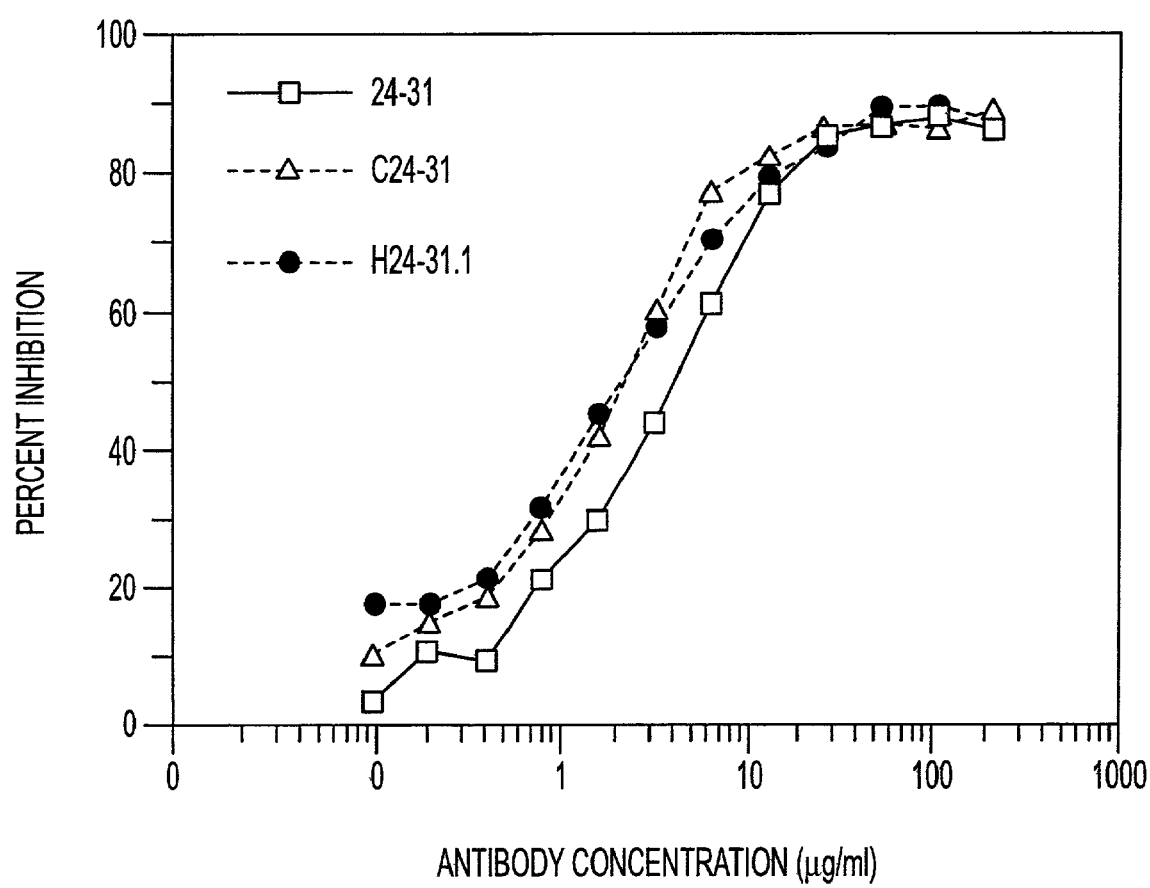
FIG. 10 contains results of a competition assay comparing the binding of 24-31 (biotin) and humanized, chimeric and 24-31 to gp39 expressing CHO cells.

Results and conclusions:
All three antibodies competed equally well with the biotin labeled 24-31 (see FIG. 10). The competition profiles are essentially superimposable at all concentrations, within the limitations of the assay. This demonstrates that the tested humanized antibody (version 1) retains its gp39 binding affinity.

EXAMPLE 15

Modulation of T Cell Dependent B Cell Differentiation
To confirm that the humanized 24-31 retains the in vitro functional activity of murine 24-31, the humanized 24-31 was compared to the murine 24-31 in a "Lipsky" assay. Donor peripheral blood mononuclear cells were separated into two fractions, a T and a B cell fraction. The T cells were first treated with mitomycin C, to prevent mitosis, and then activated with an anti-CD3 antibody. The B cells were added, together with either the murine or humanized (version 1) 24-31 antibodies. A positive control without antibody, and a negative control without B cells were included in the experiment. After a 10 day incubation, the supernatants were tested for the presence of human IgM.

Protocol:
1. Coat a 96 well plate with 50 µl/well of sterile 4 µg/ml anti-CD3 antibody (diluted in 50 mM Tris, pH 9) for 2 hours at 37° C.
2. Selectively purify T and B cells from a buffy coat using Lympho-Kwik reagents. Activate the T cells with 50 µg/ml mitomycin C per $5 \times 10^6$ cells for 30 minutes at 37° C.
3. Wash plate wells several times with sterile HBSS or media to remove non-adherent antibody.
4. Add $1 \times 10^5$ purified T cells ($2 \times 10^6$/ml) to each well.
5. Add $5 \times 10^5$ purified B cells ($5 \times 10^6$/ml) to each well. Add 50 µl anti-gp39 antibody (10–0.1 µg/ml) to each well in quadruplicate. Control wells should include: a) 0 antibody, b) 0 antibody, no T cells, and c) 0 antibody, no B cells.
6. Incubate plate at 37° C./5% $CO_2$ for 12 days.
7. Access cell growth after 7 days using 3H thymidine or any other acceptable method on duplicate wells.
8. After 12 days, collect supernatants from duplicate wells and perform ELISA assays to determine Ig production (IgM).

Figure 11:
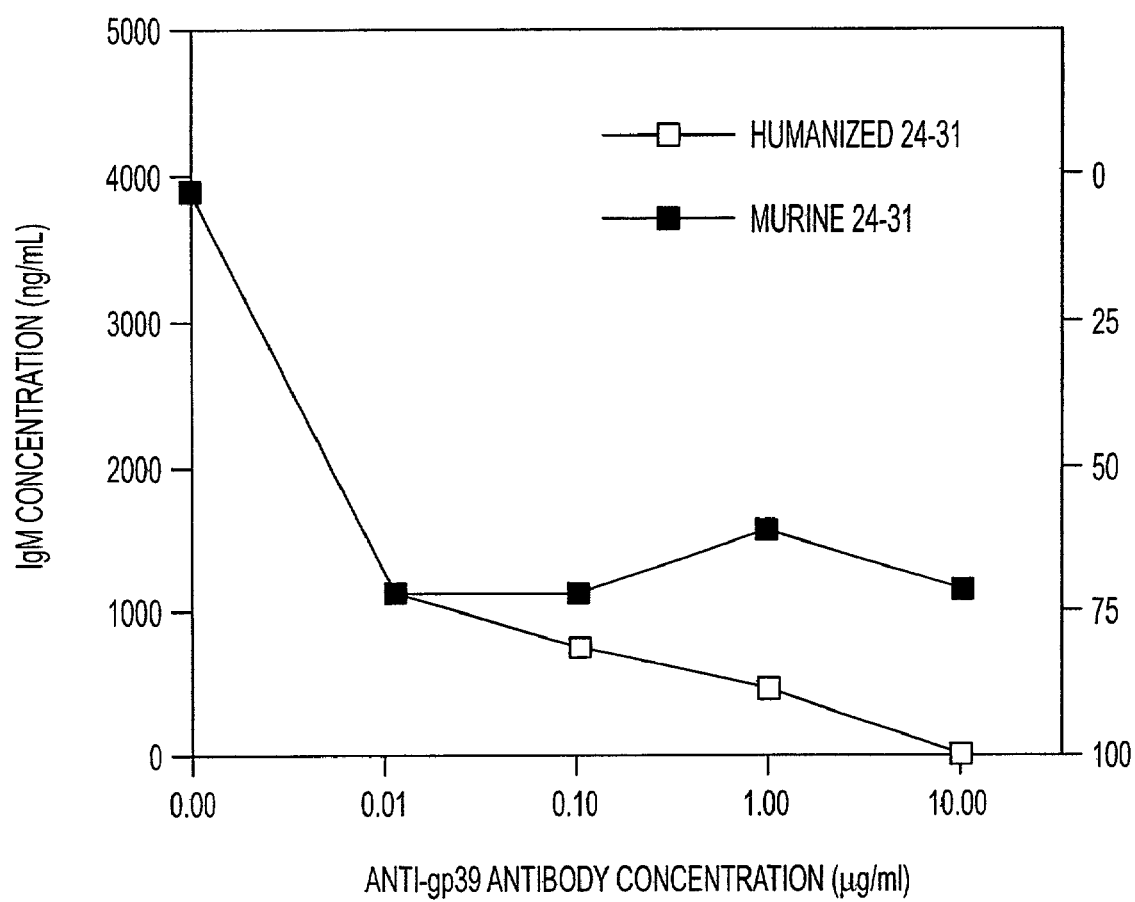
FIG. 11 contains results of an assay which measures effects of murine 24-31 and a humanized 24-31 antibody of the invention on human IgM production by B cells cultured in the presence of mitomycin C treated T cells.

Results and Conclusions:
The results show that the production of human IgM is inhibited 50% by the humanized 24-31 at a concentration below 0.01 µg/ml, similar to the inhibition level obtained with the murine 24-31 (see FIG. 11). The humanized antibody retained its ability to inhibit T cell dependent B cell differentiation (IgM production) in this experiment.

EXAMPLE 16

Evaluation of Humanized 24-31, Version 2
This experiment was conducted to determine whether humanized 24-31 version 2, as compared to version 1, has a similar gp39 binding capacity in a direct binding assay.

Protocol:
Same as in Example 13 above.

Figure 12:
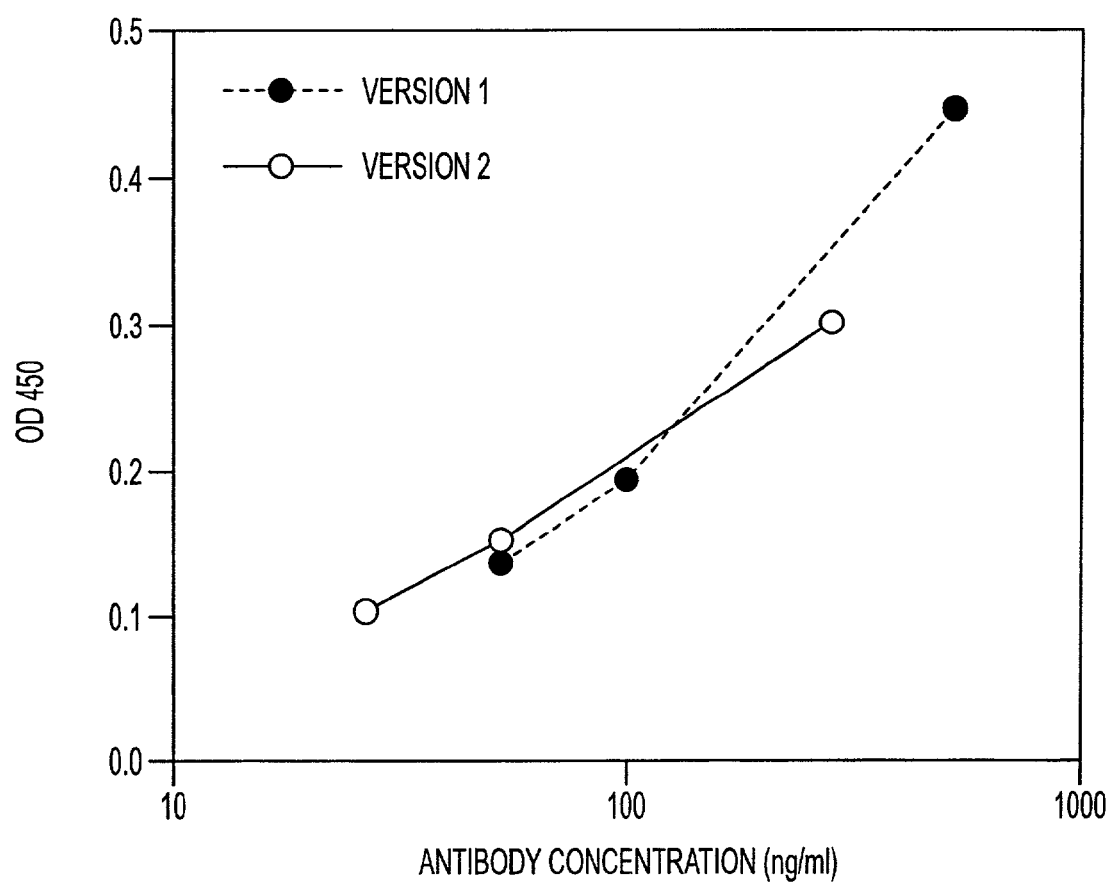
FIG. 12 contains results of an assay comparing binding of two humanized antibodies of the present invention to gp39 expressing CHO cells.

Results and Conclusions.
The results show that the binding capacity of the two 24-31 versions are essentially superimposable (see FIG. 12). This indicates that the two versions have comparable binding activity to gp39.

EXAMPLE 17

This experiment was conducted to measure the Kd of 24-31, and two humanized versions, 1 and 2.

Protocol:
A predetermined amount of each of the three antibodies (murine, version 1 or version 2 24-31) was labeled with $^{125}$I using IODO-BEADS® (Pierce). Antibody bound-$^{125}$I was separated from free $^{125}$I by size separation on a Sephadex-G25/DEAE/Amberlite column.

Direct binding of the $^{125}$I-labeled antibody to murine gp39-CHO cells was tested in a dilution series, in order to determine both counts/pg and the appropriate working concentration (≈half-maximal binding concentration).

$^{125}$I-labeled antibody was mixed and incubated with non-labeled antibody in a dilution series. Based on the total amount of bound antibody and the amount of free antibody, a Scatchard plot was generated from a bound vs. bound-free graph. The total antibody concentration was based on a standard size of 75 kD for one active site.

The Kd was calculated by generating a "best fit" line. The inverse of the slope of the curve is the Kd. The correlation coefficient, $r^2$, was also computed.

Figure 13:
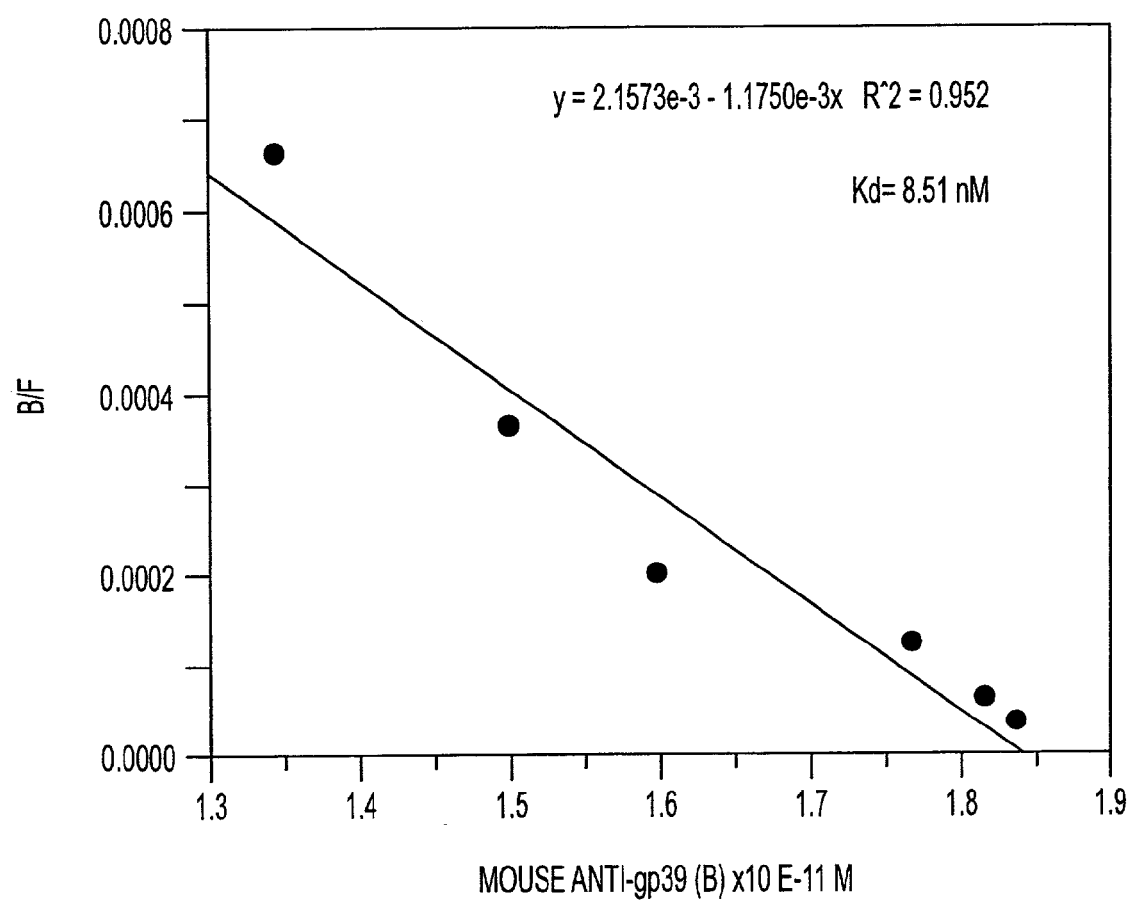
FIG. 13 contains the Scatchard plot for murine 24-31.
Figure 14:
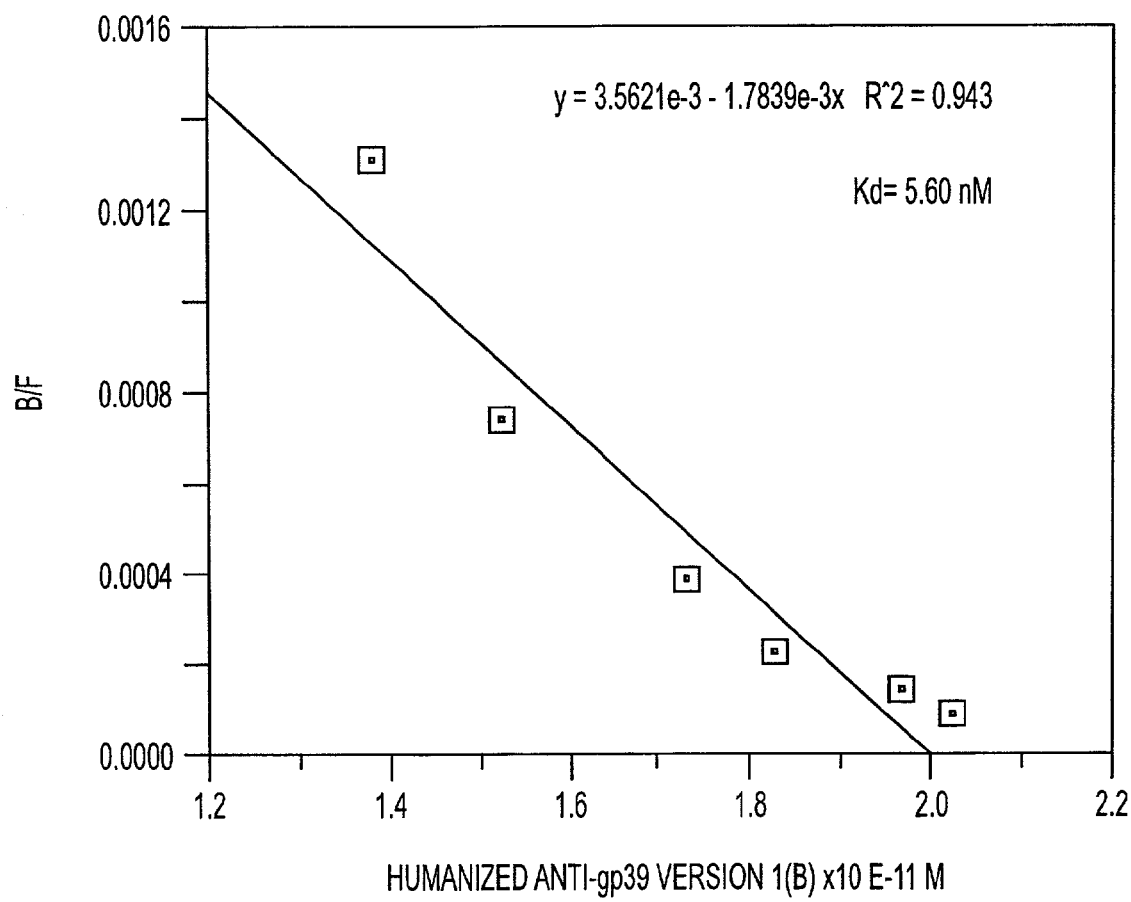
FIG. 14 contains the Scatchard plot for humanized Version 1.
Figure 15:
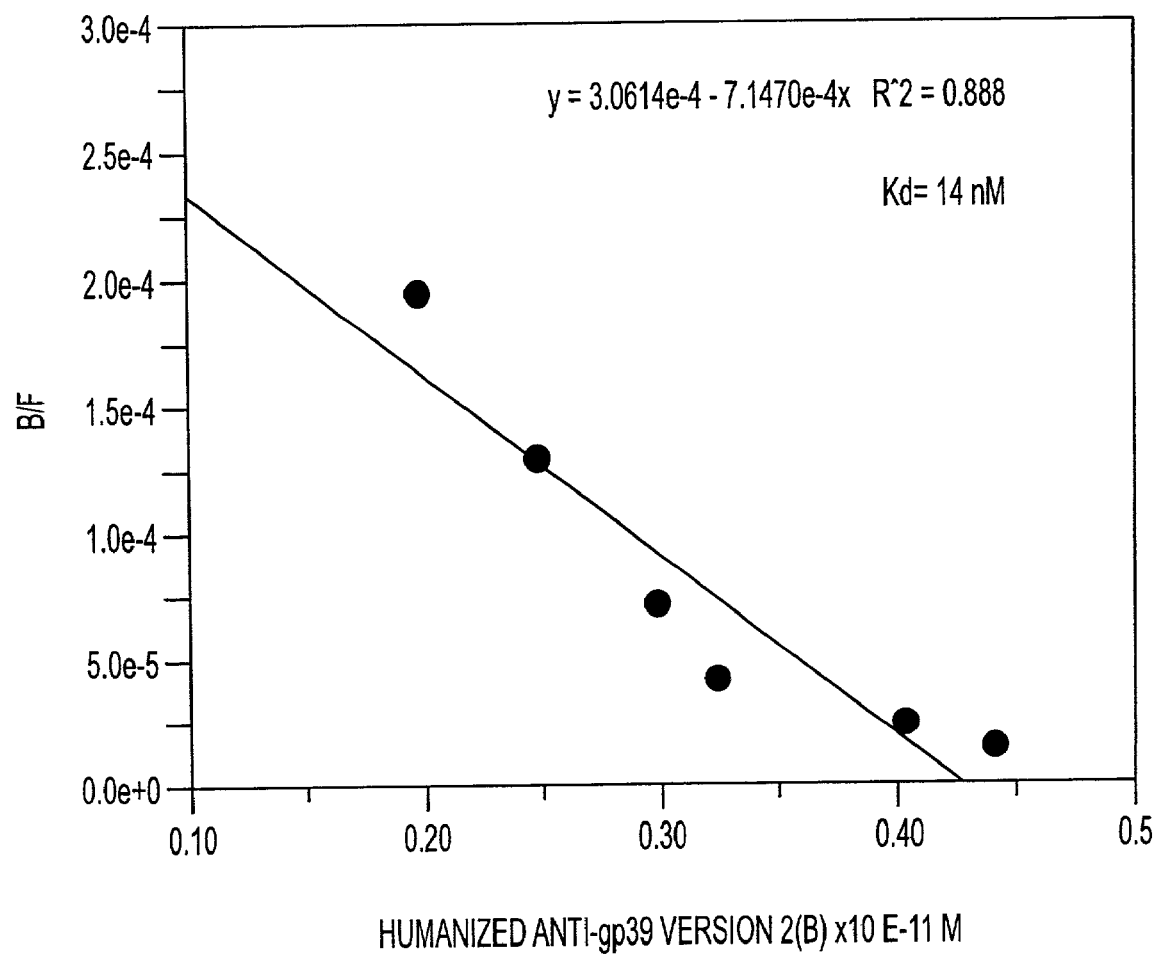
FIG. 15 contains the Scatchard plot for humanized Version 2.

Results:

The Scatchard plots were analyzed. The Kd's from this analysis are: Version 2, Kd=14 nM; murine 24-31, Kd=8.51 nM; version 1, Kd=5.6. The results are depicted in FIGS. 13, 14 and 15, respectively. These results provide further evidence that the subject humanized antibodies bind the gp39 antigen similarly to 24-31.

Use

The humanized anti-gp39 antibodies of the present invention have potential in treating any disease condition wherein gp39 modulation and/or inhibition of the gp39-CD40 interaction is therapeutically beneficial. Moreover, the subject humanized anti-gp39 antibodies may be used in treatment of diseases wherein suppression of antibody responses to antigens are desirable. Such conditions include both autoimmune and non-autoimmune disorders.

The ability of anti-gp39 antibodies to prevent CD40 signaling in B cells is functionally translated into marked inhibition of T cell-dependent antibody responses in vivo. Therefore, autoimmune diseases which are mediated by autoantibody production would be expected to benefit from anti-gp39 antibody therapy. Such diseases include systemic lupus erythematosus, idiopathic thrombocytopenic purpura, myasthenia gravis and a subpopulation of diabetic patients with anti-insulin and anti-insulin receptor antibodies. In addition, CD40 signaling in B cells and dendritic cells is essential for upregulation of co-signaling receptors such as B7.1 and B7.2 molecules. Blocking of this CD40 signaling by anti-gp39 antibodies interferes with antigen presentation to T cells, resulting in inhibition of T cell activation and T cell-mediated responses. The therapeutic efficacy of anti-gp39 antibodies in disease models such as CIA, EAE, NOD mice, GVHD and graft rejection further confirms the antibody's inhibitory effect on T cell-mediated responses. Based on this mechanism of action supported by the efficacy in animal models, the therapeutic potential of the subject humanized anti-gp39 antibodies extend to such diseases as RA, MS, diabetes, psoriasis, GVHD and graft rejection.

Specific conditions which are potentially treatable by administration of the subject humanized antibodies include the following:

Allergic bronchopulmonary aspergillosis; Autoimmune hemolytic anemia; Acanthosis nigricans; Allergic contact dermatitis; Addison's disease; Atopic dermatitis; Alopecia areata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fascitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Graft-vs.-host disease; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatica; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis; Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis; Wiskott-Aldrich syndrome.

Of these, the preferred indications treatable or presentable by administration of anti-gp39 antibodies include autoimmune hemolytic anemia; aplastic anemia; arteritis, temporal; diabetes mellitus; Felty's syndrome; Goodpasture's syndrome; graft-vs-host disease; idiopathic thrombocytopenia pupura; myasthenia gravis; multiple sclerosis; polyarteritis nodosa; psoriasis; psoriatic arthritis; rheumatoid arthritis; systemic lupus erythematosus; asthma; allergic conditions; and transplant rejection.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

The subject anti-gp39 humanized antibodies (or fragments thereof) of this invention are also useful for inducing immunomodulation, e.g., inducing suppression of a human's or animal's immune system. This invention therefore relates to a method of prophylactically or therapeutically inducing immunomodulation in a human or other animal in need thereof by administering an effective, non-toxic amount of such an antibody of this invention to such human or other animal.

The fact that the antibodies of this invention have utility in inducing immunosuppression means that they are useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically mediated diseases (e.g., rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous pemphicjus, Epidermolysis bullosa, urticaria, angioedemas, vasculitides, erythema, cutaneous eosinophilias, Alopecia areata, etc.); the treatment of reversible obstructive airways disease, intestinal inflammations and allergies (e.g., Coeliac disease, proctitis, eosinophilia gastroenteritis, mastocytosis, Crohn's disease and ulcerative colitis) and food-related allergies (e.g., migraine, rhinitis and eczema). Also, the subject antibodies have potential utility for treatment of non-autoimmune conditions wherein immunomodulation is desirable, e.g., graft-versus-host disease (GVHD), transplant rejection, asthma, leukemia, lymphoma, among others.

Also, the subject antibodies can be used as immunosuppressants during cellular or gene therapy. This potentially will enable such cells or gene therapy constructs to be administered repeatedly, or at higher dosages without an adverse immunogenic response.

One skilled in the art would be able, by routine experimentation, to determine what an effective, non-toxic amount of antibody would be for the purpose of inducing immunosuppression. Generally, however, an effective dosage will be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred.

The daily parenteral and oral dosage regimens for employing compounds of the invention to prophylactically or therapeutically induce immunosuppression will generally be in the range of about 0.05 to 100, but preferably about 0.5 to 10, milligrams per kilogram body weight per day.

The antibody of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibody of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as siliceous silicas, and other ingredients such as lanolin, may also be included.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody s or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following are, therefore, to be construed as merely illustrative examples and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5 k by weight of an antibody or fragment thereof of the invention in 10k by volume propylene glycol and water. The solution is sterilized by filtration.

Ointment Composition

Antibody or fragment thereof of the invention 1.0 g.
White soft paraffin to 100.0 g.

The antibody or fragment thereof of the invention is dispersed in a small volume of the vehicle to produce a smooth, homogeneous product. Collapsible metal tubes are then filled with the dispersion.

Topical Cream Composition

Antibody or fragment thereof of the invention 1.0 g.
Polawax GP 200 20.0 g.
Lanolin Anhydrous 2.0 g.
White Beeswax 2.5 g.
Methyl hydroxybenzoate 0.1 g.
Distilled Water to 100.0 g.

The polawax, beeswax and lanolin are heated together at 60° C. A solution of methyl hydroxybenzoate is added and homogenization is achieved using high speed stirring. The temperature is then allowed to fall to SOOC. The antibody or fragment thereof of the invention is then added and dispersed throughout, and the composition is allowed to cool with slow speed stirring.

Topical Lotion Composition

Antibody or fragment thereof of the invention 1.0 g.
Sorbitan Monolaurate 0.6 g. Polysorbate 20 0.6 g.
Cetostearyl Alcohol 1.2 g. Glycerin 6.0 g.
Methyl Hydroxybenzoate 0.2 g.
Purified Water B.P. to 100.00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition

Antibody or fragment thereof of the invention 0.5 g.
Methyl Hydroxybenzoate 0.01 g.
Propyl Hydroxybenzoate 0.04 g.
Purified Water B.P. to 100.00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 Am pore size), and packed aseptically into suitable sterile containers.

Composition for Administration by Inhalation

For an aerosol container with a capacity of 15–20 ml: mix 10 mg. of an antibody or fragment thereof of the invention with 0.2–0.5 k of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration. Composition for Administration by Inhalation For an aerosol container with a capacity of 15–20 ml: dissolve 10 mg. of an antibody or fragment thereof of the invention in ethanol (6–8 ml.), add 0.1–0.2k of a lubricating agent, such as polysorbate 85 or oleic acid; and disperse such in a propellant, such as freon, preferably in combination of (1–2 dichlorotetrafluoroethane) and difluorochloromethane, and put into an appropriate aerosol container adapted for either intranasal or oral inhalation administration.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4k saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical formulation can vary widely, i.e., from less than about 0.5k, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg. of an antibody or fragment thereof of the invention. Similarly, a pharmaceutical composition of the invention for intravenous infusion could be made up to contain 250 ml. of sterile Ringer's solution, and 150 mg. of an antibody or fragment thereof of the invention. Actual methods for preparing parenterally administrable compositions are well-known or will be apparent to those skilled in the art, and are described in more detail in, e.g., *Remington's Pharmaceutical Science,* 15th ed., Mack Publishing Company, Easton, Pa., hereby incorporated by reference herein.

The antibodies (or fragments thereof) of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the altered antibodies (or fragments thereof) of the invention sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al, *Science,* 253:792–795 (1991).

From the foregoing, it will be appreciated that, although specific embodiments of the invention have been described herein for purposes of illustration, various modifications may be made without diverting from the scope of the invention. Accordingly, the invention is not limited by the appended claims.

What is claimed is:

1. A method of treating an autoimmune disorder comprising administering a therapeutically effective amount of a humanized antibody or antigen binding fragment that specifically binds CD40 ligand that contains a variable light sequence which comprises the amino acid sequence encoded by SEQ ID NO: 24 or SEQ ID NO: 25 and a variable heavy sequence which comprises the amino acid sequence encoded by the nucleic acid sequence SEQ ID NO: 26, wherein said autoimmune disorder is selected from the group consisting of diabetes mellitus, psoriasis, autoimmune glomerulonephritis, autoimmune hemolytic anemia, Addison's disease, autoimmune oophoritis, autoimmune orchitis, autoimmune polyendocrine failure, Behcet' disease, Berger's disease; Buerger's disease, bullous pemphigus, celiac sprue, Graves disease, Goodpasture's Syndrome, Hashimato's thyroiditis, chronic active hepatitis, chronic progressive hepatitis, idiopathic thrombocytopenia purpura, Job's syndrome, psoriatic arthritis, rheumatoid arthritis, Kawasaki's disease, multiple sclerosis, myasthenia gravis, pemphigoid, pemphigus, pemphigus erythematosus, pemphigus foliaceus, pemphigus vulgaris, polymyalgia rheumatica, pulmonary fibrosis, Reiter's syndrome, Reidel's thyroiditis, rheumatic fever, sarcoidosis, Sezary syndrome; Scleroderma, ulcerative colitis, autoimmune hemolytic anemia, Felty's syndrome, systemic lupus erythematosus, discoid lupus erythematosus, autoimmune polyarteritis nodosa, Caplan's syndrome, Crohn's disease, psoriasis, Sjogren's syndrome, Crest syndrome, and Wiscott-Aldrich syndrome.

2. The method of claim 1 where the autoimmune disease is rheumatoid arthritis or psoriatic arthritis.

3. The method of claim 1 wherein the humanized antibody or fragment has the variable region encoded by SEQ ID NO: 24.

4. The method of claim 1 wherein the humanized antibody has a human constant region selected from the group consisting of gamma 1, gamma 2, gamma 3, gamma 4 and mutated versions that provide for altered effector function.

5. The method of claim 4 wherein the human constant region is a mutated gamma 4 containing one or both of the following mutations:
   (i) change of a leucine to a glutamic acid at position 236; and
   (ii) change of a serine to a proline at position 229.

6. The method of claim 1 wherein the humanized antibody contains a human kappa or lambda constant region.

7. The method of claim 1 wherein the dosage of humanized antibody or fragment administered ranges from 0.05 to 100 mg per kilogram of body weight per day.

8. The method of claim 1 wherein the antibody or fragment is administered parentally.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

```
Asp Ile Val Met Thr Gln Ser Pro Ser Phe Leu Ser Ala Ser Val Gly
1               5                  10                  15

Asp Arg Val Thr Ile Thr Cys Lys Ala Ser Gln Asn Val Ile Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Tyr
                85                  90                  95

Thr Phe Gly Gly Gly Thr Lys Leu Glu Ile Lys
                100                 105
```

(2) INFORMATION FOR SEQ ID NO: 2:

(i) SEQUENCE CHARACTERISTICS:
    (A) LENGTH: 107 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 2:

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asn Val Ile Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Asp Tyr Phe Cys Gln Gln Tyr Asn Ser Tyr Pro Tyr
                85                  90                  95

Thr Phe Gly Gly Gly Thr Lys Leu Glu Ile Lys
            100                 105
```

(2) INFORMATION FOR SEQ ID NO: 3:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Asp Ile Val Met Thr Gln Ser Pro Ser Phe Met Ser Thr Ser Val Gly
1               5                   10                  15

Asp Arg Val Thr Ile Thr Cys Lys Ala Ser Gln Asn Val Ile Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Met Gln Pro
65                  70                  75                  80

Glu Asp Phe Ala Asp Tyr Phe Cys Gln Gln Tyr Asn Ser Tyr Pro Tyr
                85                  90                  95

Thr Phe Gly Gly Gly Thr Lys Leu Glu Ile Lys
            100                 105
```

(2) INFORMATION FOR SEQ ID NO: 4:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Asp Ile Val Met Thr Gln Ser Pro Asp Ser Met Ala Thr Ser Leu Gly

```
            1               5                  10                 15
Glu Arg Val Thr Ile Asn Cys Lys Ala Ser Gln Asn Val Ile Thr Ala
                20                  25                  30

Val Ala Trp Tyr Gln Gln Lys Pro Gly Gln Ser Pro Lys Leu Leu Ile
                35                  40                  45

Tyr Ser Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Met Gln Ala
65                  70                  75                  80

Glu Asp Val Ala Asp Tyr Phe Cys Gln Gln Tyr Asn Ser Tyr Pro Tyr
                85                  90                  95

Thr Phe Gly Gly Gly Thr Lys Leu Glu Ile Lys
                100                 105
```

(2) INFORMATION FOR SEQ ID NO: 5:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Asn Gly
                20                  25                  30

Phe Trp Ile Trp Ile Arg Lys Pro Pro Gly Asn Lys Leu Glu Tyr Met
                35                  40                  45

Gly Tyr Ile Ser Tyr Ser Gly Ser Thr Tyr Tyr Asn Pro Ser Leu Lys
        50                  55                  60

Ser Arg Ile Ser Ile Ser Arg Asp Thr Ser Lys Asn Gln Phe Ser Leu
65                  70                  75                  80

Lys Leu Ser Ser Val Thr Ala Ala Asp Thr Gly Val Tyr Tyr Cys Ala
                85                  90                  95

Cys Arg Ser Tyr Gly Arg Thr Pro Tyr Tyr Phe Asp Phe Trp Gly Gln
                100                 105                 110

Gly Thr Thr Leu Thr Val Ser Ser
        115                 120
```

(2) INFORMATION FOR SEQ ID NO: 6:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Asn Gly
                20                  25                  30

Phe Trp Ile Trp Ile Arg Lys His Pro Gly Asn Lys Leu Glu Tyr Met
                35                  40                  45
```

```
Gly Tyr Ile Ser Tyr Ser Gly Ser Thr Tyr Tyr Asn Pro Ser Leu Lys
        50                   55                  60

Ser Arg Ile Ser Ile Ser Arg Asp Thr Ser Lys Asn Gln Phe Ser Leu
65                   70                  75                  80

Lys Leu Ser Ser Val Thr Ala Ala Asp Thr Gly Val Tyr Tyr Cys Ala
                    85                  90                  95

Cys Arg Ser Tyr Gly Arg Thr Pro Tyr Tyr Phe Asp Phe Trp Gly Gln
                100                 105                 110

Gly Thr Thr Leu Thr Val Ser Ser
                115                 120

(2) INFORMATION FOR SEQ ID NO: 7:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Glu Val Gln Leu Gln Glu Ser Gly Pro Gly Leu Val Lys Pro Ser Gln
1               5                   10                  15

Thr Leu Ser Leu Thr Cys Ala Val Ser Gly Asp Ser Ile Thr Asn Gly
                20                  25                  30

Phe Trp Ile Trp Ile Arg Lys His Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Ser Arg Asp Thr Ser Asn Asn Gln Phe Ser Leu
65                  70                  75                  80

Asn Leu Asn Ser Val Thr Arg Ala Asp Thr Gly Val Tyr Tyr Cys Ala
                    85                  90                  95

Cys Arg Ser Tyr Gly Arg Thr Pro Tyr Tyr Phe Asp Phe Trp Gly Gln
                100                 105                 110

Gly Thr Thr Leu Thr Val Ser Ser
                115                 120

(2) INFORMATION FOR SEQ ID NO: 8:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Glu Val Gln Leu Gln Glu Ser Gly Pro Gly Leu Val Lys Pro Ser Glu
1               5                   10                  15

Thr Leu Ser Leu Thr Cys Ala Val Tyr Gly Asp Ser Ile Thr Asn Gly
                20                  25                  30

Phe Trp Ile Trp Ile Arg Lys Pro Pro Gly Asn Lys Leu Glu Tyr Met
            35                  40                  45

Gly Tyr Ile Ser Tyr Ser Gly Ser Thr Tyr Tyr Asn Pro Ser Leu Lys
        50                  55                  60

Ser Arg Ile Ser Ile Ser Arg Asp Thr Ser Lys Asn Gln Phe Tyr Leu
65                  70                  75                  80
```

```
Lys Leu Ser Ser Val Thr Ala Ala Asp Thr Gly Val Tyr Tyr Cys Ala
                85                  90                  95

Cys Arg Ser Tyr Gly Arg Thr Pro Tyr Tyr Phe Asp Phe Trp Gly Gln
            100                 105                 110

Gly Thr Thr Leu Thr Val Ser Ser
        115                 120

(2) INFORMATION FOR SEQ ID NO: 9:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Asp Ile Gln Met Thr Gln Ser Pro Ser Phe Leu Ser Ala Ser Val Gly
1               5                  10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
            35                  40                  45

Ser Gly Thr Asp Phe Thr Leu Thr Ile Ser Ser Leu Gln Pro Glu Asp
        50                  55                  60

Phe Ala Thr Tyr Tyr Cys
65                  70

(2) INFORMATION FOR SEQ ID NO: 10:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Asp Ile Gln Met Thr Gln Ser Pro Ser Thr Leu Ser Ala Ser Val Gly
1               5                  10                  15

Asp Arg Val Thr Ile Thr Cys Trp Tyr Gln Gln Lys Pro Gly Glu Ala
            20                  25                  30

Pro Lys Val Leu Ile Tyr Gly Val Pro Ser Arg Phe Ser Gly Ser Gly
            35                  40                  45

Ser Gly Thr Glu Phe Thr Leu Thr Ile Ser Ser Leu Gln Ser Asp Asp
        50                  55                  60

Phe Ala Thr Tyr Tyr Cys Phe Gly Gln Gly Thr Lys Leu Glu Ile Lys
65                  70                  75                  80

(2) INFORMATION FOR SEQ ID NO: 11:

(i) SEQUENCE CHARACTERISTICS:
        (A) LENGTH: 81 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:
```

-continued

```
Asp Ile Val Met Thr Gln Ser Gln Lys Phe Met Ser Thr Val Gly
1               5                   10                  15

Asp Arg Val Ser Ile Thr Cys Trp Tyr Gln Gln Lys Pro Gly Gln Ser
                20                  25                  30

Pro Lys Ile Leu Leu Ile Tyr Gly Val Pro Asp Arg Phe Ser Gly Ser
            35                  40                  45

Gly Ser Gly Thr Asp Phe Thr Leu Thr Ile Ser Asn Met Gln Ser Glu
    50                  55                  60

Asp Leu Ala Asp Tyr Phe Cys Phe Gly Gly Gly Thr Lys Leu Glu Ile
65                  70                  75                  80

Lys
```

(2) INFORMATION FOR SEQ ID NO: 12:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

```
Asp Ile Val Met Thr Gln Ser Pro Ser Phe Leu Ser Ala Ser Val Gly
1               5                   10                  15

Asp Arg Val Thr Ile Thr Cys Trp Tyr Gln Gln Lys Pro Gly Lys Ser
                20                  25                  30

Pro Lys Leu Leu Ile Tyr Gly Val Pro Asp Arg Phe Ser Gly Ser Gly
            35                  40                  45

Ser Gly Thr Asp Phe Thr Leu Thr Ile Ser Ser Leu Gln Pro Glu Asp
    50                  55                  60

Phe Ala Asp Tyr Phe Cys Phe Gly Gly Gly Thr Lys Leu Glu Ile Lys
65                  70                  75                  80
```

(2) INFORMATION FOR SEQ ID NO: 13:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

```
Asp Ile Val Met Thr Gln Ser Pro Asp Ser Leu Ala Val Ser Leu Gly
1               5                   10                  15

Glu Arg Ala Thr Ile Asn Cys Trp Tyr Gln Gln Lys Pro Gly Gln Pro
                20                  25                  30

Pro Lys Leu Leu Ile Tyr Gly Val Pro Asp Arg Phe Ser Gly Ser Gly
            35                  40                  45

Ser Gly Thr Asp Phe Thr Leu Thr Ile Ser Ser Leu Gln Ala Glu Asp
    50                  55                  60

Val Ala Val Tyr Tyr Cys Phe Gly Gln Gly Thr Lys Leu Glu Ile Lys
65                  70                  75                  80
```

(2) INFORMATION FOR SEQ ID NO: 14:

(i) SEQUENCE CHARACTERISTICS:
        (A) LENGTH: 79 amino acids
        (B) TYPE: amino acid (C) STRANDEDNESS: single
        (D) TOPOLOGY: linear (ii) MOLECULE TYPE: protein (xi) SEQUENCE DESCRIPTION: SEQ ID NO: 14:

Asp Ile Val Met Thr Gln Ser Gln Lys Met Ser Thr Ser Val Gly Asp
1               5                  10                  15

Arg Val Ser Ile Thr Cys Trp Tyr Gln Gln Lys Pro Gly Gln Ser Pro
            20                  25                  30

Lys Leu Leu Ile Tyr Gly Val Pro Asp Arg Phe Ser Gly Ser Gly Ser
        35                  40                  45

Gly Thr Asp Phe Thr Leu Thr Ile Ser Asn Met Gln Ser Glu Asp Leu
    50                  55                  60

Ala Asp Tyr Phe Cys Phe Gly Gly Gly Thr Lys Leu Glu Ile Lys
65                  70                  75

(2) INFORMATION FOR SEQ ID NO: 15:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Asp Ile Val Met Thr Gln Ser Pro Asp Ser Leu Ala Val Ser Leu Gly
1               5                  10                  15

Glu Arg Ala Thr Ile Asn Cys Trp Tyr Gln Gln Lys Pro Gly Gln Ser
            20                  25                  30

Pro Lys Leu Leu Ile Tyr Gly Val Pro Asp Arg Phe Ser Gly Ser Gly
        35                  40                  45

Ser Gly Thr Asp Phe Thr Leu Thr Ile Ser Ser Leu Gln Ala Glu Asp
    50                  55                  60

Val Ala Asp Tyr Phe Cys Phe Gly Gly Gly Thr Lys Leu Glu Ile Lys
65                  70                  75                  80

(2) INFORMATION FOR SEQ ID NO: 16:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Gln Val Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Trp Ile
            20                  25                  30

Arg Gln Pro Pro Gly Lys Gly Leu Glu Trp Ile Gly Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Met Val Thr Val Ser Ser

85

(2) INFORMATION FOR SEQ ID NO: 17:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

```
Glu Val Gln Leu Gln Glu Ser Gly Pro Gly Ser Val Lys Pro Ser Gln
1               5                   10                  15

Thr Leu Ser Leu Thr Cys Ser Val Thr Gly Asp Ser Ile Thr Trp Ile
            20                  25                  30

Arg Lys Phe Pro Gly Asn Lys Leu Glu Tyr Met Gly Arg Ile Ser Ile
        35                  40                  45

Thr Arg Asp Thr Ser Gln Asn Gln Phe Tyr Leu Gln Leu Asn Ser Val
    50                  55                  60

Thr Thr Glu Asp Thr Gly Thr Tyr Tyr Cys Ala Cys Trp Gly Gln Gly
65                  70                  75                  80

Thr Thr Leu Thr Val Ser Ser
            85
```

(2) INFORMATION FOR SEQ ID NO: 18:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Trp Ile
            20                  25                  30

Arg Lys Pro Pro Gly Asn Lys Leu Glu Tyr Met Gly Arg Ile Ser Ile
        35                  40                  45

Ser Arg Asp Thr Ser Lys Asn Gln Phe Ser Leu Lys Leu Ser Ser Val
    50                  55                  60

Thr Ala Ala Asp Thr Gly Val Tyr Tyr Cys Ala Cys Trp Gly Gln Gly
65                  70                  75                  80

Thr Thr Leu Thr Val Ser Ser
            85
```

(2) INFORMATION FOR SEQ ID NO: 19:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

```
Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Ser Trp Ile
            20                  25                  30

Arg Gln Pro Ala Gly Lys Gly Leu Glu Trp Ile Gly Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Met Val Thr Val Ser Ser
                85

(2) INFORMATION FOR SEQ ID NO: 20:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Trp Ile
            20                  25                  30

Arg Gln His Pro Gly Lys Gly Leu Glu Trp Ile Gly Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Thr Leu Thr Val Ser Ser
                85

(2) INFORMATION FOR SEQ ID NO: 21:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Trp Ile
            20                  25                  30

Arg Lys His Pro Gly Asn Lys Leu Glu Tyr Met Gly Arg Ile Ser Ile
        35                  40                  45

Ser Arg Asp Thr Ser Lys Asn Gln Phe Ser Leu Lys Leu Ser Ser Val
    50                  55                  60

Thr Ala Ala Asp Thr Gly Val Tyr Tyr Cys Ala Cys
65                  70                  75

(2) INFORMATION FOR SEQ ID NO: 22:

(i) SEQUENCE CHARACTERISTICS:
```

(A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 30
        (D) OTHER INFORMATION: /note= "Nucleotide 30 wherein N =
            (Ck)."

(xi) SEQUENCE DESCRIPTION: SEQ ID NO: 22:

TGCAGCATCC GTACGTTTGA TTCCAGCTTN                                  30

(2) INFORMATION FOR SEQ ID NO: 23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 20
        (D) OTHER INFORMATION: /note= "Nucleotide 20 wherein N = A
            or C."

(ix) FEATURE:
        (A) NAME/KEY: misc_feature
        (B) LOCATION: 21
        (D) OTHER INFORMATION: /note= "Nucleotide 21 wherein N = G
            or A."

(ix) FEATURE:
        (A) NAME/KEY: misc_feature
        (B) LOCATION: 27
        (D) OTHER INFORMATION: /note= "Nucleotide 27 wherein N = G
            or A."

(ix) FEATURE:
        (A) NAME/KEY: misc_feature
        (B) LOCATION: 32
        (D) OTHER INFORMATION: /note= "Nucleotide 32 wherein N = C
            gamma 1."

(xi) SEQUENCE DESCRIPTION: SEQ ID NO: 23:

GGGGGTGTCG TGCTAGCTGN NGAGACNGTG AN                              32

(2) INFORMATION FOR SEQ ID NO: 24:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 13..411

(xi) SEQUENCE DESCRIPTION: SEQ ID NO: 24:

AGATCTCTCA CC ATG GGC TTC AAG ATG GAG TCA CAG TTT CTG GCC TTT     48
              Met Gly Phe Lys Met Glu Ser Gln Phe Leu Ala Phe
                1               5                  10

GTA TTC GCG TTT CTC TGG TTG TCT GGT GTT GAT GGA GAC ATT GTG ATG   96
Val Phe Ala Phe Leu Trp Leu Ser Gly Val Asp Gly Asp Ile Val Met

```
              15                  20                  25
ACC CAG TCT CCA TCT TTC CTC TCC GCC TCC GTA GGA GAC AGG GTC ACC        144
Thr Gln Ser Pro Ser Phe Leu Ser Ala Ser Val Gly Asp Arg Val Thr
         30                  35                  40

ATC ACC TGC AAG GCC AGT CAG AAT GTG ATT ACT GCT GTA GCC TGG TAT        192
Ile Thr Cys Lys Ala Ser Gln Asn Val Ile Thr Ala Val Ala Trp Tyr
 45                  50                  55                  60

CAA CAG AAA CCA GGA AAG TCT CCT AAA TTG CTG ATT TAC TCG GCA TCC        240
Gln Gln Lys Pro Gly Lys Ser Pro Lys Leu Leu Ile Tyr Ser Ala Ser
                 65                  70                  75

AAT CGG TAC ACT GGA GTC CCT GAT CGC TTC TCA GGC AGT GGG TCT GGG        288
Asn Arg Tyr Thr Gly Val Pro Asp Arg Phe Ser Gly Ser Gly Ser Gly
             80                  85                  90

ACA GAT TTC ACT CTC ACC ATC AGC TCT CTC CAG CCA GAA GAC TTC GCA        336
Thr Asp Phe Thr Leu Thr Ile Ser Ser Leu Gln Pro Glu Asp Phe Ala
         95                  100                 105

GAT TAT TTC TGC CAG CAA TAT AAC AGC TAT CCG TAC ACG TTC GGA GGG        384
Asp Tyr Phe Cys Gln Gln Tyr Asn Ser Tyr Pro Tyr Thr Phe Gly Gly
     110                 115                 120

GGG ACC AAG CTG GAA ATC AAA CGT ACG                                    411
Gly Thr Lys Leu Glu Ile Lys Arg Thr
125                 130

(2) INFORMATION FOR SEQ ID NO: 25:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 13..411

(xi) SEQUENCE DESCRIPTION: SEQ ID NO: 25:

AGATCTCTCA CC ATG GGC TTC AAG ATG GAG TCA CAG TTT CTG GCC TTT          48
              Met Gly Phe Lys Met Glu Ser Gln Phe Leu Ala Phe
              135                 140                 145

GTA TTC GCG TTT CTC TGG TTG TCT GGT GTT GAT GGA GAC ATT GTG ATG        96
Val Phe Ala Phe Leu Trp Leu Ser Gly Val Asp Gly Asp Ile Val Met
                 150                 155                 160

ACC CAG TCT CCA GAT TCT CTC GCC GTG TCC CTC GGA GAG AGG GCC ACC        144
Thr Gln Ser Pro Asp Ser Leu Ala Val Ser Leu Gly Glu Arg Ala Thr
                 165                 170                 175

ATC AAC TGC AAG GCC AGT CAG AAT GTG ATT ACT GCT GTA GCC TGG TAT        192
Ile Asn Cys Lys Ala Ser Gln Asn Val Ile Thr Ala Val Ala Trp Tyr
             180                 185                 190

CAA CAG AAA CCA GGA CAA TCT CCT AAA TTG CTG ATT TAC TCG GCA TCC        240
Gln Gln Lys Pro Gly Gln Ser Pro Lys Leu Leu Ile Tyr Ser Ala Ser
        195                 200                 205

AAT CGG TAC ACT GGA GTC CCT GAT CGC TTC TCA GGC AGT GGG TCT GGG        288
Asn Arg Tyr Thr Gly Val Pro Asp Arg Phe Ser Gly Ser Gly Ser Gly
210                 215                 220                 225

ACA GAT TTC ACT CTC ACC ATC AGC TCT CTC CAG GCC GAA GAC GTG GCA        336
Thr Asp Phe Thr Leu Thr Ile Ser Ser Leu Gln Ala Glu Asp Val Ala
                230                 235                 240

GAT TAT TTC TGC CAG CCA TAT AAC AGC TAT CCG TAC ACG TTC GGA GGG        384
Asp Tyr Phe Cys Gln Pro Tyr Asn Ser Tyr Pro Tyr Thr Phe Gly Gly
            245                 250                 255
```

```
GGG ACC AAG CTG GAA ATC AAA CGT ACG                                  411
Gly Thr Lys Leu Glu Ile Lys Arg Thr
        260                 265

(2) INFORMATION FOR SEQ ID NO: 26:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 7..426

(xi) SEQUENCE DESCRIPTION: SEQ ID NO: 26:

GTCGAC ATG ATG GTG TTA AGT CTT CTG TAC CTG TTG ACA GCC CTT CCG        48
       Met Met Val Leu Ser Leu Leu Tyr Leu Leu Thr Ala Leu Pro
        1               5                  10

GGT TTC CTG TCA GAG GTG CAG CTT CAG GAG TCA GGA CCT GGC CTC GTG       96
Gly Phe Leu Ser Glu Val Gln Leu Gln Glu Ser Gly Pro Gly Leu Val
 15                  20                  25                  30

AAA CCT TCT GAG ACT CTG TCC CTC ACC TGT ACC GTC TCT GGC GAC TCC       144
Lys Pro Ser Glu Thr Leu Ser Leu Thr Cys Thr Val Ser Gly Asp Ser
                 35                  40                  45

ATC ACT AAT GGT TTC TGG ATC TGG ATC CGG AAA CCA CCA GGG AAT AAA       192
Ile Thr Asn Gly Phe Trp Ile Trp Ile Arg Lys Pro Pro Gly Asn Lys
                     50                  55                  60

CTT GAG TAC ATG GGC TAC ATA AGT TAC AGT GGT AGC ACT TAC TAC AAT       240
Leu Glu Tyr Met Gly Tyr Ile Ser Tyr Ser Gly Ser Thr Tyr Tyr Asn
             65                  70                  75

CCA TCT CTC AAG AGT CGA ATC TCC ATC TCT CGC GAC ACA TCC AAG AAC       288
Pro Ser Leu Lys Ser Arg Ile Ser Ile Ser Arg Asp Thr Ser Lys Asn
 80                  85                  90

CAG TTC TCT CTA AAG TTG TCT TCT GTG ACT GCC GCC GAC ACA GGC GTG       336
Gln Phe Ser Leu Lys Leu Ser Ser Val Thr Ala Ala Asp Thr Gly Val
 95                  100                 105                 110

TAT TAC TGT GCC TGC CGC AGT TAC GGG AGG ACC CCG TAC TAC TTT GAC       384
Tyr Tyr Cys Ala Cys Arg Ser Tyr Gly Arg Thr Pro Tyr Tyr Phe Asp
                 115                 120                 125

TTC TGG GGC CAA GGC ACC ACT CTC ACC GTC TCC TCA GCT AGC               426
Phe Trp Gly Gln Gly Thr Thr Leu Thr Val Ser Ser Ala Ser
                 130                 135                 140

(2) INFORMATION FOR SEQ ID NO: 27:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 13..411

(xi) SEQUENCE DESCRIPTION: SEQ ID NO: 27:

AGATCTCTCA CC ATG GGC TTC AAG ATG GAG TCA CAG TTT CTG GCC TTT         48
              Met Gly Phe Lys Met Glu Ser Gln Phe Leu Ala Phe
              135                 140                 145

GTA TTC GCG TTT CTC TGG TTG TCT GGT GTT GAT GGA GAC ATT GTG ATG       96
```

```
Val Phe Ala Phe Leu Trp Leu Ser Gly Val Asp Gly Asp Ile Val Met
            150                 155                 160

ACC CAG TCT CAA AAA TTC ATG TCC ACA TCC GTA GGA GAC AGG GTC AGC         144
Thr Gln Ser Gln Lys Phe Met Ser Thr Ser Val Gly Asp Arg Val Ser
            165                 170                 175

ATC ACC TGC AAG GCC AGT CAG AAT GTG ATT ACT GCT GTA GCC TGG TAT         192
Ile Thr Cys Lys Ala Ser Gln Asn Val Ile Thr Ala Val Ala Trp Tyr
            180                 185                 190

CAA CAG AAA CCA GGA CAA TCT CCT AAA TTG CTG ATT TAC TCG GCA TCC         240
Gln Gln Lys Pro Gly Gln Ser Pro Lys Leu Leu Ile Tyr Ser Ala Ser
            195                 200                 205

AAT CGG TAC ACT GGA GTC CCT GAT CGC TTC TCA GGC AGT GGG TCT GGG         288
Asn Arg Tyr Thr Gly Val Pro Asp Arg Phe Ser Gly Ser Gly Ser Gly
210                 215                 220                 225

ACA GAT TTC ACT CTC ACC ATC AGC AAT ATG CAG TCT GAA GAC CTG GCA         336
Thr Asp Phe Thr Leu Thr Ile Ser Asn Met Gln Ser Glu Asp Leu Ala
            230                 235                 240

GAT TAT TTC TGC CAG CAA TAT AAC AGC TAT CCG TAC ACG TTC GGA GGG         384
Asp Tyr Phe Cys Gln Gln Tyr Asn Ser Tyr Pro Tyr Thr Phe Gly Gly
            245                 250                 255

GGG ACC AAG CTG GAA ATC AAA CGT ACG                                     411
Gly Thr Lys Leu Glu Ile Lys Arg Thr
            260                 265

(2) INFORMATION FOR SEQ ID NO: 28:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 7..426

(xi) SEQUENCE DESCRIPTION: SEQ ID NO: 28:

GTCGAC ATG ATG GTG TTA AGT CTT CTG TAC CTG TTG ACA GCC CTT CCG          48
       Met Met Val Leu Ser Leu Leu Tyr Leu Leu Thr Ala Leu Pro
       135                 140                 145

GGT TTC CTG TCA GAG GTG CAG CTT CAG GAG TCA GGA CCT AGC CTC GTG         96
Gly Phe Leu Ser Glu Val Gln Leu Gln Glu Ser Gly Pro Ser Leu Val
            150                 155                 160

AAA CCT TCT CAG ACT CTG TCC CTC ACC TGT TCT GTC ACT GGC GAC TCC         144
Lys Pro Ser Gln Thr Leu Ser Leu Thr Cys Ser Val Thr Gly Asp Ser
165                 170                 175

ATC ACT AAT GGT TTC TGG ATC TGG ATC CGG AAA TTC CCA GGG AAT AAA         192
Ile Thr Asn Gly Phe Trp Ile Trp Ile Arg Lys Phe Pro Gly Asn Lys
180                 185                 190                 195

CTT GAG TAC ATG GGC TAC ATA AGT TAC AGT GGT AGC ACT TAC TAC AAT         240
Leu Glu Tyr Met Gly Tyr Ile Ser Tyr Ser Gly Ser Thr Tyr Tyr Asn
            200                 205                 210

CCA TCT CTC AAG AGT CGA ATC TCC ATC ACT CGC GAC ACA TCC CAG AAC         288
Pro Ser Leu Lys Ser Arg Ile Ser Ile Thr Arg Asp Thr Ser Gln Asn
            215                 220                 225

CAG TTC TAC CTA CAA TTG AAT TCT GTG ACT ACT GAG GAC ACA GGC ACA         336
Gln Phe Tyr Leu Gln Leu Asn Ser Val Thr Thr Glu Asp Thr Gly Thr
            230                 235                 240

TAT TAC TGT GCC TGC CGC AGT TAC GGG AGG ACC CCG TAC TAC TTT GAC         384
Tyr Tyr Cys Ala Cys Arg Ser Tyr Gly Arg Thr Pro Tyr Tyr Phe Asp
            245                 250                 255
```

```
TTC TGG GGC CAA GGC ACC ACT CTC ACC GTC TCC TCA GCT AGC        426
Phe Trp Gly Gln Gly Thr Thr Leu Thr Val Ser Ser Ala Ser
260                 265                 270
```